(12) United States Patent
Rasmussen et al.

(10) Patent No.: US 7,655,221 B2
(45) Date of Patent: Feb. 2, 2010

(54) METHODS OF TREATING DISEASE WITH RANDOM COPOLYMERS

(75) Inventors: James Rasmussen, Cambridge, MA (US); Jianxin Zhang, Acton, MA (US); Sam Baldwin, Westford, MA (US); Eric Zanelli, Sudbury, MA (US); Bei Yu, West Roxbury, MA (US); Dustan Bonnin, Belmont, MA (US); Keith Johnson, Hudson, MA (US)

(73) Assignee: Peptimmune, Inc., Cambridge, MA (US)

( * ) Notice: Subject to any disclaimer, the term of this patent is extended or adjusted under 35 U.S.C. 154(b) by 0 days.

(21) Appl. No.: 11/283,406

(22) Filed: Nov. 17, 2005

(65) Prior Publication Data

US 2006/0189527 A1 Aug. 24, 2006

Related U.S. Application Data

(63) Continuation-in-part of application No. PCT/US2005/016340, filed on May 9, 2005, and a continuation-in-part of application No. PCT/US2005/016344, filed on May 9, 2005.

(60) Provisional application No. 60/569,292, filed on May 7, 2004, provisional application No. 60/663,333, filed on Mar. 18, 2005.

(51) Int. Cl.
*A61K 31/74* (2006.01)
*A61K 38/02* (2006.01)

(52) U.S. Cl. .................. 424/78.08; 424/78.37; 514/2

(58) Field of Classification Search .................. None
See application file for complete search history.

(56) References Cited

U.S. PATENT DOCUMENTS

| | | | |
|---|---|---|---|
| 3,849,550 A | 11/1974 | Teitelbaum et al. |
| 5,800,808 A | 9/1998 | Konfino et al. |
| 5,858,964 A | 1/1999 | Aharoni et al. |
| 6,214,791 B1 | 4/2001 | Arnon et al. |
| 6,844,314 B2 | 1/2005 | Eisenbach-Schwartz et al. |

(Continued)

FOREIGN PATENT DOCUMENTS

WO    WO 92/02543    2/1992

(Continued)

OTHER PUBLICATIONS

Merriam Webster's Collegiate Dictionary, Tenth Edition, 1996, p. 36.*

(Continued)

*Primary Examiner*—Jeffrey E Russel
(74) *Attorney, Agent, or Firm*—Ropes & Gray LLP

(57) ABSTRACT

The invention relates to novel methods and kits for treating or preventing disease through the administration of random copolymers comprising amino acids tyrosine (Y), phenylalanine (F), alanine (A), and lysine (K). The invention also relates to the treatment of autoimmune diseases, such as multiple sclerosis, and to the administration of random copolymers in treatment regimen comprising formulations that are administered at intervals greater than 24 hours, or to sustained release formulations which administer the copolymer over a period greater than 24 hours. The invention further relates to methods for conducting a pharmaceutical business comprising manufacturing, licensing, or distributing kits containing or relating to the formulations or dosing regimens of random copolymer described herein.

29 Claims, 18 Drawing Sheets

U.S. PATENT DOCUMENTS

| | | | |
|---|---|---|---|
| 2001/0007758 A1* | 7/2001 | Weiner et al. | 435/69.1 |
| 2002/0055466 A1 | 5/2002 | Aharoni et al. | |
| 2002/0183385 A1 | 12/2002 | Ellison et al. | |
| 2003/0004099 A1 | 1/2003 | Eisenbach-schwartz et al. | |
| 2004/0038887 A1* | 2/2004 | Strominger et al. | 514/12 |

FOREIGN PATENT DOCUMENTS

| | | |
|---|---|---|
| WO | WO 00/05249 | 2/2000 |
| WO | WO 00/05250 | 2/2000 |
| WO | WO 00/18794 | 4/2000 |
| WO | WO 00/20010 | 4/2000 |
| WO | WO 00/27417 | 5/2000 |
| WO | WO 03/000277 A2 | 1/2003 |
| WO | WO 03/029276 A2 | 4/2003 |
| WO | WO 03/047500 A2 | 6/2003 |
| WO | WO 03/074546 | 9/2003 |
| WO | WO 2004/064717 | 8/2004 |
| WO | WO-2005/112972 | 12/2005 |
| WO | WO-2005/120542 | 12/2005 |

OTHER PUBLICATIONS

KMLE Medical Dictionary—Online medical dictionary, terminology, abbreviations, drugs. 2006-2007, pp. 1-8, http://www.kmle.com.*

George C. Tsokos, M.D., B Cells, Be Gone—B-Cell Depletion in the Treatment of Rheumatoid Arthritis, New England Journal of Medicine, vol. 350, No. 25, Jun. 17, 2005, pp. 2546-2548.*

Bert A. 't hart, et al., Evaluating the validity of animal models for research into therapies for immune-based disorders, DDT, Jun. 12, 2004, vol. 9, No. 12, pp. 517-524.*

Herman Waldmann, Clinical Use of Campath -1H, Transplantation Reviews, Oct. 2003, vol. 17, No. 4, pp. S5-S7.*

Michael H. Barnett and John W. Rinease, Relapsing and Remitting Multiple Sclerosis: Pathology of the Newly Forming Lesion, Ann. Neurol., 2004, vol. 55, pp. 458-468.*

Abhijit Chaudhuri and Peter O. Behan, Multiple Sclerosis is Not an Autoimmune Disease, Arch Neurol., Oct. 2004, vol. 61, pp. 1610-1612.*

Daniel Altmann, Evaluating the Evidence for Multiple Sclerosis an Autoimmune Disease and In Reply Abhijit Chaudhuri and Peter O. Behan, , Arch Neurol., Apr. 2005, vol. 62, pp. 688-690.*

Fridkis-Hareli et al., "Novel synthetic amino acid copolymers that inhibit autoantigen-specific T cell responses and suppress experimental autoimmune encephalomyelitis", The Journal of Clinical Investigation, Jun. 2002, vol. 109, No. 12, pp. 1635-1643.

Suhayl Dhib-Jalbut, "Glatiramer acetae (cCpaxone® ) therapy for multiple sclerosis", Pharmacology & Therapeutics, 98 (2003) pp. 245-255.

Illes Zsolt et al., "Modified amino acid copolymers suppress myelin basic protein 85-99-induced encephalomyelitis in humanized mice through different effects on T cells", Proc. Natl. Acad. of Sciences; vol. 101, No. 32, (2004) (Abstract).

Farina et al., "Glatiramer acetate in multiple sclerosis: update on potential mechanisms of action", http://neurology.thelancet.com, vol. 4, 567-575, Sep. 2005.

http://eanatomy.cc/4.htm, Section 4, The Acquired Immune Respose, 1-71, May 9, 2005.

Kersten et al., "Antigen delivery systems", Expert Rev. Vaccines 3(4), 453-462, 2004.

Flechter et al., "Copolymer 1 (Glatiiramer Acetate) in Relapsing Forms of Multiple Sclerosis:Open Multicenter Study of Alterntae-Day Administration", Clinical Neuropharmacology, vol. 25, No. 1, Nov. 15, 2002.

Karandikar et al., "Glatiramer acetate (Copaxone) therapy induces CD8+ T cell responses in patientes with multiple sclerosis", The Journal of Clinical Investigation, vol. 109, No. 5, 641-649, Mar. 2002.

Fridkis-Hareli et al., "Direct binding of myelin basic protein and synthetic copolymer 1 to class II major histocompatibility complex molecules on living antigen-presenting cells—specificity and promiscuity", Proc. Natl. Acad. Sci. USA, vol. 91, 4872-4876, May 1994.

Jacchieri et al., "Proving the Influence of Sequence-Dependent Interactions upon $\alpha$-Helix Stability in Alanine-Based Linear Peptides", Biopolymers, vol. 33, No. 6, 971-984, 1993.

Fridkis-Hareli et al., "Novel synthetic amino acid copolymers that inhibit autoantigen-specific T cell responses and suppress experimental autoimmune encephalomyelitis", The Journal of Clinical Investigation, vol. 109, No. 12, 1635-1643, Jun. 2002.

International Search Report dated Jul. 20, 2007 from corresponding application PCT/US2006/044864.

International Search Report dated Jul. 6, 2007 from corresponding application No. PCT/US2006/044699.

Li, Q. et al., "Glatiramer acetate blocks the activation of THP-1 cells by interferon-$\gamma$", European Journal of Pharmacology, vol. 342, 1998, 303-310.

Melton, L. et al., "Designed polyanionic coiled-coil proteins: acceleration of heparin cofactor II inhibition of thrombin", Int. J. Peptide Protein Res., 45, 1995, 44-52.

Wagner, D. et al., "Deuterium exchange of $\alpha$-helices and $\beta$-sheets as monitored by electrospray ionization mass spectrometry", Protein Science, 3, 1994, 1305-1314.

European Search Report dated Feb. 27, 2008 from European Application No. 05724381.8.

Saoudi et al., Is pathogenic humoral autoimmunity a Th1 response?, Immunology Today, vol. 21, 6, 2000, pp. 306-307.

* cited by examiner

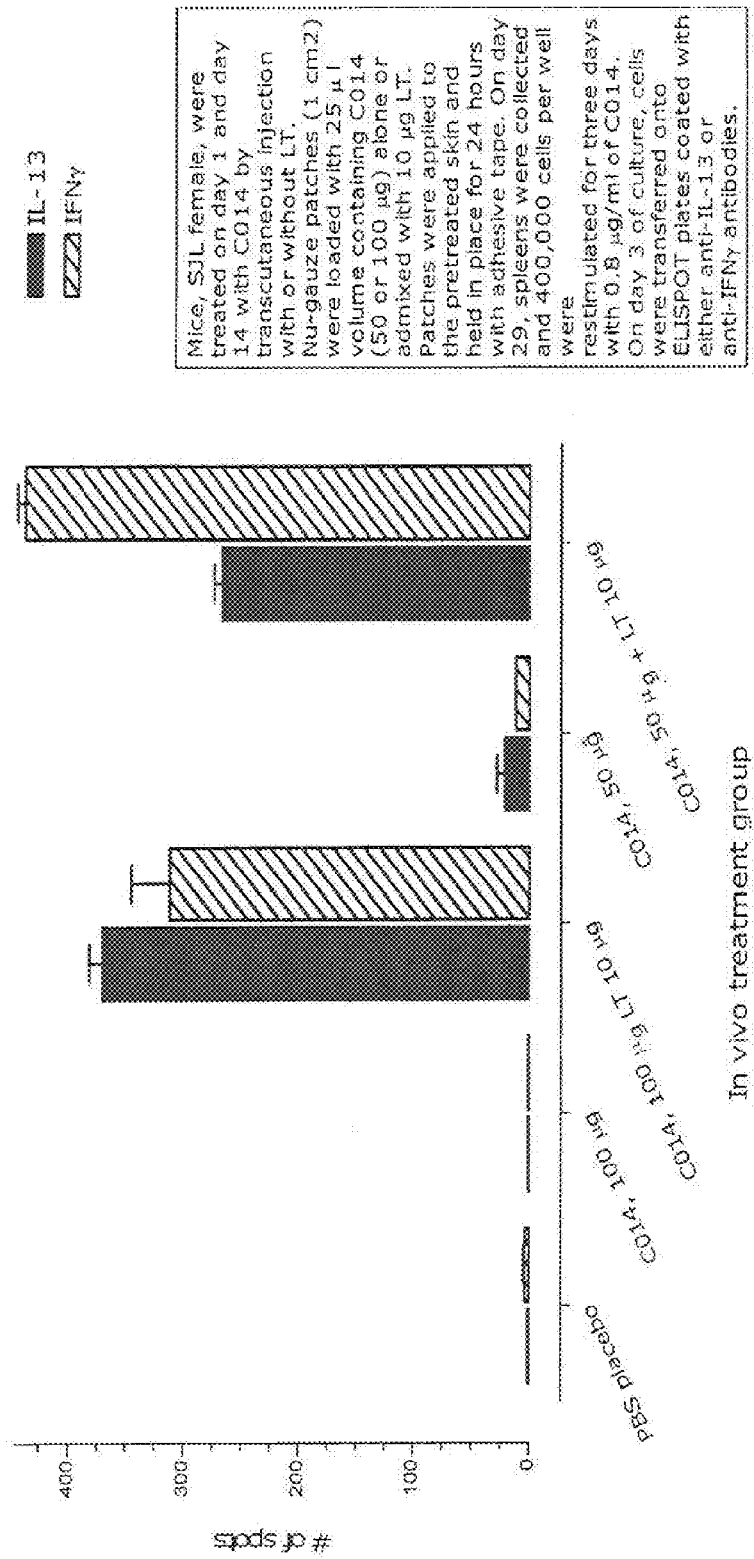

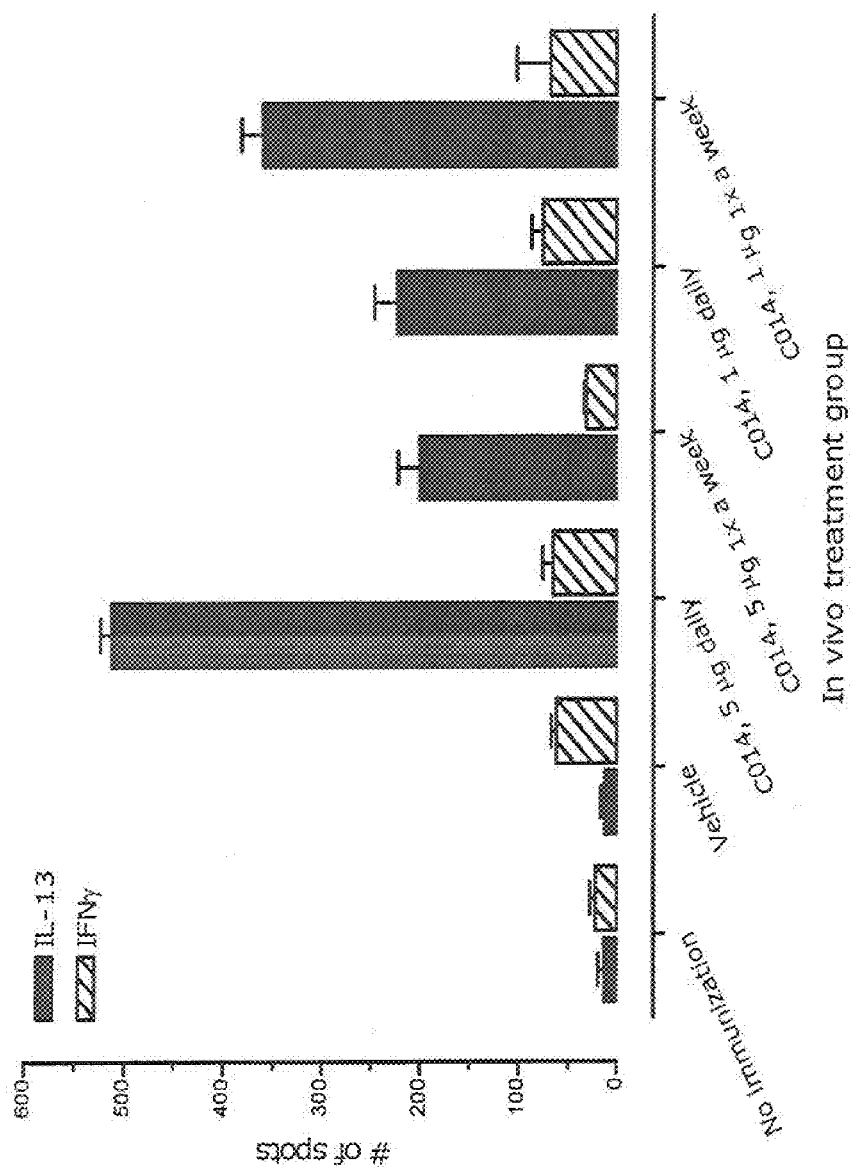

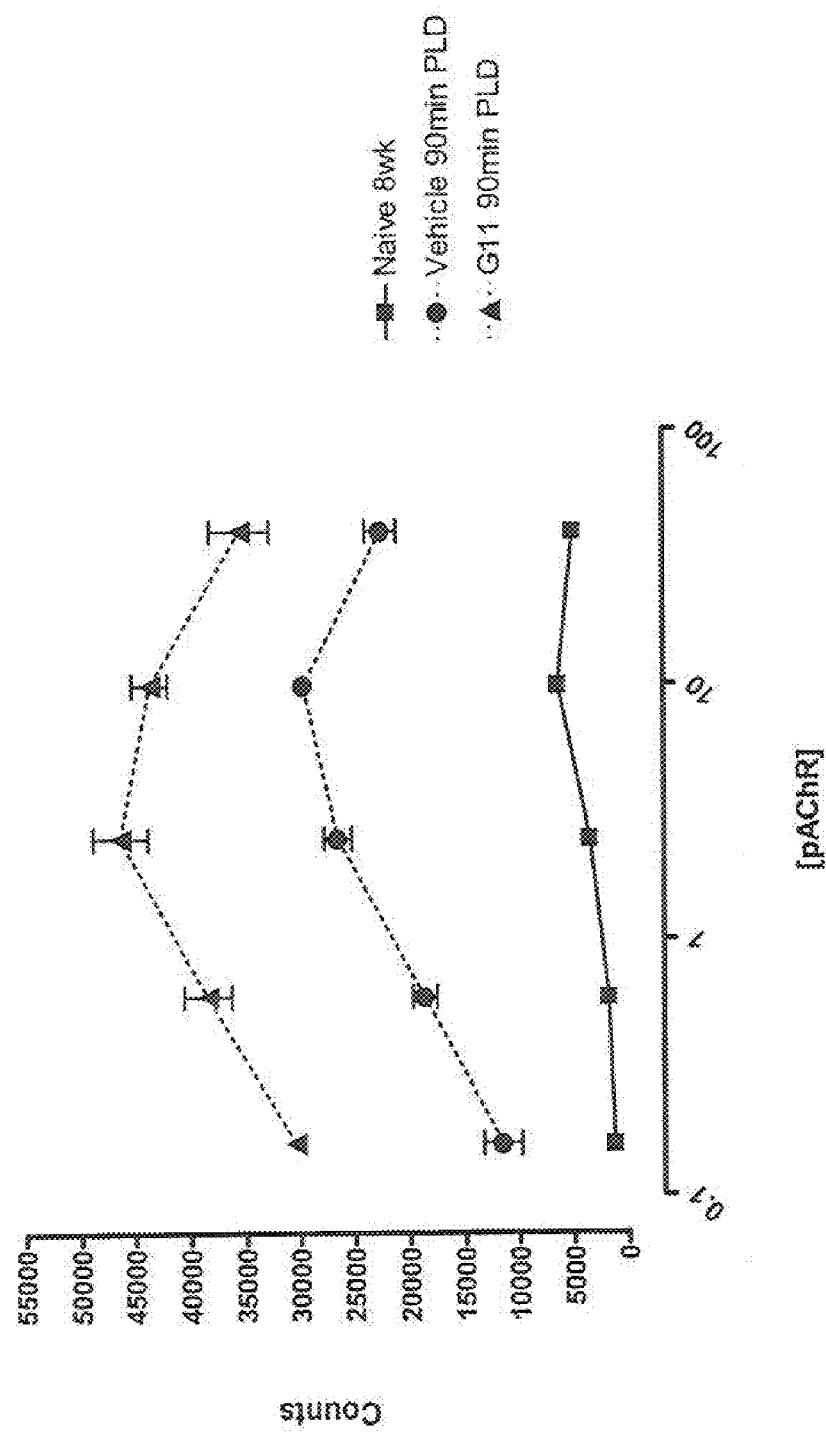

Figure 16
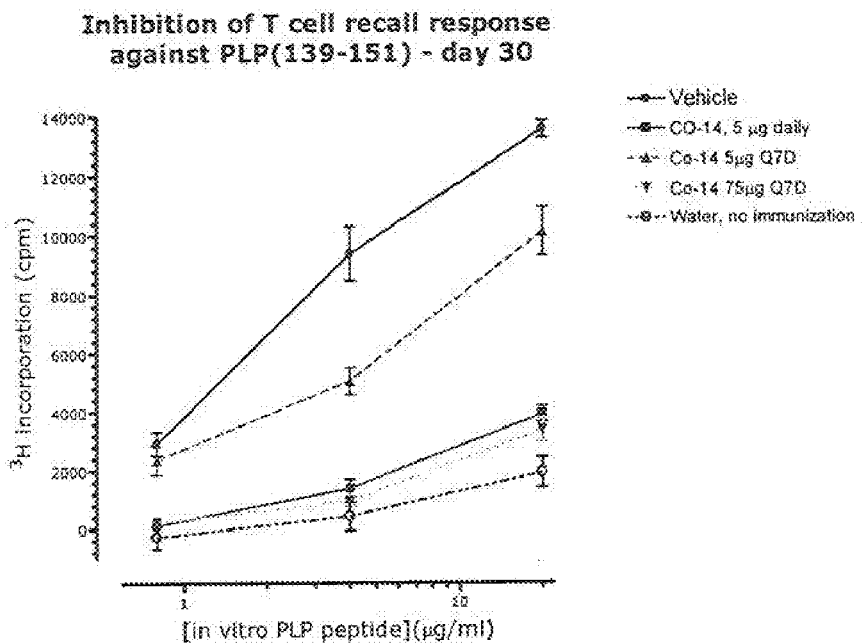
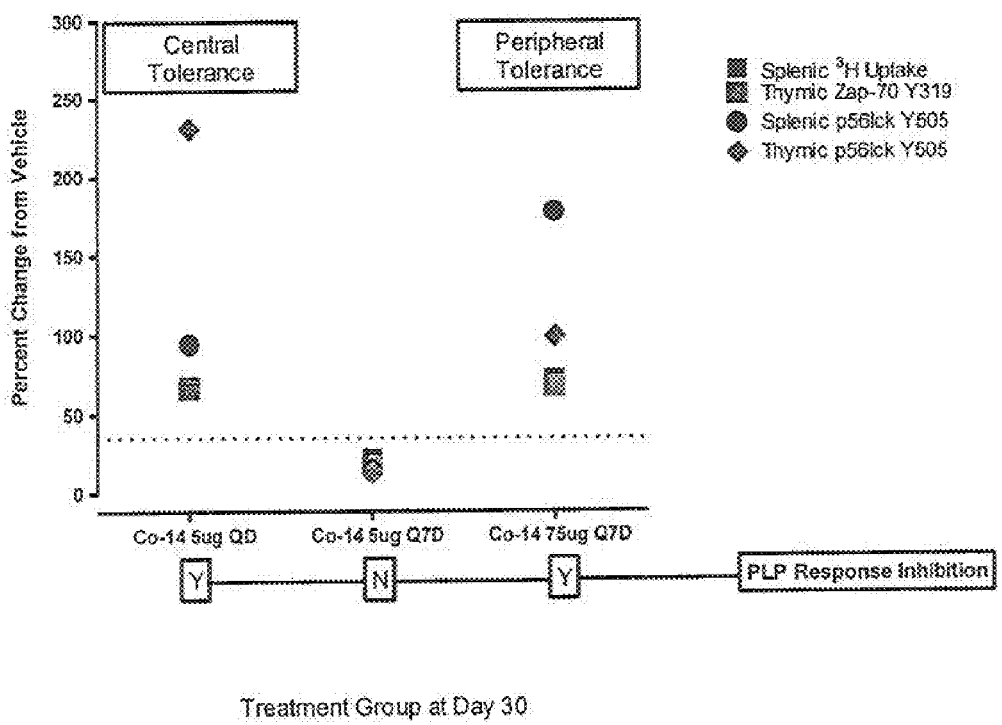

METHODS OF TREATING DISEASE WITH RANDOM COPOLYMERS

CROSS REFERENCE TO RELATED APPLICATIONS

This application is a continuation-in-part of PCT/US05/016340 filed May 9, 2005 and PCT/US05/016344 filed May 9, 2005, which applications claim priority to U.S. Provisional Application Ser. No. 60/569,292 filed May 7, 2004, and to U.S. Provisional Application Ser. No. 60/663,333 filed Mar. 18, 2005, the entire contents of all of which is hereby incorporated by reference.

BACKGROUND OF THE INVENTION

An autoimmune disease results from an inappropriate immune response directed against a self antigen (an autoantigen), which is a deviation from the normal state of self-tolerance. Self-tolerance arises when the production of T cells and B cells capable of reacting against autoantigens has been prevented by events that occur in the early development of the immune system. The cell surface proteins that play a central role in regulation of immune responses through their ability to bind and present processed peptides to T cells are the major histocompatibility complex (MHC) molecules (Rothbard, J. B., et al., 1991, *Annu. Rev. Immunol.* 9:527). Autoimmune diseases include rheumatoid arthritis (RA), multiple sclerosis (MS), human type I or insulin-dependent diabetes mellitus (IDDM), autoimmune uveitis, primary biliary cirrhosis (PBC) and celiac disease.

One target for inhibition of an autoimmune response is the set of lymphocyte surface protein MHC molecules, particularly a protein encoded by an MHC class II gene, for example, HLA-DR, -DQ and -DP. Each of the MHC genes is found in a large number of alternative or allelic forms within a mammalian population. The genomes of subjects affected with certain autoimmune diseases, for example MS and RA, are more likely to carry one or more characteristic MHC class II alleles, to which that disease is linked.

A number of therapeutic agents have been developed to treat autoimmune diseases, including general anti-inflammatory drugs such as COX-2 inhibitors, i.e., agents that can prevent formation of low molecular weight inflammatory compounds by inhibiting a cyclooxygenase; agents that can function by inhibiting a protein mediator of inflammation, for example, by sequestering the inflammatory protein tumor necrosis factor (TNF) with an anti-TNF specific monoclonal antibody or antibody fragment, or with a soluble form of the TNF receptor; and agents that target a protein on the surface of a T cell and generally prevent interaction with an antigen presenting cell (APC) by inhibiting the CD4 receptor or the cell adhesion receptor ICAM-1. However, compositions having natural folded proteins as therapeutic agents can encounter problems in production, formulation, storage, and delivery. Several of these problems necessitate delivery to the patient in a hospital setting.

An agent that interacts and binds relatively nonspecifically to several MHC class II molecules is Copolymer 1 (Cop 1), a synthetic amino acid heteropolymer that was shown to be capable of suppressing experimental allergic encephalomyelitis (EAE; Sela, M. et al., 1990, Bull. Inst. Pasteur (Paris)), which can be induced in the mouse and is a model for MS. Copolymer 1, which is poly(Y,E,A,K) also known as glatiramer acetate or "YEAK" using the one letter amino acid code (see infra; Y represents tyrosine, E glutamic acid, A alanine, and K lysine), has been used to treat relapsing forms of MS but does not suppress the disease entirely (Bornstein, M. B., et al., 1987, *N. Engl. J. Med.* 317:408; Johnson, K. P. et al., 1995, *Neurology* 45:1268).

Although random copolymers may be effective for the treatment of autoimmune diseases (Simpson, D. et al., 2003, *BioDrugs* 17(3):207-10), their repeated administration may cause undesired side effects. Accordingly, there is a need for improved methods for the treatment of autoimmune diseases with random copolymers which result in fewer side effects.

BRIEF SUMMARY OF THE INVENTION

The invention provides methods and kits for the treatment or prevention of disease in a subject, preferably in a human. One aspect of the invention provides methods of treating or preventing a disease, the method comprising administering to said subject a dosing regimen of an effective amount of a random copolymer for the amelioration of a disease treatable with the random copolymer, said effective amount delivered to said subject at time intervals greater than 24 hours, 36 hours, or more preferably greater than 48 hours. A related aspect of the invention provides a method for the treatment of a subject in need thereof, comprising administering to said subject a dosing regimen of an effective amount of a random copolymer for the amelioration of a disease treatable with the random copolymer, said effective amount delivered to the subject using a sustained-release formulation which administers the random copolymer over a period of at least 2 days, at least 4 days, or at least 6 days, wherein the effective amount is an amount that is effective if delivered daily. In some embodiments, the disease of the methods of the present invention is mediated by T-cells, and in particular $T_H1$ cells or cells with $T_H1$ immune posture, or is a disease which is exacerbated by an excess of inflammatory cytokines. In some embodiments, the disease is an autoimmune disease, such as multiple sclerosis. In some preferred embodiments, the random copolymer comprises tyrosine (Y), phenylalanine (F), alanine (A) and lysine (K) (YFAK copolymer). In other embodiments, the random copolymer is Copolymer 1 (YEAK). In particular, the method of present invention further comprises administering to said subject an anti-lymphocyte therapies. In one embodiment, the anti-lymphocyte therapy comprises administering an agent selected from the group consisting of a polyclonal antibody or a monoclonal antibody. In certain embodiments, the polyclonal antibody is antithymocyte gamma globulin (ATGAM). In other embodiment, the antibody is a monoclonal antibody selected from the group consisting of alemtuzumab (Campath®), muromonab (OKT®3), daclizumab, and basiliximab. In another embodiment, the method of the invention further comprises administering to said subject an anti B-cell therapy. In one embodiment, the anti-B-cell therapy comprises administering anti CD-20 antibody. One aspect of the invention is a method treating a disease treatable by administering a random copolymer composition comprising administering to a subject in need thereof a dosing regimen of an effective amount of a random copolymer composition for the amelioration of said disease, wherein the disease is selected from the group consisting of allergies, asthma, atopic dermatitis, and neuroprotection.

The invention is not limited to any particular random copolymer or mode of administration.

The invention also provides kits for the treatment of disease. One aspect of the invention provides a kit for the treatment of an autoimmune disease comprising (i) a composition comprising a random copolymer and (ii) instructions for administering the composition to a subject at time intervals of at least 24 hours, or more preferably 36 or 48 hours or longer. In preferred embodiments, the composition is formulated for subcutaneous injection, the random copolymer is YFAK or Copolymer 1, and the disease is an autoimmune disease, such as multiple sclerosis, particularly relapsing-remitting multiple sclerosis.

The invention further provides agents for the manufacture of medicaments to treat diseases. Any methods disclosed herein for treating or preventing a disease by administering a random copolymer to a subject may be applied to the use of the random copolymer in the manufacture of a medicament to treat that disease. Accordingly, one aspect of the invention provides the use of a random copolymer for the treatment of a disease in a subject, wherein the random copolymer is formulated to be administered to the subject at intervals greater than 24 hours, 36 hours, and more preferably of at least 48 hours. In preferred embodiments, the random copolymer is Copolymer 1 (YEAK), and the disease is an autoimmune disease, such as multiple sclerosis, particularly relapsing-remitting multiple sclerosis.

The invention further provides methods of conducting a pharmaceutical business.

BRIEF DESCRIPTION OF THE DRAWINGS

FIG. 13A-C shows opposing TH1/TH2 ratios which are dose, regimen, and administration dependent. The recall response shown is representative of both of the two TH1/TH2 conditions.

FIG. 14 shows the ability of Co-14 to mediate recall responses to a Myasthenia Gravis-associated acetyl choline receptor peptide.

FIG. 16 shows the differential induction of peripheral and central tolerance.

DETAILED DESCRIPTION OF THE INVENTION

I. Overview

Figure 1:
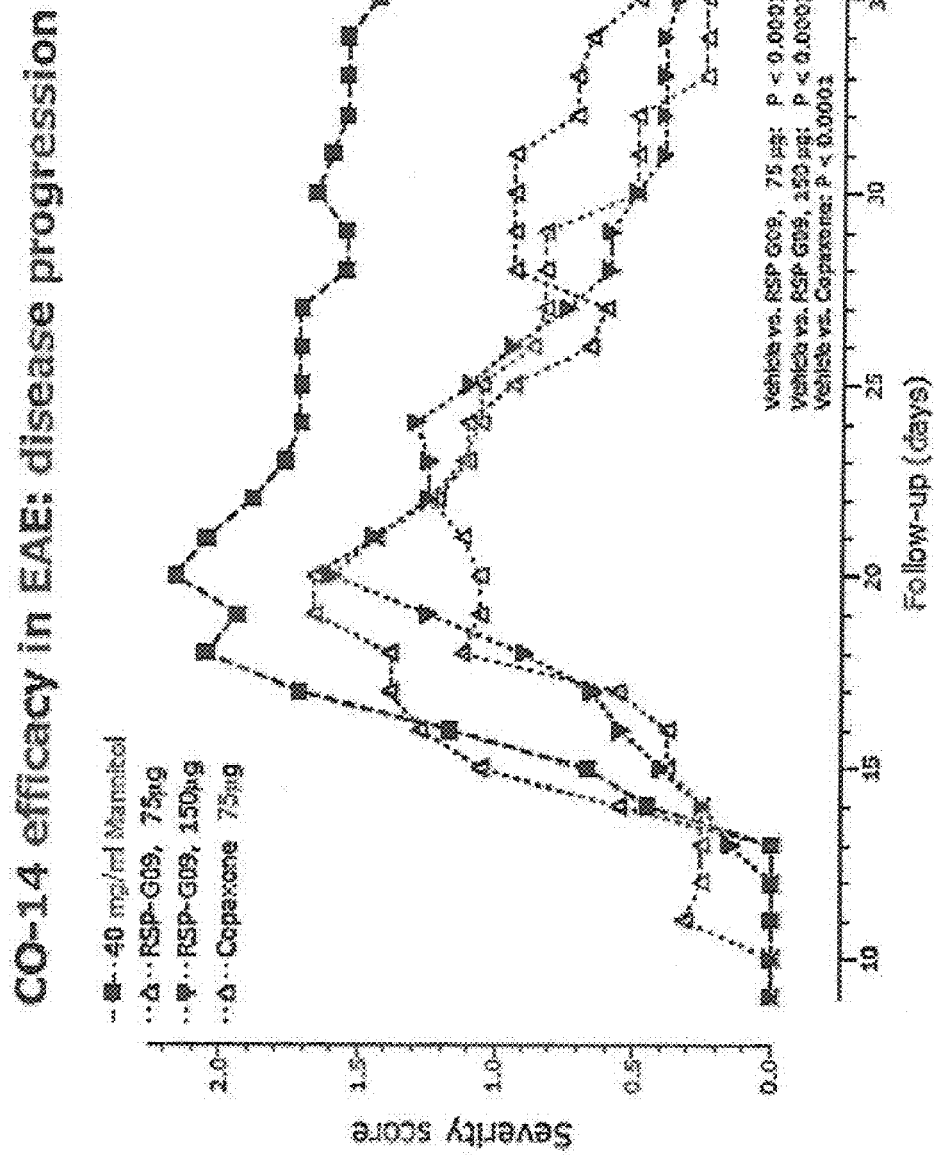
FIG. 1 shows the effect of copolymer administration on the disease progression of EAE.

The invention broadly relates to the treatment and prophylaxis of diseases by the administration of random copolymers, to the use of the random copolymers in the manufacture of medicaments to treat disease, and to kits comprising both random copolymers and instructions. The invention also relates to the treatment of autoimmune diseases and to long-lasting random copolymer formulations for the treatment of disease.

One aspect of the invention provides a method for the treatment of a subject comprising administering to said subject a dosing regimen of an effective amount of a random copolymer for the amelioration of a disease treatable with the random copolymer, said effective amount delivered to said subject at time intervals greater than 36 hours. A related aspect of the invention provides a method for the treatment of a subject comprising administering to said subject a dosing regimen of an effective amount of at least one random copolymer for the amelioration of a disease treatable with the random copolymer, said effective amount of at least one copolymer being delivered to said subject at time intervals greater than 24 hours, and in particular greater than 48 hours. In one embodiment, the effective amount of the random copolymer that is administered at intervals greater than 24 hours is an amount that is effective when administered daily. In a related embodiment, the effective amount that is administered at intervals greater than 24 hours is an amount that would be effective if administered daily. In yet another related embodiment, the effective amount that is administered at intervals greater than 24 hours is an amount that is known to be effective if administered daily. In an embodiment of this invention, the effective amount consists of between 10 mg and 30 mg, or between 15 mg and 25 mg. In other embodiments, the effective amount is about 20 mg. In another embodiment, the effective amount is less than 20 mg. In specific embodiments, the effective amount is "x" mg, wherein "x" is any integer between 1 and 20.

In one embodiment of the methods provided herein, the subject is afflicted with a disease treatable with the random copolymer. In one embodiment, the disease is mediated by T-cells, and in particular $T_H1$ cells or cells with $T_H1$ immune posture, or is a disease which is exacerbated by an excess of inflammatory cytokines. In another embodiment, the subject is afflicted with at least one autoimmune disease. In one embodiments, the subject is afflicted with at least one disease selected from the group consisting of multiple sclerosis, type-I diabetes, Hashimoto's thyroiditis, Crohn's disease, rheumatoid arthritis, systemic lupus erythematosus (SLE), gastritis, autoimmune hepatitis, hemolytic anemia, autoimmune hemophilia, autoimmune lymphoproliferative syndrome (ALPS), autoimmune uveoretinitis, glomerulonephritis, Guillain-Barré syndrome, psoriasis, myasthenia gravis, autoimmune encephalomyelitis, Goodpasture's syndrome, Grave's disease, paraneoplastic pemphigus, autoimmune thrombocytopenic purpura, scleroderma with anti-collagen antibodies, mixed connective tissue disease, pernicious anemia, polymyositis, idiopathic Addison's disease, autoimmune-associated infertility, glomerulonephritis, bullous pemphigoid, Sjogren's syndrome, idiopathic myxedema and colitis. In preferred embodiments, the disease is multiple sclerosis or relapsing-remitting multiple sclerosis. In additional embodiments of the methods provided herein, the disease is host-versus-graft disease (HVGD) or graft-versushost disease (GVHD) or both. In preferred embodiments of the methods described herein, the subject is a mammal, or more preferably a human.

In one embodiment of the methods described herein, the dosing regimen comprises intravenous, subcutaneous, intramuscular, intradermal, intraperitoneal, intradermal or oral administration. The random copolymer may also be administered via devices designed to deliver the random copolymer continuously, such as a transdermal patch or pump or implant. For example, a transdermal patch may be used to administer the random copolymer over a span of 12 hours every 48 hours or longer, or a pump may be used to administer the copolymer over a period of two days every four or more days. In a related aspect, the copolymer is administered in a sustained release formulation.

The invention also provides a method for the treatment of a subject in need thereof comprising administering to said subject a dosing regimen of an effective amount of a random copolymer for the amelioration of a disease treatable with the random copolymer, said effective amount delivered to the subject using a sustained-release formulation which administers the random copolymer over a period of at least 2 days, at least 4 days, or at least 6 days, wherein the effective amount is an amount that is effective if delivered daily. In preferred embodiments, the sustained release formulation administers the copolymer over a period of at least 2, 3, 4, 5, 6, 7, 8, 9, 10, 11, 12, 13 or 14 days. In another embodiment, the total dosage delivered daily by the sustained release formulation is less than 90%, 80%, 70%, 60%, 50%, 40%, 30%, 20%, 10% or 5% of a daily dosage known to be effective in the treatment of the disease. In a specific embodiment, the sustained release formulation administers 25% or less, per day, of a dosage of a random copolymer which is known to be effective in treating the disease when administered daily. As an illustrative example, if Copolymer 1 (YEAK) is known to be effective in the treatment of relapsing-remitting multiple sclerosis when administered daily in dosages of 20 mg, such as by one daily subcutaneous injection of 20 mg, the invention provides sustained release formulations of Copolymer 1 which results in a daily administration of copolymer of less than 20 mg, and in particular less than about 10 mg, 9 mg, 8 mg, 7 mg, 6 mg, 5 mg, 4 mg, 3 mg, 2 mg or 1 mg of Copolymer 1.

In some embodiments of the methods described herein, the methods further comprise administering an additional therapeutically active agent to the subject, such as an anti-inflammatory agent. In preferred embodiments, the agent is useful in treating the disease. In another preferred embodiment, the agent synergizes with the random copolymer to treat the disease.

In some embodiments of the methods described herein, the dosing regimen comprises administering the random copolymer to the subject multiple times, with a time interval between each administration. In preferred embodiments, the time interval between each administration is at least 36, 48, 72, 96, 120, or 144 hours. In another preferred embodiment, the time interval between each administration is between 36 hours and 14 days, or at least 7 days. In a related embodiment, at least one of the time intervals between administrations is at least 36, 48, 72, 96, 120, or 144 hours, at least 7 days, or between 36 hours and 14 days. In another related embodiment, at least 10%, 20%, 30%, 40% or more preferably 50% of the time intervals between administrations are at least 36, 48, 72, 96, 120, or 144 hours, at least 7 days, or between 36 hours and 14 days. In yet another related embodiment, the average time interval between administrations is at least 36, 48, 72, 96, 120, or 144 hours, at least 7 days, or between 36 hours and 14 days.

In some embodiments of the methods described herein, the effective amount of the random copolymer is between 0.02 mg per dose and 2000 mg per dose, or more preferably between 2 mg per dose and 200 mg per dose.

In some embodiments of the methods described herein, the random copolymer is selected from the group consisting of Copolymer 1 (YEAK), YFAK, VYAK, VWAK, VEAK and FEAK. In a preferred embodiment, the random copolymer is Copolymer 1. In another preferred embodiment, the random copolymer is YFAK. In another embodiment, the random copolymer is a terpolymer, such as one selected from the group consisting of YAK, YEK, KEA and YEA. In yet another embodiment, the random copolymer has between one and 10 anchor residues.

The invention also provides kits for the treatment of disease. One aspect of the invention provides a kit for the treatment of an autoimmune disease comprising (i) a composition comprising a random copolymer and (ii) instructions for administering the composition to a subject at time intervals of at least 36 hours. In a preferred embodiment, the random copolymer in the kit is Copolymer 1. In another preferred embodiments, the random copolymer in the kit is YFAK. In some embodiments, the random copolymer in the kit is formulated for administration every about 24, 30, 36, 42, 48, 54, 60, 66, 72, 78, 84, 90, 96, 102, 108, 114, 120, 126, 132, 138, 144, 150, 156, 162, 168, 174, 180, 186, 192, 198, 204, 210, 216, 222, 228, 234, or 240 hours. In some embodiments, the instructions of the kit indicate that the random polymer is to be administered to the subject at time intervals of at least 24, 30, 36, 42, 48, 54, 60, 66, 72, 78, 84, 90, 96, 102, 108, 114, 120, 126, 132, 138, 144, 150, 156, 162, 168, 174, 180, 186, 192, 198, 204, 210, 216, 222, 228, 234, or 240 hours.

In some embodiments of the kits provided by the invention, the composition is formulated as a sustained release formulation. In specific embodiments, the sustained release formulation delivers a total dosage that would be effective in treating the disease if said total dosage were administered daily. In other embodiments, the total dosage is about 20 mg, less than 20 mg, or x mg, wherein x is any integer between 1 and 20.

In another embodiment of the kits provided by the invention, the kit comprises instructions for administering the composition to a subject in need thereof at time intervals of at least 24, 36, 48, 72, 96, 120 or 144 hours or longer, at a dosage of about 20 mg per administration, while in other embodiments the dosage is less than 20 mg, such as x mg, wherein x is any integer between 1 and 20. In a related embodiment, the kit comprises instructions for administering the composition to a subject in need thereof at time intervals of at least 24 hours at a dosage that is effective in treating the disease if it were to be administered daily. In another related embodiment, the kit comprises instructions for administering the composition to a subject in need thereof at time intervals of at least 24 hours at a dosage that is effective in treating the disease when administered daily.

In some embodiments, the disease for which the kit is directed is mediated by T-cells, and in particular $T_H1$ cells, or the disease is one which is exacerbated by an excess of inflammatory cytokines. In another embodiments, the disease is an autoimmune disease for which the kit provides treatment is selected from the group consisting of multiple sclerosis, type-I diabetes, Hashimoto's thyroiditis, Crohn's disease, rheumatoid arthritis, systemic lupus erythematosus (SLE), gastritis, autoimmune hepatitis, hemolytic anemia, autoimmune hemophilia, autoimmune lymphoproliferative syndrome (ALPS), autoimmune uveoretinitis, glomerulonephritis, Guillain-Barré syndrome, psoriasis, myasthenia gravis, autoimmune encephalomyelitis, Goodpasture's syndrome, Grave's disease, paraneoplastic pemphigus, autoimmune thrombocytopenic purpura, scleroderma with anti-collagen antibodies, mixed connective tissue disease, pernicious anemia, polymyositis, idiopathic Addison's disease, autoimmune-associated infertility, bullous pemphigoid, Sjogren's syndrome, idiopathic myxedema and colitis. In specific embodiments, the disease is multiple sclerosis, diabetes or arthritis. In a preferred embodiment, the disease is relapsing-remitting multiple sclerosis. The kit may also comprise packaging and a means of administrating the copolymer, such as a hypodermic syringe, needles, measuring devices such as a spoon or graduated container, an inhaler or a pump. The instructions on the kit may also contain instructions for home use.

The invention further provides agents for the manufacture of medicaments to treat diseases. Any methods disclosed herein for treating or preventing a disease by administering a random copolymer to a subject may be applied to the use of the random copolymer in the manufacture of a medicament to treat that disease. Accordingly, one aspect of the invention provides the use of a random copolymer for the treatment of a disease in a subject, wherein the random copolymer is formulated to be administered to the subject at intervals greater than 24 hours, and more preferably of at least 48 hours. In preferred embodiments, the random copolymer is Copolymer 1, and the disease is an autoimmune disease, such as multiple sclerosis or more particularly relapsing-remitting multiple sclerosis. In other preferred embodiments, the random copolymer is YFAK.

Another aspect of the invention provides for certain methods of doing business. In particular, the invention provides methods of conducting a pharmaceutical business wherein the kits and formulations are marketed to healthcare providers or directly to subjects in need of such kits. One aspect provides a method for conducting a pharmaceutical business, comprising marketing to healthcare providers, or to patients in need of such kits, the benefits of using any of the kits described herein in the treatment of a disease or disorder. A related aspect provides a method for conducting a pharmaceutical business, comprising: (a) manufacturing any of the kits described herein; and (b) marketing to healthcare providers, or to patients in need of such kits, the benefits of using the kit in the treatment of a disease or disorder. In some embodiments, the rights to develop and market such formulations or to conduct such manufacturing steps may be licensed to a third party for consideration. In some embodiments, the disease is multiple sclerosis, such as relapse-remitting multiple sclerosis. In another embodiment, the kits comprise Copolymer 1 or YFAK.

In another embodiment, the marketing to healthcare providers or to patients comprises an indication to administer 50 mg, or more preferably 20 mg or less of the random copolymer every 5 to 7 days. In other embodiments, the marketing comprises an indication to administer the random copolymer every at least 2, 3, 4, 5, 6, 7, 8, 9, 10, 11, 12, 13 or 14 days. In another embodiment, the marketing to healthcare providers or to patients comprises an indication to administer 50 mg, or more preferably 20 mg or less of the random copolymer, every 5 to 7 days. In yet another embodiment, the marketing comprises an indication of reduced side effects in using the kits or formulations described herein compared to existing formulations of the same or a different random copolymer. In a specific embodiment, the existing formulations are administered more frequently to the patient, or with shorter intervals between administrations, while in another embodiment the existing formulations result in a higher average daily dosage than those of the kit that is marketed. The higher average daily dosage may be, for example, 20, 50, 100, 200, or 500% higher than those provided by the kits.

II. Definitions

For convenience, certain terms employed in the specification, examples, and appended claims, are collected here. Unless defined otherwise, all technical and scientific terms used herein have the same meaning as commonly understood by one of ordinary skill in the art to which this invention belongs.

The articles "a" and "an" are used herein to refer to one or to more than one (i.e., to at least one) of the grammatical object of the article. By way of example, "an element" means one element or more than one element.

The term "including" is used herein to mean, and is used interchangeably with, the phrase "including but not limited" to.

The term "or" is used herein to mean, and is used interchangeably with, the term "and/or," unless context clearly indicates otherwise.

The term "such as" is used herein to mean, and is used interchangeably, with the phrase "such as but not limited to".

A "patient" or "subject" to be treated by the method of the invention can mean either a human or non-human animal, preferably a mammal.

The term "autoimmune condition" or "autoimmune disease" means a disease state caused by an inappropriate immune response that is directed to a self-encoded entity which is known as an autoantigen. The copolymer compounds provided herein can be used to treat symptoms of an autoimmune disease, a class of disorder which includes Hashimoto's thyroiditis; idiopathic myxedema, a severe hypothyroidism; multiple sclerosis, a demyelinating disease marked by patches or hardened tissue in the brain or the spinal cord; myasthenia gravis which is a disease having progressive weakness of muscles caused by autoimmune attack on acetylcholine receptors at neuromuscular junctions; Guillain-Barre syndrome, a polyneuritis; systemic lupus erythematosis; uveitis; autoimmune oophoritis; chronic immune thrombocytopenic purpura; colitis; diabetes; Grave's disease, which is a form of hypothyroidism; psoriasis; pemphigus vulgaris; and rheumatoid arthritis (RA).

The term "demyelinating condition" includes a disease state in which a portion of the myelin sheath, consisting of plasma membrane wrapped around the elongated portion of the nerve cell, is removed by degradation. A demyelinating condition can arise post-vaccination, post-anti TNF treatment, post-viral infection, and in MS.

The term "derivative" of an amino acid means a chemically related form of that amino acid having an additional substituent, for example, N-carboxyanhydride group, a γ-benzyl group, an ε-N-trifluoroacetyl group, or a halide group attached to an atom of the amino acid.

The term "analog" means a chemically related form of that amino acid having a different configuration, for example, an isomer, or a D-configuration rather than an L-configuration, or an organic molecule with the approximate size, charge, and shape of the amino acid, or an amino acid with modification to the atoms that are involved in the peptide bond, so that the copolymer having the analog residue is more protease resistant than an otherwise similar copolymer lacking such analog, whether the analog is interior or is located at a terminus of the copolymer, compared to the copolymer without the analog.

The phrases "amino acid" and "amino acid copolymer" can include one or more components which are amino acid derivatives and/or amino acid analogs as defined herein, the derivative or analog comprising part or the entirety of the residues for any one or more of the 20 naturally occurring amino acids indicated by that composition. For example, in an amino acid copolymer composition having one or more tyrosine residues, a portion of one or more of those residues can be substituted with homotyrosine. Further, an amino acid copolymer having one or more non-peptide or peptidomimetic bonds between two adjacent residues is included within this definition.

The term "hydrophobic" amino acid means aliphatic amino acids alanine (A, or ala), glycine (G, or gly), isoleucine (I, or ile), leucine (L, or leu), methionine (M, or met), proline (P, or pro), and valine (V, or val), the terms in parentheses being the one letter and three letter standard code abbreviations for each amino acid, and aromatic amino acids tryptophan (W, or trp), phenylalanine (F, or phe), and tyrosine (Y, or tyr). These amino acids confer hydrophobicity as a function of the length of aliphatic and size of aromatic side chains, when found as residues within a copolymer or other polypeptide.

The term "charged" amino acid means amino acids aspartic acid (D or asp), glutamic acid (E or glu), arginine (R or arg) and lysine (K or lys), which confer a positive (lys, and arg) or negative (asp, glu) charge at physiological values of pH on an aqueous solution of a copolymer or other amino acid composition containing one or more residues of these amino acids. Histidine (H or his) is hydrophobic at pH 7, and charged at pH 6.

The terms "disorders" and "diseases" are used inclusively and refer to any deviation from the normal structure or function of any part, organ or system of the body (or any combination thereof). A specific disease is manifested by characteristic symptoms and signs, including biological, chemical and physical changes, and is often associated with a variety of other factors including, but not limited to, demographic, environmental, employment, genetic and medically historical factors. Certain characteristic signs, symptoms, and related factors can be quantitated through a variety of methods to yield important diagnostic information.

The term "prophylactic" or "therapeutic" treatment refers to administration to the subject of one or more of the subject compositions. If it is administered prior to clinical manifestation of the unwanted condition (e.g., disease or other unwanted state of the host animal) then the treatment is prophylactic, i.e., it contributes to protection of the host against developing the unwanted condition, whereas if administered after manifestation of the unwanted condition, the treatment is therapeutic (i.e., it is intended to diminish, ameliorate or prevent progression of the unwanted condition or side effects therefrom).

The term "therapeutic effect" refers to a local or systemic effect in animals, particularly mammals, and more particularly humans, caused by a pharmacologically active substance. The term thus means any substance intended for use in the diagnosis, cure, mitigation, treatment or prevention of disease or in the enhancement of desirable physical or mental development and conditions in an animal or human. The phrase "therapeutically-effective amount" means that amount of such a substance that produces some desired local or systemic effect at a reasonable benefit/risk ratio applicable to any treatment. In certain embodiments, a therapeutically-effective amount of a compound will depend on its therapeutic index, solubility, and the like. For example, certain compounds discovered by the methods of the present invention may be administered in a sufficient amount to produce a reasonable benefit/risk ratio applicable to such treatment.

The term "effective amount" refers to the amount of a therapeutic reagent that when administered to a subject by an appropriate dose and regimen produces the desired result.

The term "subject in need of treatment for a disorder" is a subject diagnosed with that disorder, likely to develop the disorder, or is suspected of having that disorder.

The term "antibody" as used herein is intended to include whole antibodies, e.g., of any isotype (IgG, IgA, IgM, IgE, etc), and includes fragments thereof which are also specifically reactive with a vertebrate, e.g., mammalian, protein. Antibodies can be fragmented using conventional techniques and the fragments screened for utility and/or interaction with a specific epitope of interest. Thus, the term includes segments of proteolytically-cleaved or recombinantly-prepared portions of an antibody molecule that are capable of selectively reacting with a certain protein. Non-limiting examples of such proteolytic and/or recombinant fragments include Fab, F(ab')2, Fab', Fv, and single chain antibodies (scFv) containing a V[L] and/or V[H] domain joined by a peptide linker. The scFv's may be covalently or non-covalently linked to form antibodies having two or more binding sites. The term antibody also includes polyclonal, monoclonal, or other purified preparations of antibodies and recombinant antibodies.

The term "central tolerance" means tolerance for an antigen controlled by the events in the thymus, namely the clonal deletion of T cells reactive to the antigen in the thymus gland. Partially activated T cells with high affinity receptors for the antigen undergo negative selection and clonal deletion in the thymus by Fas-mediated apoptosis, triggered by coexpression and binding of FasL to Fas on the cell surface. In contrast, the term "peripheral tolerance" means deletion of T cells by activation-induced cell death (AICD) and functional silencing (clonal anergy) of T cells without clonal deletion in the spleen. Also, when lacking the cooperation of helper T cells, B cells are presumably "helpless" to respond to T cell dependent antigens. The modulation of central and peripheral tolerance is regulated by phosphorylation of $p56^{lck}$ and ZAP-70. The status and the degree of phosphorylation of key residues of these proteins result in up or down regulation of signaling molecules that influence the peripheral and central tolerance. Inhibition of T cell receptor signaling also plays a role in inducing tolerance.

Other technical terms used herein have their ordinary meaning in the art that they are used, as exemplified by a variety of technical dictionaries.

III. Random Copolymers

The composition of a random copolymer of the instant invention comprises the characteristics of a compilation of a multiplicity of cross-reactive T cell epitopes. The composition of a random copolymer of the instant invention may further comprise the characteristics of altered peptide ligands. Multiple functional consequences of the composition of a random copolymer of the instant invention exist: one is the potential to functionally interact with thousands, preferably hundreds of thousands, more preferably millions, of T cell epitopes via presentation by MHC molecules, preferably MHC class II molecules, while another is the generation of random copolymer specific T cells which may secrete soluble mediators, such as cytokines.

A random copolymer of the instant invention may be given specific amino acid sequence characteristics such that the selected sub-group of amino acids preferentially interacts with specific T cell epitopes, some of which may be directly associated with pathogenic disorders. Preferably, a random copolymer of the instant invention may be given specific amino acid sequence characteristics such that the selected sub-group of amino acids comprises between two and eight amino acids which preferentially interact with specific T cell epitopes some of which may be directly associated with pathogenic disorders which are exacerbated by aberrant production of soluble mediators, such as cytokines.

Preferably, a random copolymer of the instant invention may be given specific amino acid sequence characteristics such that the selected sub-group of amino acids comprises between two and eight amino acids which by virtue of the amino acids chosen and the ratio of said amino acids to one another preferentially interact with specific T cell epitopes some of which may be directly associated with pathogenic disorders which are exacerbated by aberrant production of soluble mediators, such as cytokines said pathogenic disorders having linkage to specific MHC class II alleles such as HLA-DR, or HLA-DQ.

More preferably, a random copolymer of the instant invention comprises a polymer of from two to eight amino acids randomly connected, preferably via peptide bonds which preferentially interacts with specific T cell epitopes some of which may be directly associated with pathogenic disorders which are exacerbated by aberrant production of soluble mediators, such as cytokines, said pathogenic disorders having linkage to specific MHC class II alleles such as HLA-DR, or HLA-DQ.

More preferably, a random copolymer of the instant invention comprises a polymer of from three to five amino acids randomly connected, preferably via peptide bonds which preferentially interacts with specific T cell epitopes some of which may be directly associated with pathogenic disorders which are exacerbated by aberrant production of soluble mediators, such as cytokines, said autoimmune disorders having linkage to specific MHC class II alleles such as HLA-DR, or HLA-DQ.

The random copolymers of the present invention may comprise a suitable quantity of an amino acid of positive electrical charge, such as lysine or arginine, in combination with an amino acid with a negative electrical charge (preferably in a lesser quantity), such as glutamic acid or aspartic acid, optionally in combination with an electrically neutral amino acid such as alanine or glycine, serving as a filler, and optionally with an amino acid adapted to confer on the copolymer immunogenic properties, such as an aromatic amino acid like tyrosine or tryptophan. Such compositions may include any of those disclosed in WO 00/005250, the entire contents of which being hereby incorporated herein by reference.

Copolymers Comprising Four Amino Acids

In one embodiment of the invention, the random copolymer contains four different amino acids, each from a different one of the following groups: (a) lysine and arginine; (b) glutamic acid and aspartic acid; (c) alanine and glycine; (d) tyrosine and tryptophan.

A specific copolymer according to this embodiment of the present invention comprises in combination alanine, glutamic acid, lysine, and tyrosine, and has a net overall positive electrical charge. One preferred example is YEAK, also referred to as Copolymer 1 (Cop 1) or glatiramer acetate, of average molecular weight about 4,700 to about 13,000 daltons. A preferred copolymer has a molecular weight of about 2,000 to about 40,000 daltons, or from about 2,000 to about 13,000 daltons. Preferred molecular weight ranges and processes for making a preferred form of Copolymer 1 are described in U.S. Pat. No. 5,800,808, the entire contents of which are hereby incorporated in the entirety. Thus, the copolymer may be a polypeptide from about 15 to about 100, preferably from about 40 to about 80, amino acids in length. In a preferred embodiment, the length of Copolymer 1 is between 35 and 75 amino acids residues. More preferably, the length of Copolymer 1 is between 35 and 65 amino acid residues. In a preferred embodiment the length of Copolymer 1 is about 50 amino acids. In another preferred embodiment, the length of Copolymer 1 is about 52 amino acids. In a preferred embodiment, Copolymer 1 has an average molar output ratio of about 1.0:2.0:6.0:5.0 for Y:E:A:K respectively, synthesized by solid phase chemistry as described below in more detail. The variability in the output ratios comprises a range of about 10% between the different amino acids.

In a preferred embodiment of Copolymer 1 of about 52 amino acid residues, the ratio of alanine composition in amino acid positions 31-52 is greater than in amino acid positions 11-30, and the ratio of alanine composition in amino acid positions 11-30 is greater than in amino acid positions 1-10. More specifically, a preferred embodiment of the invention is a random copolymer of the composition YEAK (L-tyrosine, L-glutamate, L-alanine and L-lysine) in an average molar output ratio of about 1.0:2.0:6.0:5.0 respectively, synthesized by solid phase chemistry, wherein the copolymer has a length of 52 amino acids, and wherein residues 1-10 of the copolymer sequence has a molar output ratio of about 1.0:2.0:5.5:5.0, residues 11-30 have a molar output ratio of about 1.0:2.0:6.0:5.0, and residues 31-52 have a molar output ratio of about 1.0:2.0:6.5:5.0.

For the purpose of the present invention, "Cop 1 or a Cop 1-related peptide or polypeptide" is intended to include any peptide or polypeptide, including a random copolymer, that cross-reacts functionally with myelin basic protein (MBP) and is able to compete with MBP on the MHC class II in the antigen presentation. Copolymer 1 has been approved in several countries for the treatment of multiple sclerosis (MS) under the trade name, COPAXONE™. COPAXONE™ is a trademark of Teva Pharmaceuticals Ltd., Petah Tikva, Israel. Copolymer 1 binds with high affinity and in a peptide-specific manner to purified MS-associated HLA-DR2 (DRB1*1501) and rheumatoid arthritis (RA)-associated HLA-DR1 (DRBI*0101) or HLA-DR4 (DRB1*0401) molecules. Since Copolymer 1 is a mixture of random polypeptides, it may contain different sequences that bind to different HLA proteins; in this case only a fraction out of the whole mixture would be an "active component." Alternatively, the whole mixture may be competent, i.e. all polypeptides binding to any HLA-DR molecule.

More preferably, a random copolymer of the instant invention comprises a polymer of the amino acids Copolymer 1 or YFAK randomly connected via peptide bonds which preferentially interacts with specific T cell epitopes associated with autoimmune disorders which are exacerbated by aberrant production inflammatory cytokines, said autoimmune disorders having linkage to specific MHC class II alleles such as HLA-DR, or HLA-DQ.

More preferably, a random copolymer of the instant invention comprises a polymer of the amino acids Copolymer 1 or YFAK randomly connected via peptide bonds which preferentially interacts with specific T cell epitopes associated with rheumatoid arthritis, multiple sclerosis, diabetes, celiac disease, rheumatoid arthritis, steroid sensitive nephrotic syndrome, mesengial IgA nephropathy, narcolepsy, neurological multiple sclerosis, relapsive polychondritis, dermatological disorders such as dermatitis herpetiformis, atopic dermatitis, Behcet's disease, pemphigus, psoriasis, primary Sjögren's syndrome, systemic vasculitides, erythematosus, gastrointestinal disorders such as Crohn's disease, respiratory disorders such as Sommer type hypersensitivity pneumonitis, and autoimmune thyroid disease (AITD).

In another aspect of the invention, the random copolymer comprises YFAK, VYAK, VWAK, VEAK and FEAK. In a preferred embodiment, the random copolymer consists of amino acid residues YFAK (L-tyrosine, L-phenylalanine, L-alanine and L-lysine) in an molar output ratio of about 1.0:1.2:$X_A$:6.0 respectively, wherein $X_A$ is greater than 11.0 and less than 30.0, and the variability in the output ratios comprises a range of about 10% between the different amino acids. In another preferred embodiment, the random copolymer consists of amino acid residues YFAK in a molar output ratio of about 1.0:1.0:$X_A$:6.0 respectively, wherein $X_A$ is greater than 5.0 and less than 15.0, and the variability in the output ratios comprises a range of about 10% between different amino acids. The molar output ratios of YFAK of random copolymers of the preferred embodiments are shown in Table I below:

TABLE I

Amino Acid Composition Ratios of Random Copolymers

| Y | F | A | K |
|---|---|---|---|
| 1.0: | 1.2: | 11.0 < 30.0: | 6.0 |
| 1.0: | 1.2: | 16.0: | 6.0 |
| 1.0: | 1.2: | 18.0: | 4.0 |
| 1.0: | 1.2: | 18.0: | 5.0 |
| 1.0: | 1.2: | 18.0: | 6.0 |
| 1.0: | 1.2: | 18.0: | 7.0 |
| 1.0: | 1.2: | 18.0: | 8.0 |
| 1.0: | 1.2: | 20.0: | 4.0 |
| 1.0: | 1.2: | 20.0: | 5.0 |
| 1.0: | 1.2: | 20.0: | 6.0 |
| 1.0: | 1.2: | 20.0: | 7.0 |
| 1.0: | 1.2: | 20.0: | 8.0 |
| 1.0: | 1.2: | 22.0: | 6.0 |
| 1.0: | 1.2: | 24.0: | 6.0 |
| (Y + F = 2.2): | | 18.0: | 6.0 |
| 0.66: | 1.54: | 18.0: | 6.0 |
| 0.88: | 1.32: | 18.0: | 6.0 |
| 1.1: | 1.1: | 18.0: | 6.0 |
| 1.32: | 0.88: | 18.0: | 6.0 |
| 1.54: | 0.66: | 18.0: | 6.0 |
| 1.0: | 1.0: | 5.0 < 15.0: | 6.0 |
| 1.0: | 1.0: | 10.0: | 6.0 |

In a preferred embodiment, the length of any of such copolymer is between 35 and 75 amino acids residues. More preferably, the length of a random copolymer is between 35 and 65 amino acid residues. In a preferred embodiment the length of a random copolymer is about 50 amino acids. In another preferred embodiment, the length of a random copolymer is about 52 amino acids.

A preferred embodiment of the invention is a random copolymer of the composition YFAK in an average molar output ratio of about 1.0:1.2:18.0:6.0 respectively, synthesized by solid phase chemistry as described below in more detail.

In a preferred embodiment, the average molar output ratio of YFAK is about 1.0:1.2:$X_A$:6.0, wherein $X_A$ is greater than 18, and the ratio of alanine increases with the length of copolymer. In a preferred embodiment, the length of such random copolymer is about 52 amino acid residues, and the ratio of alanine composition in amino acid positions 31-52 is greater than in amino acid positions 11-30, and the ratio of alanine composition in amino acid positions 11-30 is greater than in amino acid positions 1-10. More specifically, a preferred embodiment of the invention is a random copolymer of the composition YFAK (L-tyrosine, L-phenylalanine, L-alanine and L-lysine) in an average molar output ratio of about 1.0:1.2:18.0:6.0 respectively, synthesized by solid phase chemistry, wherein the copolymer has a length of 52 amino acids, and wherein residues 1-10 of the copolymer sequence has a molar output ratio of about 1.0:1.2:16:6, residues 11-30 have a molar output ratio of about 1.0:1.2:18:6, and residues 31-52 have a molar output ratio of about 1.0:1.2:20:6.

Copolymers Comprising Three Amino Acids

In another embodiment, the random copolymer contains three different amino acids each from a different one of three groups of the above mentioned groups (a) to (d). These copolymers are herein referred to as "terpolymers." The average molecular weight is between 2,000 to about 40,000 daltons, and preferably between about 3,000 to about 35,000 daltons. In a more preferred embodiment, the average molecular weight is about 5,000 to about 25,000 daltons.

In one embodiment, the terpolymers for use in the present invention contain tyrosine, alanine, and lysine, hereinafter designated YAK. The average molar fraction of the amino acids in these terpolymers can vary. For example, tyrosine can be present in a mole fraction of about 0.005 to about 0.250; alanine can be present in a mole fraction of about 0.3 to about 0.6; and lysine can be present in a mole fraction of about 0.1 to about 0.5. It is possible to substitute arginine for lysine, glycine for alanine, and/or tryptophan for tyrosine. The molar ratio of the monomers of the more preferred terpolymer of tyrosine, alanine and lysine, or YAK, is about 0.10 to about 0.54 to about 0.35. Exemplary YAK copolymers are described in Fridkis-Hareli M., *Hum Immunol.* 2000; 61(7): 640-50.

In another embodiment, the terpolymers for use in the present invention contain tyrosine, glutamic acid, and lysine, hereinafter designated YEK. The average molar fraction of the amino acids in these terpolymers can vary: glutamic acid can be present in a mole fraction of about 0.005 to about 0.300, tyrosine can be present in a mole fraction of about 0.005 to about 0.250, and lysine can be present in a mole fraction of about 0.3 to about 0.7. It is possible to substitute aspartic acid for glutamic acid, arginine for lysine, and/or tryptophan for tyrosine. The molar ratios of the monomers of the more preferred terpolymer of glutamic acid, tyrosine, and lysine, or YEK, is about 0.26 to about 0.16 to about 0.58.

In another embodiment the terpolymers for use in the present invention contain lysine, glutamic acid, and alanine, hereinafter designated KEA. The average molar fraction of the amino acids in these polypeptides can also vary. For example, glutamic acid can be present in a mole fraction of about 0.005 to about 0.300, alanine can be present in a mole fraction of about 0.005 to about 0.600, and lysine can be present in a mole fraction of about 0.2 to about 0.7. It is possible to substitute aspartic acid for glutamic acid, glycine for alanine, and/or arginine for lysine. The molar ratios of the monomers of the more preferred terpolymer of glutamic acid, alanine and lysine, or KEA, is about 0.15 to about 0.48 to about 0.36.

In another embodiment, the terpolymers for use in the present invention contain tyrosine, glutamic acid, and alanine, hereinafter designated YEA. The average molar fraction of the amino acids in these polypeptides can vary. For example, tyrosine can be present in a mole fraction of about 0.005 to about 0.250, glutamic acid can be present in a mole fraction of about 0.005 to about 0.300, and alanine can be present in a mole fraction of about 0.005 to about 0.800. It is possible to substitute tryptophan for tyrosine, aspartic acid for glutamic acid, and/or glycine for alanine. The molar ratios of the monomers of the more preferred terpolymer of glutamic acid, alanine, and tyrosine, or YEA, is about 0.21 to about 0.65 to about 0.14.

In a more preferred embodiment, the molar fraction of amino acids of the terpolymers is about what is preferred for Copolymer 1. The mole fraction of amino acids in Copolymer 1 is glutamic acid about 0.14, alanine about 0.43, tyrosine about 0.10, and lysine about 0.34. The most preferred average molecular weight for Copolymer 1 is between about 5,000 and about 9,000 daltons. The activity of Copolymer 1 for the utilities disclosed herein is expected to remain if one or more of the following substitutions is made: aspartic acid (D) for glutamic acid (E), glycine (G) for alanine (A), arginine (R) for lysine (K), and tryptophan (W) for tyrosine (Y).

Copolymers that Bind to MHC Class II Proteins

In one embodiment, the copolymers used in the methods described herein are capable of binding to an MHC class II protein which, preferably, is associated with an autoimmune disease. There are at least three types of Class II MHC molecules: HLA-DR, HLA-DQ, and HLA-DP molecules. There are also numerous alleles encoding each type of these HLA molecules. The Class II MHC molecules are expressed predominantly on the surfaces of B lymphocytes and antigen presenting cells such as macrophages. Any available method can be used to ascertain whether the copolymer binds to one or more MHC class II proteins. For example, the polypeptide can be labeled with a reporter molecule (such as a radionuclide or biotin), mixed with a crude or pure preparation of MHC class II protein and binding is detected if the reporter molecule adheres to the MHC class II protein after removal of the unbound polypeptide.

In another embodiment, the copolymers used in the methods described herein are capable of binding to an MHC class II protein associated with multiple sclerosis. A polypeptide of this embodiment can have similar or greater affinity for the antigen binding groove of an MHC class II protein associated with multiple sclerosis than does Copolymer 1. Hence, the contemplated polypeptide can inhibit binding of or displace the binding of myelin autoantigens from the MHC class II protein. One MHC class II protein associated with multiple sclerosis is HLA-DR4 (DRB1*1501).

In another embodiment, the random copolymers used in the methods described herein are capable of binding to an MHC class II protein associated with an arthritic condition, for example, rheumatoid arthritis or osteoarthritis. A random copolymer of this embodiment can have a greater affinity for the antigen binding groove of an MHC class II protein associated with the autoimmune disease than does a type II collagen 261-273 peptide. Hence, the contemplated Copolymer 1 or a random copolymer described herein such as YFAK can inhibit binding of or displace the type II collagen 261-273 peptide from the antigen binding groove of an MHC class II protein. The Class II MHC protein consists of approximately equal-sized alpha and beta subunits, both of which are transmembrane proteins. A peptide-binding cleft is formed by parts of the amino termini of both α and β subunits. This peptide-binding cleft is the site of presentation of the antigen to T cells.

In other embodiments, the random copolymers used in the invention can bind to the peptide binding groove of the HLA-DR molecules. As binding motifs of Cop 1 to MS-associated HLA-DR molecules are known (Fridkis-Hareli et al, 1999, *J. Immunol.*; 162(8):4697-704), polypeptides of fixed sequence can be readily prepared and tested for binding to the peptide binding groove of the HLA-DR molecules as described in Fridkis-Hareli. Examples of such peptides are those disclosed in WO 00/005249, the entire contents of which being hereby incorporated herein by reference. Thirty-two of the peptides specifically disclosed in said application are as follows:

| | |
|---|---|
| AAAYAAAAAAKAAAA | (SEQ. ID NO: 1) |
| AEKYAAAAAAKAAAA | (SEQ. ID NO: 2) |
| AKEYAAAAAAKAAAA | (SEQ. ID NO: 3) |
| AKKYAAAAAAKAAAA | (SEQ. ID NO: 4) |
| AEAYAAAAAAKAAAA | (SEQ. ID NO: 5) |
| KEAYAAAAAAKAAAA | (SEQ. ID NO: 6) |
| AEEYAAAAAAKAAAA | (SEQ. ID NO: 7) |
| AAEYAAAAAAKAAAA | (SEQ. ID NO: 8) |
| EKAYAAAAAAKAAAA | (SEQ. ID NO: 9) |
| AAKYEAAAAAKAAAA | (SEQ. ID NO: 10) |
| AAKYAEAAAAKAAAA | (SEQ. ID NO: 11) |
| EAAYAAAAAAKAAAA | (SEQ. ID NO: 12) |
| EKKYAAAAAAKAAAA | (SEQ. ID NO: 13) |
| EAKYAAAAAAKAAAA | (SEQ. ID NO: 14) |
| AEKYAAAAAAAAAA | (SEQ. ID NO: 15) |
| AKEYAAAAAAAAAA | (SEQ. ID NO: 16) |
| AKKYEAAAAAAAAA | (SEQ. ID NO: 17) |
| AKKYAEAAAAAAAA | (SEQ. ID NO: 18) |
| AEAYKAAAAAAAAA | (SEQ. ID NO: 19) |
| KEAYAAAAAAAAAA | (SEQ. ID NO: 20) |
| AEEYKAAAAAAAAA | (SEQ. ID NO: 21) |
| AAEYKAAAAAAAAA | (SEQ. ID NO: 22) |
| EKAYAAAAAAAAAA | (SEQ. ID NO: 23) |
| AAKYEAAAAAAAAA | (SEQ. ID NO: 24) |
| AAKYAEAAAAAAAA | (SEQ. ID NO: 25) |
| EKKYAAAAAAAAAA | (SEQ. ID NO: 26) |
| EAKYAAAAAAAAAA | (SEQ. ID NO: 27) |
| AEYAKAAAAAAAAA | (SEQ. ID NO: 28) |
| AEKAYAAAAAAAAA | (SEQ. ID NO: 29) |
| EKYAAAAAAAAAAA | (SEQ. ID NO: 30) |
| AYKAEAAAAAAAAA | (SEQ. ID NO: 31) |
| AKYAEAAAAAAAAA. | (SEQ. ID NO: 32) |

Additional random copolymers for use in the present invention, and methods of synthesizing them, may be found in the literature, such as in Shukaliak Quandt, J. et al., 2004, *Mol. Immunol.* 40(14-15):1075-87; Montaudo, M. S., 2004, *J. Am. Soc. Mass Spectrom.* 15(3):374-84; Takeda, N. et al., 2004, *J. Control Release* 95(2): 343-55; Pollino, J. M. et al., 2004, *J. Am. Chem. Soc.* 126(2):563-7; Fridkis-Hareli, M. et al., 2002, *J. Clin Invest.* 109(12):1635-43; Williams, D. M. et al., 2000, *J. Biol. Chem.* 275(49): 38127-30; Tselios, T. et al., 2000, *Bioorg. Med. Chem.* 8(8): 1903-9; and Cady, C. T. et al., 2000, *J. Immunol.* 165(4): 1790-8.

In one specific embodiment, the random copolymer comprises at least seven amino acid residues in length and is capable of binding to an MHC class II protein associated with an autoimmune disease, the synthetic peptide binding with greater affinity to the antigen binding groove of the MHC class II protein than a type II collagen 261-273 peptide, wherein the synthetic peptide comprises a sequence selected from the group consisting of alanine-glutamic acid-lysine-tyrosine-alanine (AEKYA) (SEQ ID NO:41), alanine-glutamic acid-lysine-valine-alanine (AEKVA) (SEQ ID NO:42), alanine-glutamic acid-lysine-phenylalanine-alanine (AEKFA) (SEQ ID NO:43), alanine-lysine-tyrosine-alanine-glutamic acid (AKYAE) (SEQ ID NO:44), glutamic acid-alanine-lysine-tyrosine-alanine (EAKYA) (SEQ ID NO:45), alanine-lysine-valine-alanine-glutamic acid (AKVAE) (SEQ ID NO:46), and glutamic acid-alanine-lysine-valine-alanine (EAKVA) (SEQ ID NO:47), alanine-lysine-phenylalanine-alanine-glutamic acid (AKFAE) (SEQ ID NO:48), and glutamic acid-alanine-lysine-phenylalanine-alanine (EAKFA) (SEQ ID NO:49).

In certain preferred embodiments, the copolymers of the invention bind to HLA-DQA1 molecules, and in even more preferably to one or more of HLA molecules encoded in the alleles DQA1*0501-DQB1*0201, DQA1*0301, DQB1*0401, and DQA1*03-DQB1*0302.

In other embodiments, the copolymers of the methods of the present invention bind to certain HLA-DQ molecules that predispose the carrier of such molecules to autoimmune-associated diseases, such as type I diabetes and celiac disease, with a dissociation constant ($K_d$) at least 10 times less than the copolymer's $K_d$ for binding HLA-DR molecules and/or other DQ isotypes. Such HLA-DQ molecules are the combined protein products of specific HLA-DQB1 and DQA1 alleles known as DQB1*0201, DQB1*0302, DQB1*0304, DQB1*0401, DQB1*0501, DQB1*0502; and DQA1*0301, DQA1*0302, DQA1*0303, DQA1*0501. These alleles may be encoded on the same haplotypes ("cis" alleles) such as DQB1*0201-DQA1*0501-DRB1*0301 and DQB1*0302-DQA1*0301-DRB1*0401. The resulting HLA molecule comprising polypeptide products of "cis" alleles are herein referred to as "cis dimer." Alternatively, the alleles may be encoded on different haplotypes ("trans" alleles). The HLA molecule comprising polypeptide products of "trans" alleles are herein referred to as "trans" dimer. An example of "trans" alleles is the combination of DQB1*0201 on DQB1*0201-DQA1*0501-DRB1*0301 and DQA1*0301 on DQB1*0301-DQA1*0301-DRB1*0404.

In certain embodiments, the DQ-directed copolymers used in the methods described herein are a mixture of randomized or partially randomized amino acid sequence containing amino acids from each of the following four groups: (1) hydrophobic, aliphatic amino acids (such as leucine, isoleucine, valine, methionine); (2) amino acids with acidic side chains (such as aspartic acid, glutamic acid); (3) amino acids with small hydrophilic side chains (such as serine, cysteine, threonine); and (4) amino acids with small aliphatic side chains (such as alanine, glycine); additionally, the copolymer contains proline residues. In one embodiment, the copolymer is derived using the amino acids Glutamine (E) and/or Aspartic acid (D), Leucine (L), Serine (S) and Alanine (A), and is referred to herein as an "ELSA" copolymer.

In certain other embodiments, the DQ-directed copolymers are a mixture of randomized or partially randomized amino acid sequence containing amino acids from each of the following four groups: (1) hydrophobic, aliphatic amino acids (such as leucine, isoleucine, valine, methionine); (2) bulky hydrophobic amino acids (such as tyrosine, phenylalanine, leucine, methionine); (2) amino acids with acidic side chains (such as aspartic acid, glutamic acid); (3) amino acids with small hydrophilic side chains (such as serine, cysteine, threonine); and (4) amino acids with small aliphatic side chains (such as alanine, glycine); additionally, the copolymer contains proline residues. An exemplary copolymer is derived using the amino acid residues Glutamine (E) and/or Aspartic acid (D), Leucine (L), Tyrosine (Y) and Val (V), and is referred to herein as an "DLYV" copolymer.

In one embodiment, a method of treatment of an autoimmune disease comprises administration of a copolymer that binds to an HLA-DQ molecule associated with the autoimmune disease. Preferably, the method of treatment is carried out using a copolymer that comprises a polypeptide comprising a plurality of amino acid residues selected from: (1) a hydrophobic, aliphatic residue (leucine, isoleucine, valine, methionine); (2) an acidic residue (aspartic acid, glutamic acid); (3) a small hydrophilic residue (serine, cysteine, threonine); (4) a small aliphatic residue (alanine, glycine); and (5) proline.

In preferred embodiments, the copolymers compositions of the present invention bind to one or more DQ isotypes with an average $K_d$ of 1 µM or less, and more preferably an average $K_d$ less than 100 nM, 10 nM or even 1 nM. Another way to identify preferred copolymers is based on the measure of a copolymer to displace another in competitive binding assays, such as described in Sidney et al., 2002, *J. Immunol.* 169: 5098, which is expressed as an $IC_{50}$ value. Preferred copolymers of the present invention have $IC_{50}$'s less than 1 µM, more preferably less than 500 nM, and even more less than 100 nM.

In certain preferred embodiments, the copolymer is formed by random synthesis (polymerization) of the various amino acid residues. A certain ratio of amino acids to be incorporated into the random copolymer may be used. Preferred random copolymers of the present invention comprise amino acid residues K, E, A, S, V, and P. More preferably, the ratio of K:E:A:S:V is 0.3:0.7:9:0.5:0.5:0.3. Preferably, the random copolymers are about 10 to 100 amino acid residues long, more preferably 20 to 80 amino acid residues long, even more preferably 40 to 60 amino acid residues long, and most preferably about 50 amino acid residues long. When synthesized, a typical preparation of random copolymers is a mixture of peptides of various lengths, the majority of which are of the desired length but containing shorter or longer peptides inevitably created by the currently available synthetic processes.

Further, in certain embodiments, the copolymer can be a semi-random (or semi-regular) polymer having "anchor," or fixed, residues which occur with regular spacing in the resulting polymer, providing for optimal class II binding. The anchor residues within the peptide may be E, D, or V. For example, the copolymer can be synthesized to have one of the general sequences:

```
1. [XXEXXXXXXXEXX]_n       (SEQ. ID NO: 33)

2. [XXEXXXXXXXDXX]_n       (SEQ. ID NO. 34)

3. [XXDXXXXXXXDXX]_n       (SEQ. ID NO. 35)

4. [XXDXXXXXXXEXX]_n       (SEQ. ID NO. 36)

5. [XXEXXVXXXXDXX]_n       (SEQ. ID NO. 37)

6. [XXDXXVXXXXDXX]_n       (SEQ. ID NO. 38)

7. [XXDXXVXXXXEXX]_n       (SEQ. ID NO. 39)

8. [XXEXXVXXXXEXX]_n       (SEQ. ID NO. 40)
wherein X is A, S, V, K, or P, the ratio of which
are 5:1:1:1:0.5, and 1 ≤ n ≤ 8.
```

The peptides may have a length of 9 to 25 amino acid residues. Preferably, the peptide is 13 amino acid-residues long. A peptide of a defined sequence length of 9 to 25 amino acids may contain from 2 to 20 fixed residues. An individual fixed residue of a peptide described in this invention may bind to the peptide binding grove of a class II MCH molecule at any of the positions P1, P4, P7, or P9. Preferably, such peptide contains 2 or 3 fixed residues. In one embodiment, a peptide of a defined sequence length of 13 amino acids will contain 2 fixed residues, either E or D or any combination thereof. Preferably a peptide of a defined sequence length of 13 amino acids will contain 3 fixed residues. The peptides may be multimers of a defined sequence, wherein the number of the repeating units preferably ranges from 2 to 8. More preferably, the number of the repeating units is 3 to 6. Most preferably, the number of repeating units is 4. In a preferred embodiment, a multimer of the instant invention comprises a peptide of a defined sequence length of 13 amino acids containing 2 fixed residues, either E or D or any combination thereof.

In certain preferred embodiments, the subject copolymers are formulated for use as a medicament so as to have a polydispersity less than 25,000, and more preferably less than 10000, 5000, 1000, 500, 100, 50, or even less than 10.

Synthesis of Random Copolymers

The terpolymers and random copolymers used in the present invention can be made by any procedure available to one of skill in the art. For example, the terpolymers can be made under condensation conditions using the desired molar ratio of amino acids in solution, or by solid phase synthetic procedures. Condensation conditions include the proper temperature, pH, and solvent conditions for condensing the carboxyl group of one amino acid with the amino group of another amino acid to form a peptide bond. Condensing agents, for example dicyclohexyl-carbodiimide, can be used to facilitate the formation of the peptide bond. Blocking groups can be used to protect functional groups, such as the side chain moieties and some of the amino or carboxyl groups against undesired side reactions.

For example, the process disclosed in U.S. Pat. No. 3,849,550, can be used wherein the N-carboxyanhydrides of tyrosine, alanine, γ-benzyl glutamate and N-ϵ-trifluoroacetyl-lysine are polymerized at ambient temperatures in anhydrous dioxane with diethylamine as an initiator. The γ-carboxyl group of the glutamic acid can be deblocked by hydrogen bromide in glacial acetic acid. The trifluoroacetyl groups are removed from lysine by 1 molar piperidine. One of skill in the art readily understands that the process can be adjusted to make peptides and polypeptides containing the desired amino acids, that is, three of the four amino acids in Copolymer 1, by selectively eliminating the reactions that relate to any one of glutamic acid, alanine, tyrosine, or lysine. For purposes of this application, the terms "ambient temperature" and "room temperature" mean a temperature ranging from about 20 to about 26° C.

A preferred synthesis method of the random copolymers of the present invention is by solid phase synthesis. The synthesis is done in multiple steps by the Solid Phase Peptide Synthesis (SPPS) approach using Fmoc protected amino acids. SPPS is based on sequential addition of protected amino acid derivatives, with side chain protection where appropriate, to a polymeric support (bead). The base-labile Fmoc group is used for N-protection. After removing the protecting group (via piperidine hydrolysis) the next amino acid mixture is added using a coupling reagent (TBTU). After the final amino acid is coupled, the N-terminus is acetylated.

The resulting peptide (attached to the polymeric support through its C-terminus) is cleaved with TFA to yield the crude peptide. During this cleavage step, all of the side chains protecting groups are also cleaved. After precipitation with diisopropyl ether, the solid is filtered and dried. The resulting peptide is analyzed and stored at 2-8° C.

Example of Solid Phase Synthesis

The random copolymer YFAK consisting of L-alanine, L-lysine, L-phenylalanine and L-tyrosine is prepared in its protected form on Wang resin. Resins used were Fmoc-L-Tyr (t-Bu)-Wang (0.62 mmol/g), Fmoc-L-Phe-Wang (0.72 mmol/g), Fmoc-L-Ala-Wang (0.70 mmol/g), and Fmoc-L-Lys (Boc)-Wang (0.72 mmol/g). The four F-moc protected amino acids, Fmoc-L-Tyr(t-Bu)-OH, Fmoc-L-Phe-OH, Fmoc-L-Ala-OH, and Fmoc-L-Lys-OH, are used in a molar input ratio of 1:1:10:6 respectively during each coupling step. Other reagents used in the synthesis are 2-(1H-Benzotriazole-1-yl)-1,1,3,3-tetramethyluronium, tetrafluoroborate (TBTU), N,N-diisopropylethylamine (DIPEA), piperidine, and trifluoroacetic acid (TFA). The solvents used are N-methylpyrrolidone (NMP), isopropanol (IsOH, IPA, i-PrOH), methylene chloride, and isopropyl ether. The stoichiometry of each coupling is as follows:

residues 1 through 10 using 2 equivalents of Fmoc protected amino acids;

residues 11 through 30 using 2 equivalents with double coupling of Fmoc protected amino acids;

residues 31 through 52 using 2.5 equivalents of Fmoc protected amino acids with double coupling.

An example of amino acid input ratios in a representative example of YFAK synthesis with progressively higher alanine contents is as follows:

| Positions | Y | F | A | K |
|---|---|---|---|---|
| 0-10 | 3.7 | 5.5 | 64.4 | 26.4 |
| 11-20 | 4.3 | 5.1 | 71.4 | 19.2 |
| 21-30 | 4.0 | 4.7 | 71.5 | 19.8 |
| 31-40 | 3.6 | 4.7 | 74.3 | 17.4 |
| 41-52 | 3.0 | 4.1 | 76.0 | 16.8 |

In a similar manner, Copolymer 1, a random copolymer of a preferred embodiment of the invention, is prepared in its protected form on Wang resin. Resins used were Fmoc-L-Tyr (t-Bu)-Wang (0.62 mmol/g), Fmoc-L-Glu-Wang, Fmoc-L-Ala-Wang (0.70 mmol/g), and Fmoc-L-Lys(Boc)-Wang (0.72 mmol/g). The four F-moc protected amino acids, Fmoc-L-Tyr(t-Bu)-OH, Fmoc-L-Glu-OH, Fmoc-L-Ala-OH, and Fmoc-L-Lys-OH, are used in a molar input ratio of 1:2:6:5 respectively during each coupling step. Other reagents used and coupling stoichiometry is as with the synthesis of YFAK.

An example of amino acid input ratios in a representative example of YEAK synthesis with progressively higher alanine contents is as follows:

| Positions | Y | E | A | K |
|---|---|---|---|---|
| 0-10 | 3.7 | 9.1 | 21.4 | 22.0 |
| 11-20 | 4.3 | 8.5 | 23.8 | 16.0 |
| 21-30 | 4.0 | 8.0 | 23.9 | 16.5 |
| 31-40 | 3.6 | 7.8 | 24.8 | 14.5 |
| 41-52 | 3.0 | 6.8 | 25.3 | 14.0 |

Unnatural Polypeptides and Chemical Modification of Copolymers

In one embodiment, the copolymers of the present invention are composed of naturally-occurring amino acids. In other embodiments, the copolymers are comprised of naturally occurring and synthetic derivatives, for example, selenocysteine. Amino acids further include amino acid analogs. An amino acid "analog" is a chemically related form of the amino acid having a different configuration, for example, an isomer, or a D-configuration rather than an L-configuration, or an organic molecule with the approximate size and shape of the amino acid, or an amino acid with modification to the atoms that are involved in the peptide bond, so as to be protease resistant when polymerized in a polypeptide.

The copolymers for use in the present invention can be composed of L- or D-amino acids or mixtures thereof. As is known by those of skill in the art, L-amino acids occur in most natural proteins. However, D-amino acids are commercially available and can be substituted for some or all of the amino acids used to make the terpolymers and other copolymers of the present invention. The present invention contemplates copolymers containing both D- and L-amino acids, as well as copolymers consisting essentially of either L- or D-amino acids.

In certain embodiments, the random copolymers of the present invention include such linear copolymers that are further modified by substituting or appending different chemical moieties. In one embodiment, such modification is at a residue location and in an amount sufficient to inhibit proteolytic degradation of the copolymer in a subject. For example, the amino acid modification may be the presence in the sequence of at least one proline residue; the residue is present in at least one of carboxy- and amino termini; further, the proline can be present within four residues of at least one of the carboxy- and amino-termini. Further, the amino acid modification may be the presence of a D-amino acid.

In certain embodiments, the subject random copolymer is a peptidomimetic. Peptidomimetics are compounds based on, or derived from, peptides and proteins. The copolymer peptidomimetics of the present invention typically can be obtained by structural modification of one or more native amino acid residues, e.g., using unnatural amino acids, conformational restraints, isosteric replacement, and the like. The subject peptidomimetics constitute the continuum of structural space between peptides and non-peptide synthetic structures.

Such peptidomimetics can have such attributes as being non-hydrolyzable (e.g., increased stability against proteases or other physiological conditions which degrade the corresponding peptide copolymers), increased specificity and/or potency. For illustrative purposes, peptide analogs of the present invention can be generated using, for example, benzodiazepines (e.g., see Freidinger et al. in "Peptides: Chemistry and Biology," G. R. Marshall ed., ESCOM Publisher: Leiden, Netherlands, 1988), substituted gamma lactam rings (Garvey et al. in "Peptides: Chemistry and Biology," G. R. Marshall ed., ESCOM Publisher: Leiden, Netherlands, 1988, p 123), C-7 mimics (Huffman et al. in "Peptides: Chemistry and Biology," G. R. Marshall ed., ESCOM Publisher: Leiden, Netherlands, 1988, p. 105), keto-methylene pseudopeptides (Ewenson et al., 1986, *J. Med. Chem.* 29:295; and Ewenson et al. in "Peptides: Structure and Function (Proceedings of the 9th American Peptide Symposium)," Pierce Chemical Co. Rockland, Ill., 1985), β-turn dipeptide cores (Nagai et al., 1985, *Tetrahedron Lett.* 26:647; and Sato et al., 1986, *J. Chem. Soc. Perkin Trans.* 1:1231), β-aminoalcohols (Gordon et al., 1985, *Biochem. Biophys. Res. Commun.* 126:419; and Dann et al., 1986, *Biochem. Biophys. Res. Commun.* 134:71), diaminoketones (Natarajan et al., 1984, *Biochem. Biophys. Res. Commun.* 124:141), and methyleneamino-modified (Roark et al. in "Peptides: Chemistry and Biology," G. R. Marshall ed., ESCOM Publisher: Leiden, Netherlands, 1988, p 134). Also, see generally, Session III: Analytic and synthetic methods, in "Peptides: Chemistry and Biology," G. R. Marshall ed., ESCOM Publisher: Leiden, Netherlands, 1988)

The molecular weight of a random copolymer can be adjusted during polypeptide synthesis or after the copolymer have been synthesized. To adjust the molecular weight during polypeptide synthesis, the synthetic conditions or the amounts of amino acids are adjusted so that synthesis stops when the polypeptide reaches the approximate length which is desired. After synthesis, polypeptides with the desired molecular weight can be obtained by any available size selection procedure, such as chromatography of the polypeptides on a molecular weight sizing column or gel, and collection of the molecular weight ranges desired. The present polypeptides can also be partially hydrolyzed to remove high molecular weight species, for example, by acid or enzymatic hydrolysis, and then purified to remove the acid or enzymes.

In one embodiment, the random copolymers with a desired molecular weight may be prepared by a process which includes reacting a protected polypeptide with hydrobromic acid to form a trifluoroacetyl-polypeptide having the desired molecular weight profile. The reaction is performed for a time and at a temperature which is predetermined by one or more test reactions. During the test reaction, the time and temperature are varied and the molecular weight range of a given batch of test polypeptides is determined. The test conditions which provide the optimal molecular weight range for that batch of polypeptides are used for the batch. Thus, a trifluoroacetyl-polypeptide having the desired molecular weight profile can be produced by a process which includes reacting the protected polypeptide with hydrobromic acid for a time and at a temperature predetermined by test reaction. The trifluoroacetyl-polypeptide with the desired molecular weight profile is then further treated with an aqueous piperidine solution to form a low toxicity polypeptide having the desired molecular weight.

In one preferred embodiment, a test sample of protected polypeptide from a given batch is reacted with hydrobromic acid for about 10-50 hours at a temperature of about 20-28° C. The best conditions for that batch are determined by running several test reactions. For example, in one embodiment, the protected polypeptide is reacted with hydrobromic acid for about 17 hours at a temperature of about 26° C.

In some embodiments, random copolymers which may be used in the invention include those described in International PCT Publication Nos. WO 00/05250, WO 00/05249; WO 02/59143, WO 0027417, WO 96/32119, in U.S. Patent Publication Nos. 2004/003888, 2002/005546, 2003/0004099, 2003/0064915 and 2002/0037848, in U.S. Pat. Nos. 6,514,938, 5,800,808 and 5,858,964, and those described in PCT application PCT/US05/06822. These references further describe methods of synthesizing random copolymers, compositions comprising random copolymers, therapeutic formulations of random copolymers, methods of administering random copolymers to a subject, diseases that may be treated with random copolymers, and additional therapeutically effective agents which may be co-administered to a subject in with the random copolymers. The teachings of all these patents, applications and publications are herein incorporated by reference in their entirety.

It is clear that this is given by way of example only, and that the composition can be varied both with respect to the constituents and relative proportions of the constituents if the above general criteria are adhered to.

IV. Diseases

The invention provides methods for treating or preventing diseases in a subject. A subject who is at risk of developing a disease, who is suspected of being afflicted with a disease, or who is afflicted with the disease may be treated using the methods provided by the invention.

In one embodiment, the disease that may be treated with the methods of the present invention comprises a disease that is mediated by T-cells, and in particular $T_H1$ cells, or is a disease which is exacerbated by an excess of inflammatory cytokines. The methods of the present invention may be used to treat diseases comprising ischemic injuries, including those caused by systemic ischemia or local ischemia, particularly to the heart, lungs or kidneys. In some embodiments, the inflammation is associated with a septic shock, anaphylactic shock, toxic shock syndrome, cachexia, necrosis, gangrene, a prosthetic implant, or hypersensitivity, including Type I hypersensitivity, Type II hypersensitivity, Type III hypersensitivity, Type IV hypersensitivity, immediate hypersensitivity, antibody mediated hypersensitivity, immune complex mediated hypersensitivity, T lymphocyte mediated hypersensitivity and delayed type hypersensitivity. In other embodiments, the disease comprises myocardial infarction, cardiac arrest, ischemia-reperfusion injury, congestive heart failure, cardiotoxicity, cardiac damage due to parasitic infection, fulminant cardiac amyloidosis, heart surgery, heart transplantation, traumatic cardiac injury, surgical repair of a thoracic aortic aneurysm, a suprarenal aortic aneurysm, hemorrhagic shock due to blood loss, cardiogenic shock due to myocardial infarction or cardiac failure, anaphylaxis, unstable coronary syndrome, tachycardia, bradycardia or a combination thereof.

In one embodiment, the disease that may be treated with the methods of the present invention comprises autoimmune diseases. Autoimmune diseases contemplated by the present invention include either cell-mediated disease (e.g., T-cell) or antibody-mediated (e.g., B cell) disorders. Such disorders can be inter alia arthritic conditions, demyelinating diseases and inflammatory diseases. The methods of the invention are of particular interest for the treatment of demyelinating inflammatory diseases, which include multiple sclerosis, EAE, optic neuritis, acute transverse myelitis, and acute disseminated encephalitis. In one specific embodiment, any autoimmune disease can be treated by the present polypeptides so long as the contemplated polypeptide binds to an MHC class II protein that has been associated with the autoimmune disease. Progression of disease can be measured by monitoring clinical or diagnostic symptoms using known methods.

In one embodiment, the disease treated by the methods provided herein is an "arthritic condition". As used herein, an arthritic condition is a condition wherein at least one symptom of rheumatoid arthritis is observed in at least one joint of a mammal, for example in a shoulder, knee, hip, backbone or a digit of the mammal. RA is a common human autoimmune disease with a prevalence of about 1% among Caucasians (Harris, B. J. et al., 1997, In Textbook of Rheumatology 898-932), currently affecting 2.5 million Americans. RA is characterized by chronic inflammation of the synovial joints and infiltration by activated T cells, macrophages and plasma cells, leading to a progressive destruction of the articular cartilage. It is the most severe form of joint disease. Inherited susceptibility to RA is strongly associated with the affected subject having at the MHC class II DRB1 locus the allele DRB1*0401, DRB1*0404, or DRB1*0405 or the DRB1*0101 allele. The nature of the autoantigen(s) in RA is poorly understood, although collagen type II (CII) is a prominent candidate. An immunodominant T cell epitope in collagen type II corresponding to residues 261-273 has been identified (Fugger, L. et al., 1996, Eur. J. Immunol. 26: 928-933).

Other examples of arthritic conditions include "polyarthritis", which is an arthritic condition that affects more than a single joint; "juvenile arthritis", an arthritic condition of humans under the age of 21; and Felty's syndrome, which can include the symptoms of neutropenia, splenomegaly, weight loss, anemia, lymphadenopathy, and pigment spots on the skin.

In another embodiment, the disease treated by the methods provided herein is multiple sclerosis (MS). The course of disease for multiple sclerosis is highly varied, unpredictable, and, in most patients, remittent. The pathologic hallmark of MS is multicentric, multiphasic CNS inflammation and demyelination. Months or years of remission may separate episodes, particularly early in the disease. About 70% of patients of relapsing-remitting (RR) type, which is characterized by acute exacerbations with full or partial remissions. The remaining patients present with chronic progressive MS, which is subdivided further into (a) primary-progressive (PP), (b) relapsing-progressive (RP), which is a pattern combining features of RR and RP and is intermediate in clinical severity, and (c) secondary-progressive (SP), which many patients with RR progress to over time. In a specific preferred embodiment, the disease treated by the present method is relapsing-remitting multiple sclerosis.

Clinical symptoms of MS include sensory loss (paresthesias), motor (muscle cramping secondary to spasticity) and autonomic (bladder, bowel, sexual dysfunction) spinal cord symptoms; cerebellar symptoms (e.g., Charcot triad of dysarthna, ataxia, tremor); fatigue and dizziness; impairment in information processing on neuropsychological testing; eye symptoms, including diplopia on lateral gaze; trigeminal neuralgia; and optic neuritis.

The autoantigen in MS most likely is one of several myelin proteins (e.g, proteolipid protein (PLP); myelin oligodendrocyte glycoprotein (MOG); myelin basic protein (MBP); myelin-associated glycoprotein (MAG), myelin-associated oligodendrocytic basic protein (MBOP); citrulline-modified MBP (the C8 isoform of MBP in which 6 arginines have been de-iminated to citrulline), cyclic nucleotide phosphodiesterase (CNPase), alpha-B crystalline, etc.) The integral membrane protein PLP is a dominant autoantigen of myelin. Microglial cells and macrophages perform jointly as antigen-presenting cells, resulting in activation of cytokines, complement, and other modulators of the inflammatory process, targeting specific oligodendroglia cells and their membrane myelin. A quantitative increase in myelin-autoreactive $T_H1$ cells with the capacity to secrete IFN-γ is associated with the pathogenesis of MS and EAE, suggesting that autoimmune inducer/helper T lymphocytes in the peripheral blood of MS patients may initiate and/or regulate the demyelination process in patients with MS. On the other hand, there is an extended literature on the protective role of $T_H2$ cells producing anti-inflammatory cytokines such as IL-4 and IL-10. The shift of balance from $T_H1$ to $T_H2$ type of cells is expected to be beneficial to the prevention and treatment of MS and EAE.

In another embodiment, the disease treated by the methods provided herein is Insulin Dependent Diabetes Mellitus. Human type I or insulin-dependent diabetes mellitus (IDDM) is characterized by autoimmune destruction of the cells in the pancreatic islets of Langerhans. The depletion of β-cells results in an inability to regulate levels of glucose in the blood. Overt diabetes occurs when the level of glucose in the blood rises above a specific level, usually about 250 mg/dl. In humans a long pre-symptomatic period precedes the onset of diabetes. During this period there is a gradual loss of pancreatic beta cell function. The development of disease is implicated by the presence of autoantibodies against insulin, glutamic acid decarboxylase, and the tyrosine phosphatase IA2 (IA2), each an example of a self-protein, -polypeptide or -peptide according to this invention. Human IDDM is currently treated by monitoring blood glucose levels to guide injection, or pump-based delivery, of recombinant insulin. Diet and exercise regimens contribute to achieving adequate blood glucose control.

Markers that may be evaluated during the pre-symptomatic stage are the presence of insulitis in the pancreas, the level and frequency of islet cell antibodies, islet cell surface antibodies, aberrant expression of Class II MHC molecules on pancreatic beta cells, glucose concentration in the blood, and the plasma concentration of insulin. An increase in the number of T lymphocytes in the pancreas, islet cell antibodies and blood glucose is indicative of the disease, as is a decrease in insulin concentration.

The presence of combinations of autoantibodies with various specificities in serum is highly sensitive and specific for human type I diabetes mellitus. For example, the presence of autoantibodies against GAD and/or IA-2 is approximately 98% sensitive and 99% specific for identifying type I diabetes mellitus from control serum. In non-diabetic first degree relatives of type I diabetes patients, the presence of autoantibodies specific for two of the three autoantigens including GAD, insulin and IA-2 conveys a positive predictive value of >90% for development of type I DM within 5 years.

In another embodiment, the disease treated by the methods provided herein is autoimmune uveitis. Autoimmune uveitis is an autoimmune disease of the eye that is estimated to affect 400,000 people, with an incidence of 43,000 new cases per year in the U.S. Autoimmune uveitis is currently treated with steroids, immunosuppressive agents such as methotrexate and cyclosporin, intravenous immunoglobulin, and TNFα-antagonists.

In another embodiment, the disease treated by the methods provided herein is experimental autoimmune uveitis (EAU). EAU is a T cell-mediated autoimmune disease that targets neural retina, uvea, and related tissues in the eye. EAU shares many clinical and immunological features with human autoimmune uveitis, and is induced by peripheral administration of uveitogenic peptide emulsified in Complete Freund's Adjuvant (CFA).

In another embodiment, the disease treated by the methods provided herein is primary biliary cirrhosis (PBC). PBC is an organ-specific autoimmune disease that predominantly affects women between 40-60 years of age. The prevalence reported among this group approaches 1 per 1,000. PBC is characterized by progressive destruction of intrahepatic biliary epithelial cells (IBEC) lining the small intrahepatic bile ducts. This leads to obstruction and interference with bile secretion, causing eventual cirrhosis. Association with other autoimmune diseases characterized by epithelium lining/secretory system damage has been reported, including Sjogren's Syndrome, CREST Syndrome, autoimmune thyroid disease and rheumatoid arthritis.

In another embodiment, the disease treated by the methods provided herein is celiac disease, also known as celiac sprue or gluten-sensitive enteropathy. Celiac disease is a disease that results from defective gastrointestinal absorption due to hypersensitivity to cereal grain storage proteins, including glutens or its product gliadin and glutenin, present in wheat, barley, and oats. The disease is caused by CD4 T cells that recognize gliadin as dietary antigen and these cells induce a Th1-mediated chronic inflammatory response. Symptoms include diarrhea, weight loss, and steatorrhea, villous atrophy and malabsorption are seen. It may also be associated with dermatitis herpetiforms, a vesicular skin eruption. Celiac disease is associated with alleles DQB1*0302 and DQB1*0201 combined with DQA1*0301 and DQA1*0501. 95% of patients carry either DQB1*0201 or DQB1*0302. The strong HLA association is believed to be due to the capacity of DQ molecules encoded by DQB1*0201, DQA1*0501, DQB1*0302 and DQA1*0301 to efficiently present deaminated variants of glutamine-rich peptides derived from gliadin and glutenin.

In another embodiment, the method for treating an autoimmune disease in a subject further involves inhibiting the proliferation or function of T cells which are responsive to an autoantigen. The pathological process of autoimmune diseases and immune rejection is mediated by T cells. Upon binding to and recognition of an antigen, T cells proliferate, secrete cytokines and recruit additional inflammatory and cytotoxic cells to the site.

In yet another embodiment, the methods described herein for treating an autoimmune disease in a subject involve binding the random copolymer to a major histocompatibility complex class II protein which is associated with an autoimmune disease. The Class II MHC proteins are expressed predominantly on the surfaces of B lymphocytes and antigen presenting cells such as macrophages. These Class II MHC proteins have a peptide-binding cleft which is the site at which antigenic peptides are presented to T cells. When the present random copolymers bind to a major histocompatibility complex class II protein, those random copolymers can block or otherwise interfere with antigen presentation and/or T cell activation.

In one embodiment, the disease treated by the methods of the present invention is host-versus-graft disease (HVGD) or graft-versus-host disease (GVHD). Transplantation systems such as organ transplantations and bone marrow reconstitution have become important and effective therapies for many life threatening diseases. However, immune rejection is still the major barrier for successful transplantation. This is manifested in functional deterioration and graft rejection in the case of organ transplantation (host-versus-graft disease, or HVGD. Another manifestation of pathological immune reactivity is GVHD that occurs in approximately 30% of bone marrow recipients. Up to half of those patients who develop GVHD may succumb to this process. This high morbidity and mortality has led to continuous interest in the possibility of controlling or preventing GVHD. Clinicopathologically, two forms of GVHD have been recognized. Acute GVHD develops within the first 3 months after bone marrow transplantation and features disorders of skin, liver and gastrointestinal tract. Chronic GVHD is a multi-organ autoimmune-like disease emerging from 3 months up to 3 years post-transplantation and shares features common to naturally occurring autoimmune disorders, like systemic lupus erythematosus (SLE) and scleroderma. The methods described herein may be used to treat both acute and chronic GVHD.

In a specific embodiment of the methods described herein, Copolymer 1 or YFAK random copolymer may be used for prevention and treatment of GVHD in all cases of organ transplantation that develop GVHD, but particularly in fetal thymus, and more particularly, in allogeneic bone marrow, transplantation. To a patient under suitable conditioning regimen, the GLAT copolymer may be administered in a treatment regimen from day −2 prior to the transplantation day, and then for another 60-100, at least 60 days, after the transplantation day. A regimen of such duration may comprise administrations of the random copolymer at intervals greater than 24, 30, 36, 42, or 48 hours. Other immunosuppressive drugs, such as cyclosporine, methotrexate and prednisone, may be administered with the Copolymer 1 copolymer.

The method of the invention may also be applied to the prevention and treatment of GVHD in the course of bone marrow transplantation in patients suffering from diseases curable by bone marrow transplantation, including leukemias, such as acute lymphoblastic leukemia (ALL), acute nonlymphoblastic leukemia (ANLL), acute myelocytic leukemia (AML) and chronic myelocytic leukemia (CML), severe combined immunodeficiency syndromes (SCID), osteopetrosis, aplastic anemia, Gaucher's disease, thalassemia and other congenital or genetically-determined hematopoietic or metabolic abnormalities.

In another embodiment, the methods of the present invention may be applied to promote nerve regeneration or to prevent or inhibit secondary degeneration which may otherwise follow primary nervous system injury, e.g., closed head injuries and blunt trauma, such as those caused by participation in dangerous sports, penetrating trauma, such as gunshot wounds, hemorrhagic stroke, ischemic stroke, glaucoma, cerebral ischemia, or damages caused by surgery such as tumor excision. In addition, such compositions may be used to ameliorate the effects of disease that result in a degenerative process, e.g., degeneration occurring in either gray or white matter (or both) as a result of various diseases or disorders, including, without limitation: diabetic neuropathy, senile dementias, Alzheimer's disease, Parkinson's Disease, facial nerve (Bell's) palsy, glaucoma, Huntington's chorea, amyotrophic lateral sclerosis (ALS), status epilepticus, non-arteritic optic neuropathy, intervertebral disc herniation, vitamin deficiency, prion diseases such as Creutzfeldt-Jakob disease, carpal tunnel syndrome, peripheral neuropathies associated with various diseases, including but not limited to, uremia, porphyria, hypoglycemia, Sjorgren Larsson syndrome, acute sensory neuropathy, chronic ataxic neuropathy, biliary cirrhosis, primary amyloidosis, obstructive lung diseases, acromegaly, malabsorption syndromes, polycythemia vera, IgA and IgG gammapathies, complications of various drugs (e.g., metronidazole) and toxins (e.g., alcohol or organophosphates), Charcot-Marie-Tooth disease, ataxia telangectasia, Friedreich's ataxia, amyloid polyneuropathies, adrenomyeloneuropathy, Giant axonal neuropathy, Refsum's disease, Fabry's disease, lipoproteinemia, etc. In addition, other clinical conditions that may be treated through the administration of a random copolymer in accordance with the present invention include epilepsy, amnesia, anxiety, hyperalgesia, psychosis, seizures, abnormally elevated intraocular pressure, oxidative stress, and opiate tolerance and dependence.

In a specific embodiments, the disease treated by the methods described herein comprises multiple sclerosis, type-I diabetes, Hashimoto's thyroiditis, Crohn's disease, rheumatoid arthritis, systemic lupus erythematosus (SLE), gastritis, autoimmune hepatitis, hemolytic anemia, autoimmune hemophilia, autoimmune lymphoproliferative syndrome (ALPS), autoimmune uveoretinitis, glomerulonephritis, Guillain-Barré syndrome, psoriasis, myasthenia gravis, autoimmune encephalomyelitis, Goodpasture's syndrome, Grave's disease, paraneoplastic pemphigus, autoimmune thrombocytopenic purpura, scleroderma with anti-collagen antibodies, mixed connective tissue disease, pernicious anemia, polymyositis, idiopathic Addison's disease, autoimmune-associated infertility, bullous pemphigoid, Sjogren's syndrome, idiopathic myxedema or colitis. In some embodiments, the subject is afflicted with more than one disease.

V. Therapeutic Compositions

The random copolymers of the present invention may be administered to the subject as a composition which comprises a pharmaceutically effective amount of copolymer and an acceptable carrier and/or excipients. A pharmaceutically acceptable carrier includes any solvents, dispersion media, or coatings that are physiologically compatible. Preferably, the carrier is suitable for intravenous, intramuscular, oral, intraperitoneal, intradermal, transdermal, topical, or subcutaneous administration. One exemplary pharmaceutically acceptable carrier is physiological saline. Other pharmaceutically acceptable carriers and their formulations are well-known and generally described in, for example, *Remington's Pharmaceutical Science* ($18^{th}$ Ed., ed. Gennaro, Mack Publishing Co., Easton, Pa., 1990). Various pharmaceutically acceptable excipients are well-known in the art and can be found in, for example, *Handbook of Pharmaceutical Excipients* ($4^{th}$ ed., Ed. Rowe et al. Pharmaceutical Press, Washington, D.C.). The composition can be formulated as a solution, microemulsion, liposome, capsule, tablet, or other suitable forms. The active component which comprises the copolymer may be coated in a material to protect it from inactivation by the environment prior to reaching the target site of action. The pharmaceutical compositions of the present invention are preferably sterile and non-pyrogenic at the time of delivery, and are preferably stable under the conditions of manufacture and storage.

In other embodiments of the present invention, the pharmaceutical compositions are regulated-release formulations. Copolymers of the present invention may be admixed with biologically compatible polymers or matrices which control the release rate of the copolymers into the immediate environment. Controlled or sustained release compositions include formulation in lipophilic depots (e.g., fatty acids, waxes, oils).

In some embodiments of the present invention, pharmaceutical compositions comprise random copolymers formulated with oil and emulsifier to form water-in-oil microparticles and/or emulsions. The oil may be any non-toxic hydrophobic material liquid at ambient temperature to about body temperature, such as edible vegetable oils including safflower oil, soybean oil, corn oil, and canola oil; or mineral oil. Chemically defined oil substance such as lauryl glycol may also be used. The emulsifier useful for this embodiment includes Span 20 (sorbitan monolaurate) and phosphatidylcholine. In some embodiments, a random copolymer composition is prepared as an aqueous solution and is prepared into an water-in-oil emulsion dispersed in 95 to 65% oil such as mineral oil, and 5 to 35% emulsifier such as Span 20. In another embodiment of the invention, the emulsion is formed with alum rather than with oil and emulsifier. These emulsions and microparticles reduce the speed of uptake of random copolymer, and achieve controlled antigen delivery.

In some embodiments, the pharmaceutical compositions also include additional therapeutically active agents. Such additional ingredient can be at least an additional random copolymer, such as a Copolymer 1 (YEAK, Copaxone™) that binds to a different HLA molecule, an antibody which binds to an unwanted inflammatory molecule or cytokine such as interleukin-6, interleukin-8, granulocyte macrophage colony stimulating factor, and tumor necrosis factor-α; an enzyme inhibitor such as a protease inhibitor aprotinin or a cyclooxygenase inhibitor; an antibiotic such as amoxicillin, rifampicin, erythromycin; an antiviral agent such as acyclovir; a steroidal anti-inflammatory such as a glucocorticoid; a non-steroidal anti-inflammatory such as aspirin, ibuprofen, or acetaminophen; or a non-inflammatory cytokine such as interleukin-4 or interleukin-10. Other cytokines and growth factors such as interferon-β, tumor necrosis factors, antiangiogenic factors, erythropoietins, thrombopoietins, interleukins, maturation factors, chemotactic protein, and their variants and derivatives that retain similar physiological activities may also be used as an additional ingredient.

In some embodiments, the additional active therapeutically active agent is selected from the group consisting of anti-psoriasis creams, eye drops, nose drops, Sulfasalazine, glucocorticoids, propylthiouracil, methimazole, $I^{131}$, insulin, IFN-β1a, IFN-β1b, glucocorticoids, ACTH, avonex, azathioupurine, cyclophosphamide, UV-B, PUVA, methotrexate, calcipitriol, cyclophosphamide, OKT3, FK-506, cyclosporin A, azathioprine, and mycophenolate mofetil.

Copolymers of the invention may also be used in combination with anti-obesity drugs. Anti-obesity drugs include P-3 agonists, CB-1 antagonists, appetite suppressants, such as, for example, sibutramine (Meridia), and lipase inhibitors, such as, for example, orlistat (Xenical). The subject copolymers may also be used in methods of the invention in combination with drugs commonly used to treat lipid disorders in diabetic patients. Such drugs include, but are not limited to, HMG-CoA reductase inhibitors, nicotinic acid, bile acid sequestrants, and fibric acid derivatives. Polypeptides of the invention may also be used in combination with anti-hypertensive drugs, such as, for example, β-blockers, cathepsin S inhibitors and ACE inhibitors. Examples of β-blockers are: acebutolol, bisoprolol, esmolol, propanolol, atenolol, labetalol, carvedilol, and metoprolol. Examples of ACE inhibitors are: captopril, enalapril, lisinopril, benazepril, fosinopril, ramipril, quinapril, perindopril, trandolapril, and moexipril.

The invention further provides a kit comprising (i) a composition comprising a random copolymer and (ii) instructions for administering the composition to a subject in need thereof at intervals greater than 24 hours, more preferably greater than 36 hours, for the treatment of a disease, such as an autoimmune disease. In one embodiment, the autoimmune disorder is multiple sclerosis. In a preferred embodiment, the random copolymer is Copolymer 1. In another preferred embodiment, the random copolymer is formulated in dosages for administration of greater than about 24, 30, 36, 42, 48, 54, 60, 66, 72, 78, 84, 90, 96, 102, 108, 114, 120, 126, 132, 138, 144, 150, 156, 162, 168, 174, 180, 186, 192, 198, 204, 210, 216, 222, 228, 234, or 240 hours, or any intervening interval thereof. In another embodiment of the kits described herein, the instructions indicate that the random polymer is to be administered every about 24, 30, 36, 42, 48, 54, 60, 66, 72, 78, 84, 90, 96, 102, 108, 114, 120, 126, 132, 138, 144, 150, 156, 162, 168, 174, 180, 186, 192, 198, 204, 210, 216, 222, 228, 234, or 240 hours, or any interval in between. Kits may comprise additional components, such as packaging and one or more apparatuses for the administration of the copolymer, such as a hypodermic syringe.

In a specific embodiment, the autoimmune disease is selected from the group consisting of multiple sclerosis, type-I diabetes, Hashimoto's thyroiditis, Crohn's disease, rheumatoid arthritis, systemic lupus erythematosus (SLE), gastritis, autoimmune hepatitis, hemolytic anemia, autoimmune hemophilia, autoimmune lymphoproliferative syndrome (ALPS), autoimmune uveoretinitis, glomerulonephritis, Guillain-Barré syndrome, psoriasis, myasthenia gravis, autoimmune encephalomyelitis, Goodpasture's syndrome, Grave's disease, paraneoplastic pemphigus, autoimmune thrombocytopenic purpura, scleroderma with anti-collagen antibodies, mixed connective tissue disease, pernicious anemia, polymyositis, idiopathic Addison's disease, autoimmune-associated infertility, bullous pemphigoid, Sjogren's syndrome, idiopathic myxedema and colitis.

VI. Methods of Treatment

One aspect of the present invention provides novel methods to treat a subject afflicted with or suspected of being afflicted with a disease, such as an autoimmune disease, by administering one or more random copolymers to the subject in a therapeutically effective amount. In particular, subcutaneous administration of a pharmaceutical composition comprising a random copolymer composition is contemplated as a preferred embodiment of the invention. Subcutaneous injection induces more desired immune responses biased for $T_H2$ response, which is the basis for the tolerance for certain antigens.

In general, the methods of treatment of the present invention, which is immunomodulation of the subject in need of such treatment, can be differentiated from vaccination. Successful vaccination is dependent on the immunogenicity of the vaccine being administered, which increases the titer of antibodies directly reactive to the antigens in the vaccine. In contrast, the random copolymers of the present invention are effective in treating diseases without inducing a high titer of antibodies against the copolymers themselves. As demonstrated by the Examples below, the effectiveness of the methods of the present invention does not depend on the antibody production against the copolymers, and therefore is fundamentally different from vaccination. Unlike vaccination, random copolymers of the present invention, administered by the methods of the invention, induces tolerance toward the disease-related antigens, and more specifically, induces peripheral tolerance. Peripheral tolerance, in contract to central tolerance, has the advantage of being safer as a modulatory phenomenon. Accordingly, one aspect of the present invention is embodied in a method of administration of a composition comprising a random copolymer of the invention so as to induce peripheral tolerance toward the random copolymer and the disease related antigens.

In general, an embodiment of the invention is to administer a suitable dose of a therapeutic copolymer composition that will be the lowest effective dose to produce a therapeutic effect, for example, mitigating symptoms. The therapeutic copolymers are preferably administered at a dose per subject, which corresponds to a dose per day of at least about 2 mg, at least about 5 mg, at least about 10 mg, or at least about 20 mg as appropriate minimal starting dosages, or about x mg, wherein x is an integer between 1 and 20. In one embodiment of the methods described herein, a dose of about 0.01 to about 500 mg/kg can be administered. In general, the effective dosage of the compound of the present invention is about 50 to about 400 micrograms of the compound per kilogram of the subject per day. In one specific embodiment, the equivalent dosage per day, regardless of the frequency with which the doses are administered, is from about 5 to 100, or more preferably, from about 10 to 40, or more preferably about 20 mg/day. In another specific embodiment, each individual dosage in the treatment regimen is from about 5 to 100, or more preferably from about 10 to 40, or more preferably about 20 mg/dose.

However, it is understood by one skilled in the art that the dose of the composition of the invention will vary depending on the subject and upon the particular route of administration used. It is routine in the art to adjust the dosage to suit the individual subjects. Additionally, the effective amount may be based upon, among other things, the size of the compound, the biodegradability of the compound, the bioactivity of the compound and the bioavailability of the compound. If the compound does not degrade quickly, is bioavailable and highly active, a smaller amount will be required to be effective. The actual dosage suitable for a subject can easily be determined as a routine practice by one skilled in the art, for example a physician or a veterinarian given a general starting point. For example, the physician or veterinarian could start doses of the compound of the invention employed in the pharmaceutical composition at a level lower than that required in order to achieve the desired therapeutic effect, and increase the dosage with time until the desired effect is achieved. A physician or veterinarian may also refer to the recommendations for the administration of Copaxone™ as a general starting point.

In the context of the invention, the term "treatment regimen" is meant to encompass therapeutic, palliative and prophylactic modalities of administration of one or more compositions comprising one or more random copolymers. A particular treatment regimen may last for a period of time which will vary depending upon the nature of the particular disease or disorder, its severity and the overall condition of the patient, and may extend from once daily, or more preferably once every 36 hours or 48 hours or longer, to once every month or several months. Following treatment, the patient is monitored for changes in his/her condition and for alleviation of the symptoms of the disorder or disease state. The dosage of the oligonucleotide may either be increased in the event the patient does not respond significantly to current dosage levels, or the dose may be decreased if an alleviation of the symptoms of the disorder or disease state is observed, or if the disorder or disease state has been ablated, or if an unacceptable side effects are seen with the starting dosage.

In one embodiment, a therapeutically effective amount of the random copolymer is administered to the subject in a treatment regimen comprising intervals of at least 36 hours, or more preferably 48 hours, between dosages. In another embodiment, the random copolymer is administered at intervals of at least 54, 60, 66, 72, 78, 84, 90, 96, 102, 108, 114, 120, 126, 132, 138, 144, 150, 156, 162, 168, 174, 180, 186, 192, 198, 204, 210, 216, 222, 228, 234, or 240 hours, or the equivalent amount of days. In some embodiments, the agent is administered every other day, while in other embodiments it is administered weekly. If two copolymers are administered to the subject, such copolymers may be administered at the same time, such as simultaneously, or essentially at the same time, such as in succession. Alternatively, their administration may be staggered. For example, two copolymers which are each administered every 48 hours may both be administered on the same days, or one may be administered one day and the other on the next day and so on in an alternating fashion.

As shown by the Examples below, treatment regimens with longer dosing intervals, consequently often with lower total exposure of copolymers, induce lower titers of antibodies against copolymers themselves, while still inducing desired protective effects. Such reduction of neutralizing antibodies are desirable because it is considered likely to help random copolymer compositions to retain its effectiveness without being neutralized, and it is associated with reduced risk of anaphylactic shocks, providing safer treatments of diseases. Longer interval regimens are also desirable because they strengthen the bias for $T_H2$ responses, which is considered to be the mode of action for the random copolymer therapies.

In other embodiments, the random copolymer is administered in a treatment regimen which comprises at least one uneven time interval, wherein at least one of the time intervals is at least 24, 30, 36, 42, 48, 54, 60, 66, 72, 78, 84, 90, 96, 102, 108, 114, 120, 126, 132, 138, 144, 150, 156, 162, 168, 174, 180, 186, 192, 198, 204, 210, 216, 222, 228, 234, or 240 hours, or the equivalent amount of days.

In one embodiment, the polymer is administered to be subject at least three times during a treatment regimen, such that there are at least two time intervals between administrations. These intervals may be denoted $I_1$ and $I_2$. If the polymer is administered four times, then there would be an additional interval between the third and fourth administrations, $I_3$, such that the number of intervals for a given number "n" of administrations is n−1. Accordingly, in one embodiment, at least one of the time intervals between administrations is greater than about 24, 30, 36, 42, 48, 54, 60, 66, 72, 78, 84, 90, 96, 102, 108, 114, 120, 126, 132, 138, 144, 150, 156, 162, 168, 174, 180, 186, 192, 198, 204, 210, 216, 222, 228, 234, or 240 hours. In another embodiment, at least 1%, 2%, 3%, 4%, 5%, 10%, 15%, 20%, 25%, 30%, 40%, 50%, 60%, 70%, 80%, 90% or 95% of the total number n−1 of time intervals are at least about 24, 30, 36, 42, 48, 54, 60, 66, 72, 78, 84, 90, 96, 102, 108, 114, 120, 126, 132, 138, 144, 150, 156, 162, 168, 174, 180, 186, 192, 198, 204, 210, 216, 222, 228, 234, or 240 hours.

In yet another embodiment, the average time interval between administrations $((I_1+I_2+\ldots+I_{n-1})/n-1)$ is at least 24, 30, 36, 42, 48, 54, 60, 66, 72, 78, 84, 90, 96, 102, 108, 114, 120, 126, 132, 138, 144, 150, 156, 162, 168, 174, 180, 186, 192, 198, 204, 210, 216, 222, 228, 234, or 240 hours, or at least two weeks.

In another embodiment, the dosage regimen consists of two or more different interval sets. For example, a first part of the dosage regimen is administered to a subject daily, every other day, or every third day, for example, at about 22 mg copolymer/m² body surface area of the subject, wherein the subject is a human. In some embodiment of the invention, the dosing regimen starts with dosing the subject every other day, every third day, weekly, biweekly, or monthly. The dosage for administration every other day or every third day may be up to about 65 mg/m² and 110 mg/m² respectively. For a dosing regimen comprising dosing of the random copolymer every week, the dose comprises up to about 500 mg/m², and for a dosing regimen comprising dosing of the random copolymer every two weeks or every month, up to 1.5 g/m² may be administered. The first part of the dosing regimen may be administered for up to 30 days, for example, 7, 14, 21, or 30 days. A subsequent second part of the dosing regimen with a different, longer interval administration with usually lower exposure (step-down dosage), administered weekly, every 14 days, or monthly may optionally follow, for example, at 500 mg/m² body surface area weekly, up to maximum of about 1.5 g/m² body surface area, continuing for 4 weeks up to two years, for example, 4, 6, 8, 12, 16, 26, 32, 40, 52, 63, 68, 78, or 104 weeks. Alternatively, if the disease goes into remission or generally improves, the dosage may be maintained or kept at lower than maximum amount, for example, at 140 mg/m² body surface area weekly. If, during the step-down dosage regimen, the disease condition relapses, the first dosage regimen may be resumed until effect is seen, and the second dosing regimen may be implemented. This cycle may be repeated multiple times as necessary.

More specifically, one aspect of the invention is treatment of diseases treatable with a random copolymer. One embodiment of the invention is a method for treating diseases treatable with random copolymer of the composition YFAK (L-tyrosine, L-phenylalanine, L-alanine and L-lysine) in a molar input ratio of about 1.0:1.0:10.0:6.0 respectively, synthesized by solid phase chemistry, wherein the copolymer has a length of 52 amino acids, by administering said random copolymer to a human subject in need of treatment a first part of a dosing regimen comprising a dose of about 22 mg/m$^2$ body surface area daily. In some embodiment of the invention, the dosing regimen starts with dosing the subject every other day, every third day, weekly, biweekly, or monthly. The dosage for administration every other day or every third day may be up to about 65 mg/m$^2$ and 110 mg/m$^2$ respectively. For a dosing regimen comprising dosing of the random copolymer every week, the dose comprises up to about 500 mg/m$^2$, and for a dosing regimen comprising dosing of the random copolymer every two weeks or every month, up to 1.5 g/m$^2$ may be administered. The first part of the dosing regimen may be administered for up to 30 days, for example, 7, 14, 21, or 30 days. A subsequent second part of the dosing regimen with a different, longer interval administration with usually lower exposure (step-down dosage), administered weekly, every 14 days, or monthly may optionally follow, for example, at 500 mg/m$^2$ body surface area weekly, up to maximum of about 1.5 g/m$^2$ body surface area, continuing for 4 weeks up to two years, for example, 4, 6, 8, 12, 16, 26, 32, 40, 52, 63, 68, 78, or 104 weeks. Alternatively, if the disease goes into remission or generally improves, the dosage may be maintained or kept at lower than maximum amount, for example, at 140 mg/m$^2$ body surface area weekly. If, during the step-down dosage regimen, the disease condition relapses, the first dosage regimen may be resumed until effect is seen, and the second dosing regimen may be implemented. This cycle may be repeated multiple times as necessary.

In another embodiment of the invention, the method is for treating diseases treatable with Copolymer 1 (YEAK) of about 52 amino acid length, having a molar input ratio of about 1.0:2.0:6.0:5.0, and synthesized by solid phase chemistry. The dosage regimen is similar to that described for YFAK above.

Another embodiment of the invention is a method of treating diseases treatable with a random copolymer of the composition YFAK (L-tyrosine, L-phenylalanine, L-alanine and L-lysine) in an output average molar ratio of about 1.0:1.2:18.0:6.0 respectively, synthesized by solid phase chemistry, wherein the copolymer has a length of 52 amino acids, and wherein residues 1-10 of the copolymer sequence has a molar output ratio of about 1.0:1.2:16:6, residues 11-30 have a molar output ratio of about 1.0:1.2:18:6, and residues 31-52 have a molar output ratio of about 1.0:1.2:20:6 by administering said random copolymer to a human subject in need of treatment a dose of about 22 mg/m$^2$ body surface area daily, or with longer intervals such as every other day, every third day, weekly, biweekly, or monthly, as described above. In another embodiment of the invention, the method is for treating diseases treatable with Copolymer 1 (YEAK) of about 52 amino acid length, having a molar input ratio of about 1.0:2.0:6.0:5.0, and synthesized by solid phase chemistry, wherein residues 1-10 of the copolymer sequence has a molar output ratio of about 1.0:2.0:5.5:5.0, residues 11-30 have a molar output ratio of about 1.0:2.0:6.0:5.0, and residues 31-52 have a molar output ratio of about 1.0:2.0:6.5:5.0. The dosage regimen is similar to that described above, and may optionally include the step-down sage. If, during the step-down dosage regimen, the disease condition relapses, the first dosage regimen may be resumed until effect is seen, and the second dosing regimen may be implemented. This cycle may be repeated multiple times as necessary.

Another aspect of the invention is embodied as a means for ameliorating diseases treatable with a random copolymer comprising the composition YFAK (L-tyrosine, L-phenylalanine, L-alanine and L-lysine) in an molar input ratio of about 1.0:1.0:X$_A$:6.0, wherein X$_A$ is a number greater than 5.0 and less than 15.0 respectively by administering to a subject a dose effective in ameliorating said diseases. More specifically, one embodiment of the invention is a means for ameliorating diseases treatable with a random copolymer of the composition YFAK (L-tyrosine, L-phenylalanine, L-alanine and L-lysine) in an output average molar ratio of about 1.0:1.2:18.0:6.0 respectively, synthesized by solid phase chemistry, wherein the copolymer has a length of 52 amino acids, and wherein residues 1-10 of the copolymer sequence has a ratio of about 1.0:1.2:16:6, residues 11-30 have a ratio of about 1.0:1.2:18:6, and residues 31-52 have a ratio of about 1.0:1.2:20:6. In another embodiment of the invention, the method is for treating diseases treatable with Copolymer 1 (YEAK) of about 52 amino acid length, having a molar input ratio of about 1.0:2.0:6.0:5.0, and synthesized by solid phase chemistry, wherein residues 1-10 of the copolymer sequence has a molar output ratio of about 1.0:2.0:5.5:5.0, residues 11-30 have a molar output ratio of about 1.0:2.0:6.0:5.0, and residues 31-52 have a molar output ratio of about 1.0:2.0:6.5:5.0. The subject is treated following a dosage regimen at about 22 mg copolymer/m$^2$ body surface area of the subject, wherein the subject is a human. In some embodiment of the invention, the dosing regimen starts with dosing the subject every other day, every third day, weekly, biweekly, or monthly. The dosage for administration every other day or every third day may be up to about 65 mg/m$^2$ and 110 mg/m$^2$ respectively. For a dosing regimen comprising dosing of the random copolymer every week, the dose comprises up to about 500 mg/m$^2$, and for a dosing regimen comprising dosing of the random copolymer every two weeks or every month, up to 1.5 g/m$^2$ may be administered. The first part of the dosing regimen may be administered for up to 30 days, for example, 7, 14, 21, or 30 days. A subsequent second part of the dosing regimen with a different, longer interval administration with usually lower exposure (step-down dosage), administered weekly, every 14 days, or monthly may optionally follow, for example, at 500 mg/m$^2$ body surface area weekly, up to maximum of about 1.5 g/m$^2$ body surface area, continuing for 4 weeks up to two years, for example, 4, 6, 8, 12, 16, 26, 32, 40, 52, 63, 68, 78, or 104 weeks. Alternatively, if the disease goes into remission or generally improves, the dosage may be maintained or kept at lower than maximum amount, for example, at 140 mg/m$^2$ body surface area weekly. If, during the step-down dosage regimen, the disease condition relapses, the first dosage regimen may be resumed until effect is seen, and the second dosing regimen may be implemented. This cycle may be repeated multiple times as necessary.

An aspect of the invention is a means for ameliorating unwanted immune responses by administering to a subject a dose effective in ameliorating said diseases with a random copolymer comprising the composition YFAK (L-tyrosine, L-phenylalanine, L-alanine and L-lysine) in an molar input ratio of about 1.0:1.0:10.0:6.0 respectively. In another embodiment of the invention, the method is for treating diseases treatable with Copolymer 1 (YEAK) of about 52 amino acid length, having a molar input ratio of about 1.0:2.0:6.0:5.0, and synthesized by solid phase chemistry. The dosage regimen is similar to that described for YFAK herein. For both types of random copolymers, an exemplary means is by administering to a human subject a daily dose of about 22 mg random copolymer/m$^2$ body surface area. In some embodiment of the invention, the dosing regimen starts with dosing the subject every other day, every third day, weekly, biweekly, or monthly. The dosage for administration every other day or every third day may be up to about 65 mg/m$^2$ and 110 mg/m$^2$ respectively. For a dosing regimen comprising dosing of the random copolymer every week, the dose comprises up to about 500 mg/m$^2$, and for a dosing regimen comprising dosing of the random copolymer every two weeks or every month, up to 1.5 g/m$^2$ may be administered. The first part of the dosing regimen may be administered for up to 30 days, for example, 7, 14, 21, or 30 days. A subsequent second part of the dosing regimen with a different, longer interval administration with usually lower exposure (step-down dosage), administered weekly, every 14 days, or monthly may optionally follow, for example, at 500 mg/m$^2$ body surface area weekly, up to maximum of about 1.5 g/m$^2$ body surface area, continuing for 4 weeks up to two years, for example, 4, 6, 8, 12, 16, 26, 32, 40, 52, 63, 68, 78, or 104 weeks. Alternatively, if the disease goes into remission or generally improves, the dosage may be maintained or kept at lower than maximum amount, for example, at 140 mg/m$^2$ body surface area weekly. If, during the step-down dosage regimen, the disease condition relapses, the first dosage regimen may be resumed until effect is seen, and the second dosing regimen may be implemented. This cycle may be repeated multiple times as necessary.

Yet another embodiment of the invention is a means for ameliorating unwanted immune responses with a random copolymer of the composition YFAK (L-tyrosine, L-phenylalanine, L-alanine and L-lysine) in an output average molar ratio of about 1.0:1.2:18.0:6.0 respectively, synthesized by solid phase chemistry, wherein the copolymer has a length of 52 amino acids, and wherein residues 1-10 of the copolymer sequence has a ratio of about 1.0:1.2:16:6, residues 11-30 have a ratio of about 1.0:1.2:18:6, and residues 31-52 have a ratio of about 1.0:1.2:20:6. In another embodiment of the invention, the method is for treating diseases treatable with Copolymer 1 (YEAK) of about 52 amino acid length, having a molar input ratio of about 1.0:2.0:6.0:5.0, and synthesized by solid phase chemistry, wherein residues 1-10 of the copolymer sequence has a molar output ratio of about 1.0:2.0:5.5:5.0, residues 11-30 have a molar output ratio of about 1.0:2.0:6.0:5.0, and residues 31-52 have a molar output ratio of about 1.0:2.0:6.5:5.0. The dosage regimen is similar to that described for YFAK above. For both types of random copolymers, such method may be carried out by administering to a human subject a daily dose of about 22 mg random copolymer/m$^2$ body surface area. Dosing regimens may be similar to those described above, tailored to the subject's needs. Alternatively, the random copolymer may be administered to a human subject at a maximum daily dose of about 80 mg.

Another aspect of the invention is a method for ameliorating unwanted immune responses having a TH1 phenotype with a random copolymer of the composition YFAK (L-tyrosine, L-phenylalanine, L-alanine and L-lysine) in an output average molar ratio of about 1.0:1.2:18.0:6.0 respectively, synthesized by solid phase chemistry, wherein the copolymer has a length of 52 amino acids, and wherein residues 1-10 of the copolymer sequence has a ratio of about 1.0:1.2:16:6, residues 11-30 have a ratio of about 1.0:1.2:18:6, and residues 31-52 have a ratio of about 1.0:1.2:20:6. In another embodiment of the invention, the method is for treating diseases treatable with Copolymer 1 (YEAK) of about 52 amino acid length, having a molar input ratio of about 1.0:2.0:6.0:5.0, and synthesized by solid phase chemistry, wherein residues 1-10 of the copolymer sequence has a molar output ratio of about 1.0:2.0:5.5:5.0, residues 11-30 have a molar output ratio of about 1.0:2.0:6.0:5.0, and residues 31-52 have a molar output ratio of about 1.0:2.0:6.5:5.0. For both types of random copolymers, the dosage regimen may be determined, tailored to the subject's needs, and can be similar to that described above.

Yet another aspect of the invention is a means for ameliorating autoimmune reactions in a subject with a random copolymer of the composition YFAK (L-tyrosine, L-phenylalanine, L-alanine and L-lysine) in an output average molar ratio of about 1.0:1.2:18.0:6.0 respectively, synthesized by solid phase chemistry, wherein the copolymer has a length of 52 amino acids, and wherein residues 1-10 of the copolymer sequence has a ratio of about 1.0:1.2:16:6, residues 11-30 have a ratio of about 1.0:1.2:18:6, and residues 31-52 have a ratio of about 1.0:1.2:20:6. In another embodiment of the invention, the method is for treating diseases treatable with Copolymer 1 (YEAK) of about 52 amino acid length, having a molar input ratio of about 1.0:2.0:6.0:5.0, and synthesized by solid phase chemistry, wherein residues 1-10 of the copolymer sequence has a molar output ratio of about 1.0:2.0:5.5:5.0, residues 11-30 have a molar output ratio of about 1.0:2.0:6.0:5.0, and residues 31-52 have a molar output ratio of about 1.0:2.0:6.5:5.0. For both types of random copolymers, dosing regimens may be similar to those described above, tailored to the subject's needs.

Any of the methods and means may be practiced using compositions and formulations described in this application.

In other embodiments of the invention, any of the methods of the invention may be practiced using sustained release formulation comprising a random copolymer. When administering a random copolymer of the invention using a sustained release formula, the overall exposure to the copolymer is generally lower than in bolus administration. For example, a first part of the dosage regimen is administered to a subject daily, every other day, or every third day, for example, at about 22 mg copolymer/m$^2$ body surface area of the subject, wherein the subject is a human. In some embodiment of the invention, the dosing regimen uses sustained release formula, dosing the subject every other day, every third day, weekly, biweekly, or monthly so that the copolymer is released during the interval. The dosage for administration every other day or every third day may be up to about 35 mg/m$^2$ and 65 mg/m$^2$ respectively. For a dosing regimen comprising dosing of the random copolymer every week, the dose comprises up to about 140 mg/m$^2$, and for a dosing regimen comprising dosing of the random copolymer every two weeks or every month, up to 750 mg/m$^2$ may be administered. The first part of the dosing regimen may be administered for up to 30 days, for example, 7, 14, 21, or 30 days. A subsequent second part of the dosing regimen with a different, longer interval administration with usually lower exposure (step-down dosage), administered weekly, every 14 days, or monthly may optionally follow, for example, at 140 mg/m$^2$ body surface area weekly, up to maximum of about 1.5 g/m$^2$ body surface area, continuing for 4 weeks up to two years, for example, 4, 6, 8, 12, 16, 26, 32, 40, 52, 63, 68, 78, or 104 weeks. Alternatively, if the disease goes into remission or generally improves, the dosage may be maintained or kept at lower than maximum amount, for example, at 140 mg/m$^2$ body surface area weekly. If, during the step-down dosage regimen, the disease condition relapses, the first dosage regimen may be resumed until effect is seen, and the second dosing regimen may be implemented. This cycle may be repeated multiple times as necessary.

Another aspect of the invention is a means for treating a subject afflicted with or showing the symptoms of multiple sclerosis (MS) with a random copolymer of the composition YFAK (L-tyrosine, L-phenylalanine, L-alanine and L-lysine) in an output average molar ratio of about 1.0:1.2:18.0:6.0 respectively, synthesized by solid phase chemistry, wherein the copolymer has a length of 52 amino acids, and wherein residues 1-10 of the copolymer sequence have a ratio of about 1.0:1.2:16:6, residues 11-30 have a ratio of about 1.0:1.2:18:6, and residues 31-52 have a ratio of about 1.0:1.2:20:6. In another embodiment of the invention, the method is for treating diseases treatable with Copolymer 1 (YEAK) of about 52 amino acid length, having a molar input ratio of about 1.0:2.0:6.0:5.0, and synthesized by solid phase chemistry, wherein residues 1-10 of the copolymer sequence has a molar output ratio of about 1.0:2.0:5.5:5.0, residues 11-30 have a molar output ratio of about 1.0:2.0:6.0:5.0, and residues 31-52 have a molar output ratio of about 1.0:2.0:6.5:5.0. Such copolymers may be administered to treat a subject afflicted with or showing the symptoms of MS with a maximum dose of 500 mg a random copolymer of above described random copolymer. The random copolymer may be delivered in a sustained release formulation.

Means for treating a subject suffering from multiple sclerosis with a maximum dose of 500 mg delivered in a sustained release formulation a random copolymer of the composition YFAK (L-tyrosine, L-phenylalanine, L-alanine and L-lysine) in an output average molar ratio of about 1.0:1.2:18.0:6.0 respectively, synthesized by solid phase chemistry, wherein the copolymer has a length of 52 amino acids, and wherein residues 1-10 of the copolymer sequence have a ratio of about 1.0:1.2:16:6, residues 11-30 have a ratio of about 1.0:1.2:18:6, and residues 31-52 have a ratio of about 1.0:1.2:20:6. In another embodiment of the invention, the method is for treating diseases treatable with Copolymer 1 (YEAK) of about 52 amino acid length, having a molar input ratio of about 1.0:2.0:6.0:5.0, and synthesized by solid phase chemistry, wherein residues 1-10 of the copolymer sequence has a molar output ratio of about 1.0:2.0:5.5:5.0, residues 11-30 have a molar output ratio of about 1.0:2.0:6.0:5.0, and residues 31-52 have a molar output ratio of about 1.0:2.0:6.5:5.0. Alternatively, the subject may be treated with a weekly maximum dose of 500 mg of the random copolymer, delivered in sustained release formulation.

In any of the exemplary embodiments described above, the volume of the each dosage form is preferably 0.1 ml to 5 ml.

In one embodiment of the methods described herein, the route of administration can be oral, intraperitoneal, transdermal, subcutaneous, by intravenous or intramuscular injection, by inhalation, topical, intralesional, infusion; liposome-mediated delivery; topical, intrathecal, gingival pocket, rectal, intravaginal, intrabronchial, nasal, transmucosal, intestinal, ocular or otic delivery, or any other methods known in the art as one skilled in the art may easily perceive. Other embodiments of the compositions of the invention incorporate particulate forms protective coatings, protease inhibitors or permeation enhancers for various routes of administration, including parenteral, pulmonary, nasal and oral. Administration can be systemic or local. In a preferred embodiment, the random copolymer is administered subcutaneously.

An embodiment of the methods of present invention relates to the administration of the copolymers of the present invention in a sustained release form. Such method comprises applying a sustained-release transdermal patch or implanting a sustained-release capsule or a coated implantable medical device so that a therapeutically effective dose of the copolymer of the present invention is delivered at defined time intervals to a subject of such a method. The compounds and/or agents of the subject invention may be delivered via a capsule which allows regulated-release of the random copolymer over a period of time. Controlled or sustained-release compositions include formulation in lipophilic depots (e.g., fatty acids, waxes, oils). Also comprehended by the invention are particulate compositions coated with polymers (e.g., poloxamers or poloxamines). In certain embodiments, a source of a copolymer is stereotactically provided within or proximate to the area of autoimmune attack, for example, near the pancreas for the treatment of IDDM.

For oral administration, the pharmaceutical preparation may be in liquid form, for example, solutions, syrups or suspensions, or may be presented as a drug product for reconstitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). The pharmaceutical compositions may take the form of, for example, tablets or capsules prepared by conventional means with pharmaceutically acceptable excipients such as binding agents (e.g., pre-gelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well-known in the art.

When Copolymer 1 or other random copolymer is introduced orally, it may be mixed with other food forms and consumed in solid, semi-solid, suspension, or emulsion form; and it may be mixed with pharmaceutically acceptable carriers, including water, suspending agents, emulsifying agents, flavor enhancers, and the like. In one embodiment, the oral composition is enterically-coated. Use of enteric coatings is well known in the art. For example, Lehman (1971) teaches enteric coatings such as Eudragit S and Eudragit L. The Handbook of Pharmaceutical Excipients, $2^{nd}$ Ed., also teaches Eudragit S and Eudragit L applications. One Eudragit which may be used in the present invention is L30D55. Preparations for oral administration may be suitably formulated to give controlled release of the active compound.

For buccal administration, the compositions may take the form of tablets or lozenges formulated in conventional manner. The compositions may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen free water, before use.

The compositions may also be formulated in rectal compositions such as suppositories or retention enemas, e.g., containing conventional suppository bases such as cocoa butter or other glycerides. For administration by inhalation, the compositions for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin, for use in an inhaler or insufflator may be formulated containing a powder mix of the compound and a suitable powder base such as lactose or starch.

In a preferred embodiment, compositions comprising Copolymer 1 or another random copolymer are formulated in accordance with routine procedures as pharmaceutical compositions adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together. Where the composition is to be administered by infusion, it can be dispensed with an infusion bottle containing sterile pharmaceutical grade water or saline, with the intervals between administrations being greater than 24 hours, 32 hours, or more preferably greater than 36 or 48 hours. Where the composition is administered by injection, an ampoule of sterile water or saline for injection can be provided so that the ingredients may be mixed prior to administration.

In certain embodiments, the methods described herein allow continuous treatment of autoimmune diseases by a sustained-release carrier such as transdermal patches, implantable medical devices coated with sustained-release formulations, or implantable or injectable pharmaceutical formulation suitable for sustained-release of the active components. In such embodiments, the intervals between administrations are preferably greater than 24 hours, 32 hours, or more preferably greater than 36 or 48 hours. For instance, an implantable device or a sustained released formulation which releases the copolymer over a 2 day period may the implanted every four days into the patient, such that the interval during which no copolymer is administered to the subject is 2 days. In related embodiments, the such interval where during which no administration occurs is at least 24+x hours, wherein x represents any positive integer.

In another embodiment, the random copolymers are formulated to have a therapeutic affect when administered to a subject in need thereof at time intervals of at least 24 hours. In a specific embodiment, the random copolymers are formulated for a long-lasting therapeutic affect such that a therapeutic effect in treating the disease is observed when the random copolymers are administered to the subject at time intervals of at least 24, 30, 36, 42, 48, 54, 60, 66, 72, 78, 84, 90, 96, 102, 108, 114, 120, 126, 132, 138, 144, 150, 156, 162, 168, 174, 180, 186, 192, 198, 204, 210, 216, 222, 228, 234, or 240 hours between administrations.

Another embodiment of the present invention is a method for prophylactically treating a subject at risk of developing e.g., an autoimmune disease by administering a random copolymer. A subject at risk is identified by, for example, determining the genetic susceptibility to an autoimmune disease by testing for alleles of HLA that are associated with such autoimmune disease, and/or based on familial history, or other genetic markers that correlate with such autoimmune disease. Such prophylactic treatment may additionally comprise a second copolymer that binds to a second HLA molecule associated with the autoimmune disease to be treated. The second HLA molecule may be a HLA-DQ or HLA-DR molecule. Preferably, the autoimmune disease to be prophylactically treated is IDDM or celiac disease.

In other embodiments of the methods described herein, additional therapeutically active agents are administered to the subject. In one embodiment, compositions comprising additional therapeutic agents(s) are administered to the subject as separate compositions from those comprising the random polymer. For example, a subject may be administered a composition comprising a random copolymer subcutaneously while a composition comprising another therapeutic agent may be administered orally. The additional therapeutically active agents may treat the same disease as the random copolymer, a related disease, or may be intended to treat an undesirable side effect of administration of the copolymer, such as to reduce swelling at a site of intradermal injection.

Additional therapeutically active agents which may be administered to the subject include copolymers which bind to a second HLA molecule associated with the disease, such as Copaxone™; an antibody, an enzyme inhibitor, an antibacterial agent, an antiviral agent, a steroid, a nonsteroidal anti-inflammatory agent, an antimetabolite, a cytokine, or a soluble cytokine receptor. The second HLA molecule may be an HLA-DQ molecule or an HLA-DR molecule. The enzyme inhibitor may be a protease inhibitor or a cyclooxygenase inhibitor.

In a further embodiment, the copolymers of the present invention are administered to a patient with an autoimmune disease following an anti-lymphocyte therapy (e.g., anti-T cell or anti-B cell). In one embodiment, anti-T cell therapies may use antibodies, such as Campath-1H® (alemtuzumab; anti-CD52), OKT3 (anti-CD3), thymoglobulin (anti-thymocytic globulins), or anti-IL2R antibodies (e.g., daclizumab and basiliximab). Alternatively, anti-T cell therapies may use chemotherapy agents such as fludarabine, external-beam radiation therapy (XRT), and cyclophosphamide. In another embodiment, the copolymers of the present invention may be combined with an anti-B cell therapy for treating an autoimmune disease, such as agents that react with CD20 such as the antibody Rituxan (Rituximab). The dosage of the above treatments to be administered to a patient will vary with the precise nature of the condition being treated and the recipient of the treatment. The scaling of dosages for human administration can be performed according to art-accepted practices. For example, the dose for Campath-1H® will generally be in the range 1 to about 100 mg for an adult patient, usually administered daily for a period between 1 and 30 days. The preferred daily dose is 1 to 10 mg per day although in some instances larger doses of up to 40 mg per day may be used (see, e.g., U.S. Pat. No. 6,120,766). Although not wishing to be bound by any particular mechanism or theory, it is believed that such combination therapy can enhance the therapeutic efficacy without any potential long-term toxicity. To illustrate, Campath-1H® is introduced in a patient for initial induction immunosuppression. Then, the patient is administered a copolymer of the present invention in the absence of Campath-1H®.

In other embodiments, a copolymer of the present invention can be administered with an anti-lymphocyte agent (e.g., anti-T cell or anti-B cell) either in the same formulation or in separate formulations, to enhance treatment. For example, a copolymer and an anti-lymphocyte agent can be administered at the same time (simultaneously) or at separate times (sequentially), provided that they are administered in such a manner and sufficiently close in time to have the desired effect.

The additional agent may be added as a part of the pharmaceutical composition, or may be administered concomitantly or within a time period when the physiological effect of the additional agent overlaps with the physiological effect of the copolymer of the present invention. More particularly, an additional agent may be administered concomitantly or one week, several days, 24 hours, 8 hours, or immediately before the administration of the copolymer. Alternatively, an additional agent may be administered one week, several days, 24 hours, 8 hours, or immediately after the administration of the copolymer.

An improvement in the symptoms of a subject afflicted with multiple sclerosis (MS) as a result of administration of the random copolymer may be noted by a decrease in frequency of recurrences of episodes of MS, by decrease in severity of symptoms, and by elimination of recurrent episodes for a period of time after the start of administration. A therapeutically effective dosage preferably reduces symptoms and frequency of recurrences by at least about 20%, for example, by at least about 40%, by at least about 60%, and by at least about 80%, or by about 100% elimination of one or more symptoms, or elimination of recurrences of the autoimmune disease, relative to untreated subjects. The period of time can be at least about one month, at least about six months, or at least about one year.

An improvement in the symptoms of a subject afflicted with arthritis or any other autoimmune disorder which results in inflammation of the joints may be noted by a reduction in edema of one or more joints, by a reduction in inflammation in one or more joints, or by an increase in mobility in one or more joints. A therapeutically effective dosage preferably reduces joint inflammation and edema and improves mobility by at least about 20%, more preferably by at least about 40%, even more preferably by at least about 60%, and even still more preferably by at least about 80%, relative to untreated subjects.

The contents of any patents, patent applications, patent publications, or scientific articles referenced anywhere in this application are herein incorporated in their entirety.

The practice of the present invention will employ, where appropriate and unless otherwise indicated, conventional techniques of cell biology, cell culture, molecular biology, transgenic biology, microbiology, virology, recombinant DNA, and immunology, which are within the skill of the art. Such techniques are described in the literature. See, for example, Molecular Cloning: A Laboratory Manual, 3rd Ed., ed. by Sambrook and Russell (Cold Spring Harbor Laboratory Press: 2001); the treatise, Methods In Enzymology (Academic Press, Inc., N.Y.); Using Antibodies, Second Edition by Harlow and Lane, Cold Spring Harbor Press, New York, 1999; Current Protocols in Cell Biology, ed. by Bonifacino, Dasso, Lippincott-Schwartz, Harford, and Yamada, John Wiley and Sons, Inc., New York, 1999; and PCR Protocols, ed. by Bartlett et al., Humana Press, 2003.

VII. EXAMPLES

Example 1

Production of Antibodies Against Random Copolymers and a Disease-Associated Antigen Peptide PLP(139-151) peptide is the major immunogenic determinant recognized by CD4$^+$ T$_H$1 cells which in turn drive EAE development in SJL mice. When injected with pertussis toxin, PLP (139-151) peptide causes MS-like symptoms in the SJL mice. In the absence of the pertussis toxin, injected animals develop only mild and transient disease. The ability of random copolymer compositions to protect the animals from the effect of PLP injection was evaluated in the course of daily and weekly dosing of the animals after their exposure to PLP (139-151) peptide. Antibody isotypes were also examined. CD4 T cells can be divided into at least two different subsets depending on the pattern of their cytokine production. T$_H$1 cells preferentially produce IL-2 and IFN-γ, activate macrophages, and stimulate production of the Ig subclasses IgG2a and IgG3 in mice and IgG1 and IgG3 in humans. In contrast, the signature cytokines of T$_H$2 cells are IL-4, IL-5, and IL-13, which provide potent B cell help and induce isotype switching to IgE and IgG1 in mice or to IgE, IgG2, and IgG4 in humans. Therefore, mouse IgG1 and IgG2b, generally associated with T$_H$2 response, and mouse IgG2a, markers of T$_H$1 immunity, were measured.

Mice (SJL, female) were immunized on day 1 with 100 μg of PLP(139-151) peptide in Complete Freund's adjuvant. The same day, the animals received an intravenous injection of 200 ng of pertussis toxin. On day 3, the same IV injection was repeated. Treatment with Copaxone™ (YEAK) or Co-14 (YFAK), 7.5 mg/kg, daily and weekly was started on day 6 and continued daily until day 36. On day 37, individual sera were collected and antibody response against PLP (139-151) peptide, Co-14 (YFAK), and Copaxone™ were measured using standard ELISA with anti-mouse total Ig, IgG1, IgG2a or IgG2b as secondary antibody.

During the course of the experiment, disease severity was measured using a standard scoring system between 0 (no disease) and 5 (moribund), and body weight of a mouse was recorded as another measure of disease state. The mortality rate of the animals was recorded daily.

Figure 2:
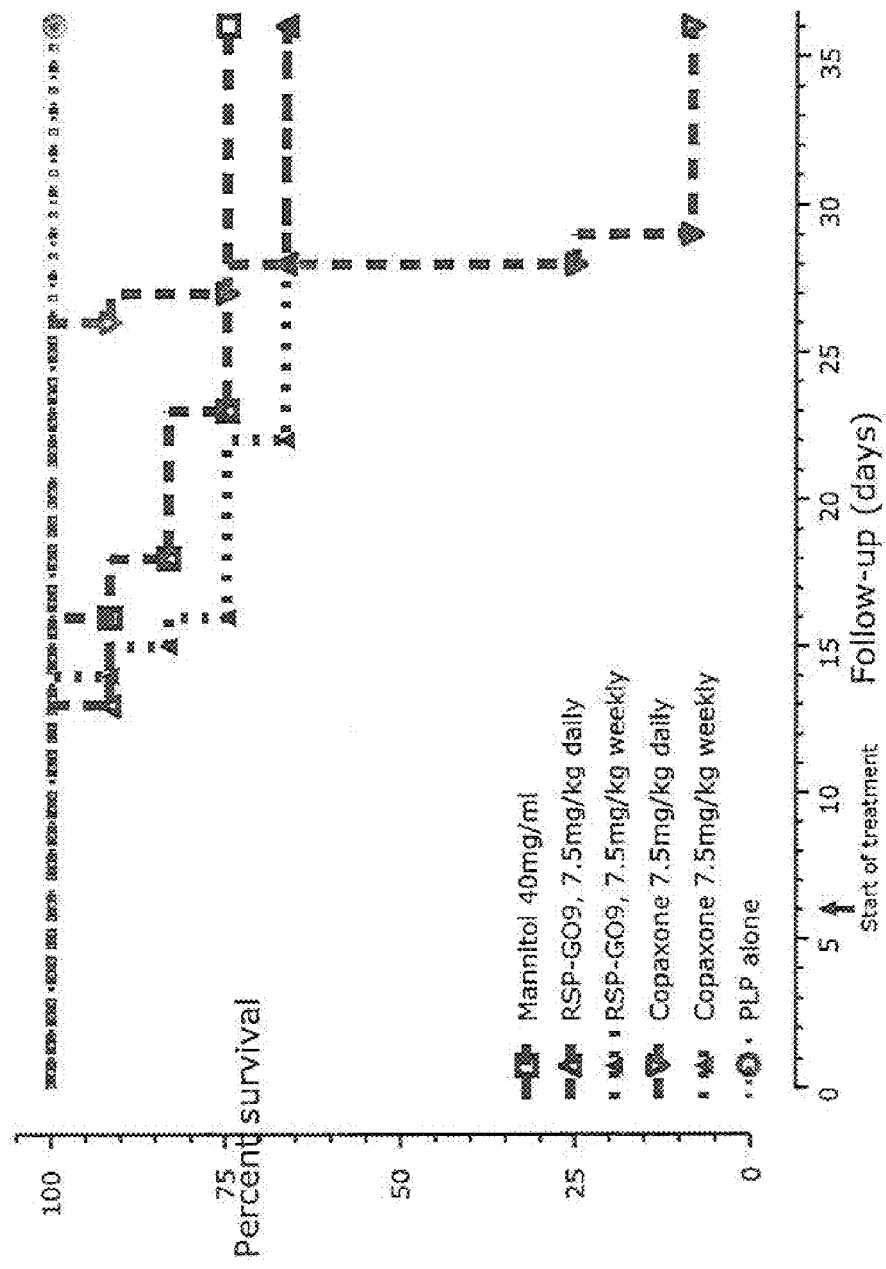
FIG. 2. shows the survival rate of mice with EAE when administered with random copolymers.
Figure 3:
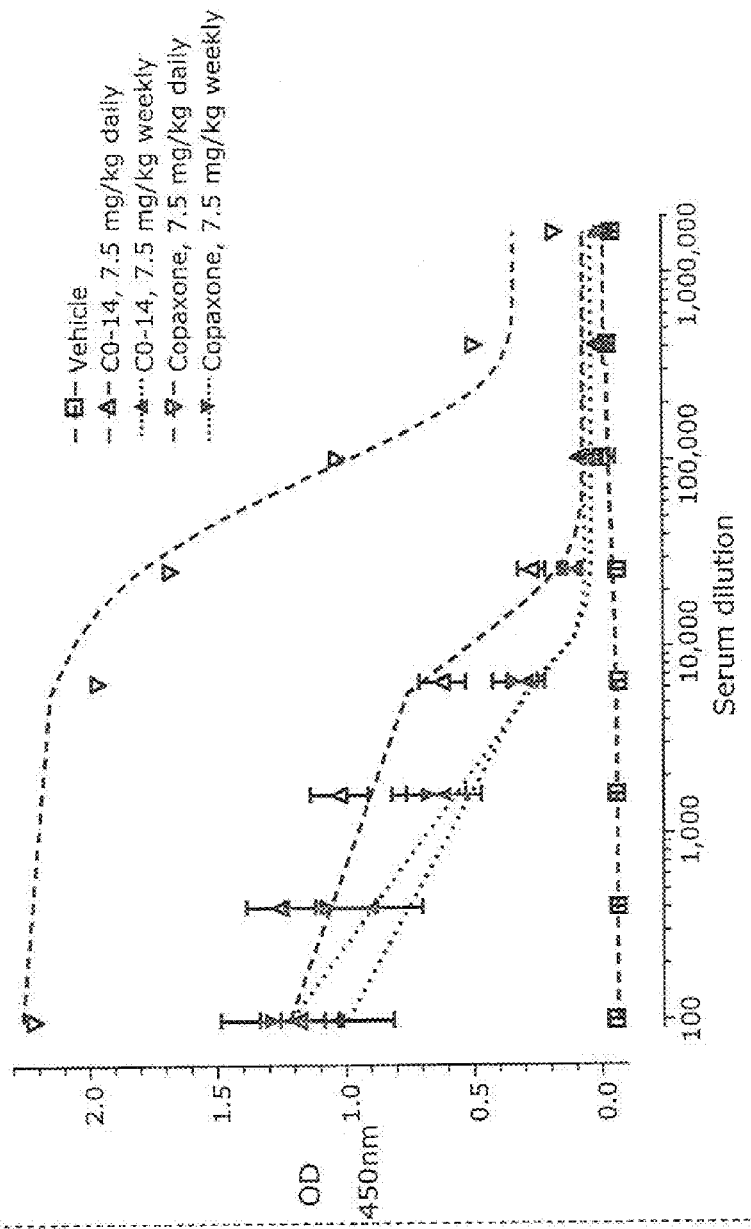
FIG. 3 shows IgG antibody production against copolymers administered at daily or weekly doses.
Figure 4:
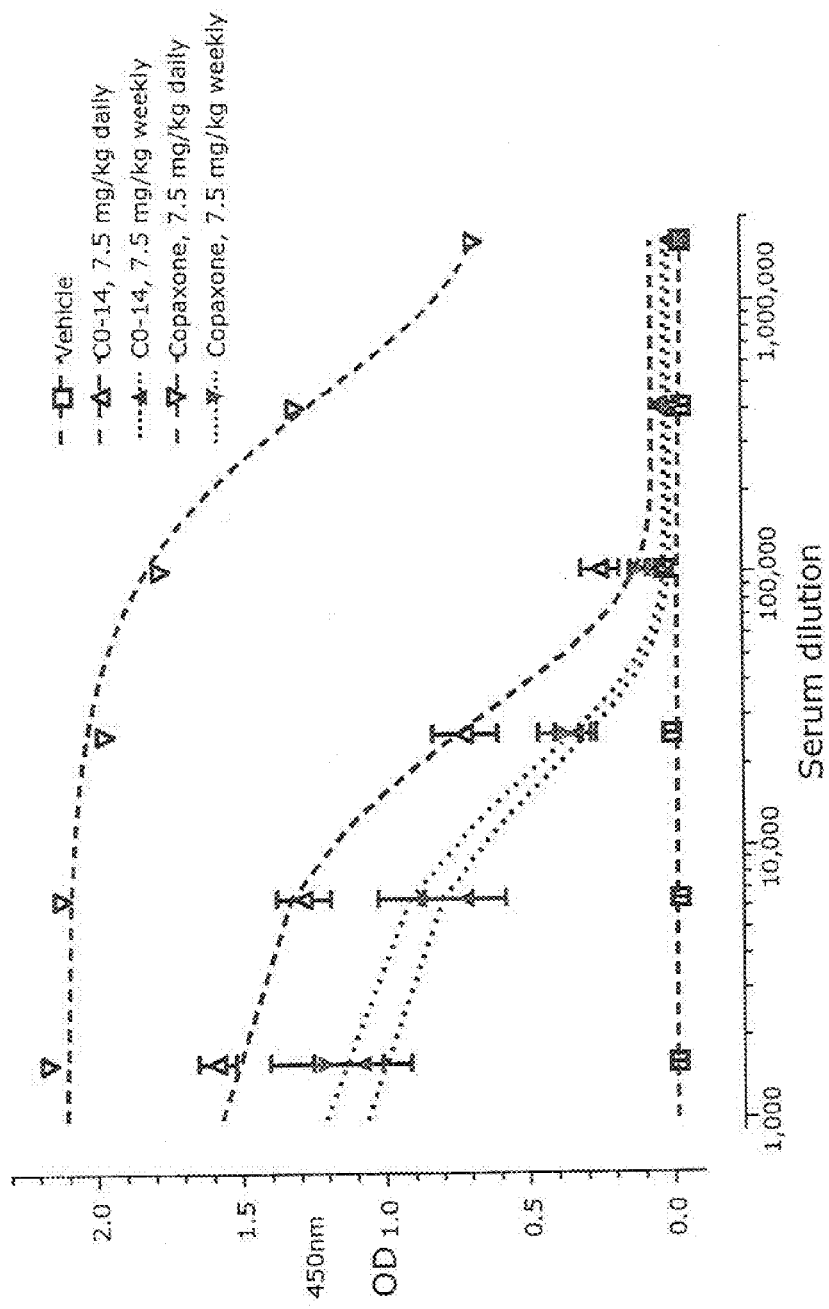
FIG. 4 shows IgG1 antibody production against copolymers administered at daily or weekly doses.
Figure 5:
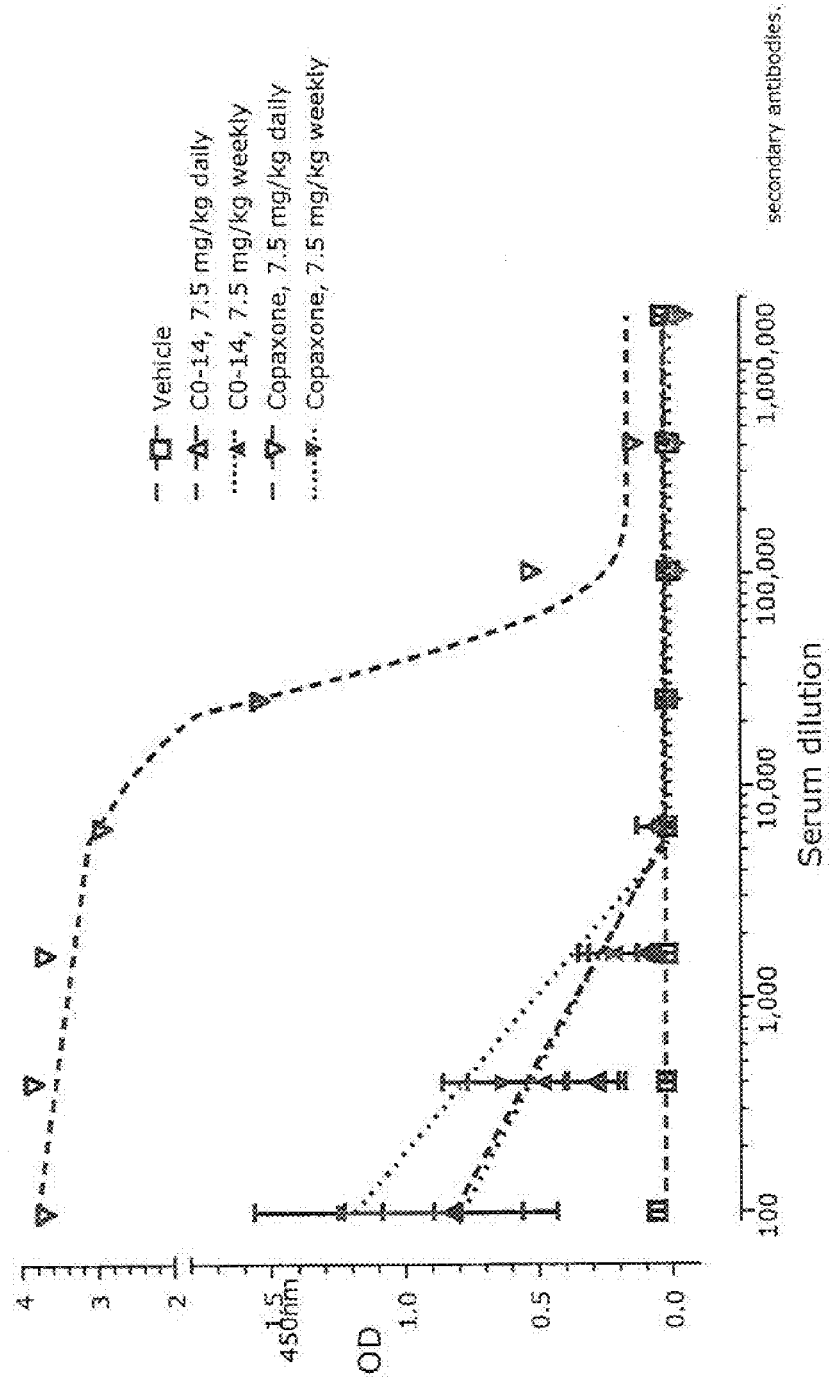
FIG. 5 shows IgG2b antibody production against copolymers administered at daily or weekly doses.
Figure 6:
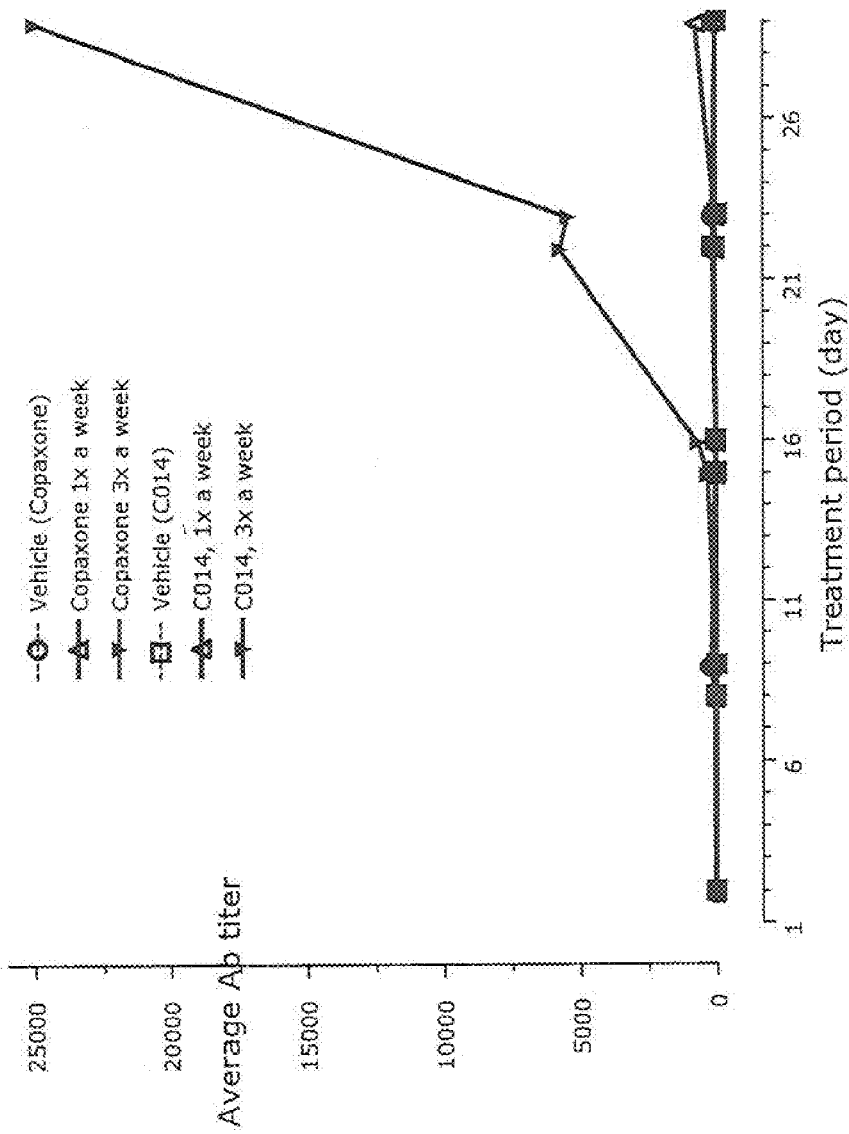
FIG. 6 shows the changes in antibody titer against copolymers during the time course of a treatment.

Although daily dosing of Copaxone™ was effective in reducing the severity of the disease compared to mannitol dosing alone (FIG. 1), majority of the mice treated with daily dose of Copaxone™ died suddenly after about 3 weeks of treatment (FIG. 2). As shown in FIG. 3, daily dosing of Copaxone™ induced a large amount of antibodies in the surviving injected mice. In contrast, weekly dosing with Copaxone™, and daily and weekly dosing with Co-14 (YFAK), resulted in much lower antibody titers. The immune response was predominantly IgG1+IgG2b (i.e., predominantly T$_H$2) responses, and a much lower IgG2a (i.e. T$_H$1) response was seen. The few surviving mice in Copaxone™ daily group had large IgG1 and IgG2b response against compound (FIGS. 4 and 5), raising the possibility that the cause of death in Copaxone™ daily dosed mice is likely to be anaphylaxis. In contrast, weekly dosing with Copaxone™, and daily and weekly dosing with Co-14 (YFAK), which showed a much lower antibody titers, prevented anaphylactic shock and increased efficacy. Another example of antibody titers is shown in FIG. 6, where Copaxone™ and Co-14 (YFAK) were administered either once a week or 3 times a week. Copaxone™, when administered 3 times a week, induces production of large amount of antibodies directed against it, whereas weekly dosing of Copaxone™ and dosing of Co-14, either weekly or three times a week, do not induce appreciative amount of antibodies against the respective copolymers.

Figure 7:
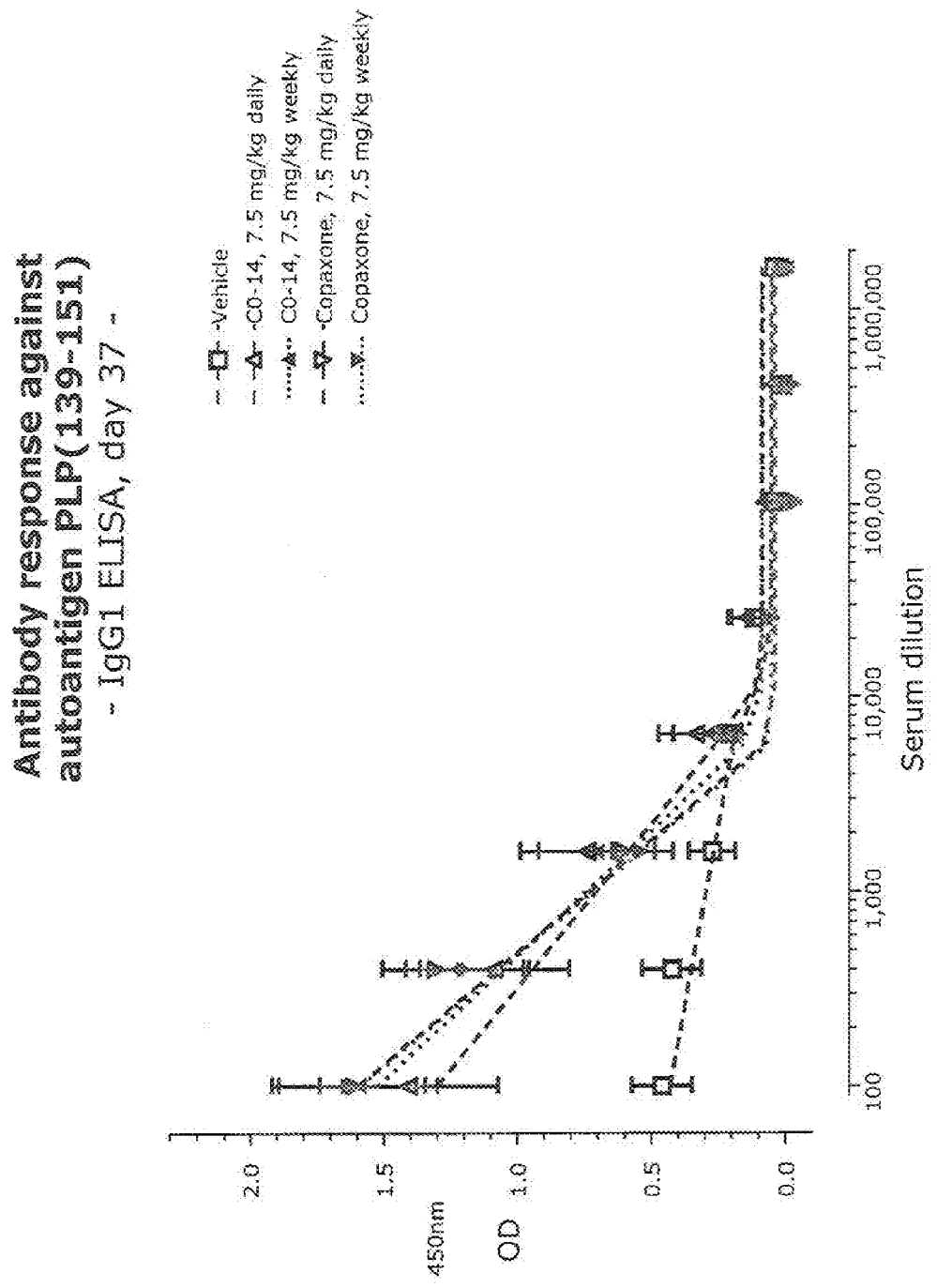
FIG. 7 shows the IgG1 antibody production against PLP peptide in mice administered with random copolymers.
Figure 8:
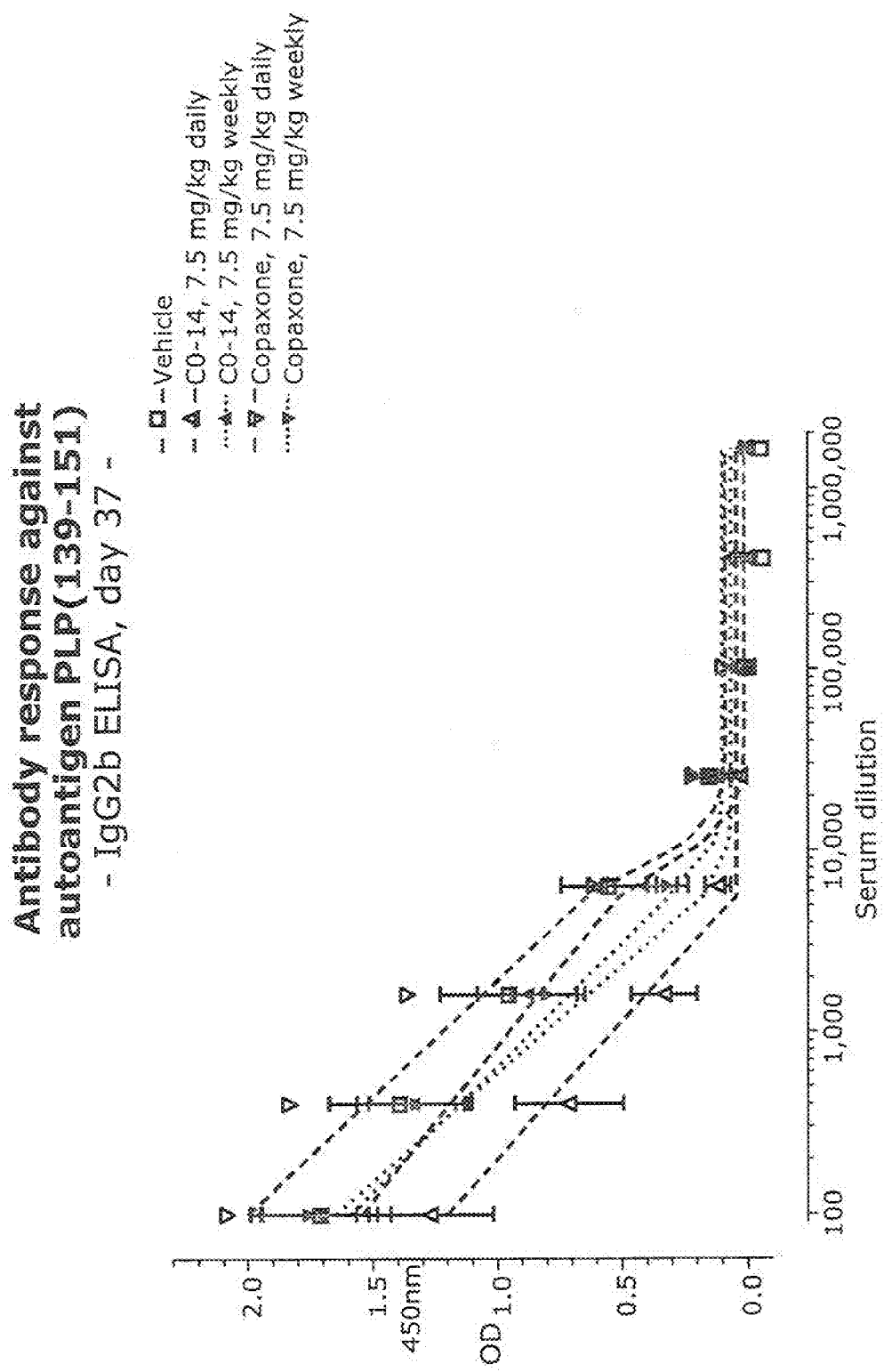
FIG. 8 shows the IgG2b antibody production against PLP peptide in mice administered with random copolymers.

When antibody titers for PLP (139-151) peptide were measured, both Copaxone™ and Co-14 (YFAK), regardless of dosing interval, induced similar, small increases in amounts of IgG1 formation against PLP (139-151) peptide (FIG. 7) compared to dosing with vehicle alone. The titers of IgG2b against PLP (139-151) were also not significantly affected (FIG. 8). These results show that the protective effect of Copaxone™ or Co-14 (YFAK) is not exerted through modulation of antibody amounts against PLP (139-151) peptide.

Example 2

T Cell Response to Random Copolymers

The T$_H$1 and T$_H$2 profiles of mice injected with 5 μg Copaxone™ or Co-14 (YFAK) three times a week or on weekly bases, up to day 22 of the treatment. On day 2, 8, 9, 15, 16, 22, 23, 29, spleens were collected and splenocytes were isolated. 400,000 cells per well of splenocytes were restimulated with various concentrations (0.8, 4, or 20 μg/ml) of Co-14 (YFAK) for three days. On day 3 of the cell culture, the cells were transferred onto ELISPOT (enzyme-linked immunospot assay) plates, coated with either IFN-γ (interferon gamma) or IL-13 (interleukin 13). The T cell response is examined by measuring the IFN γ production (a T$_H$1 cytokine) and IL-13 production (a T$_H$2 cytokine). The degree of T cell stimulation is also examined by measuring the proliferation of the cells shown as tritiated thymidine intake.

Figure 9:
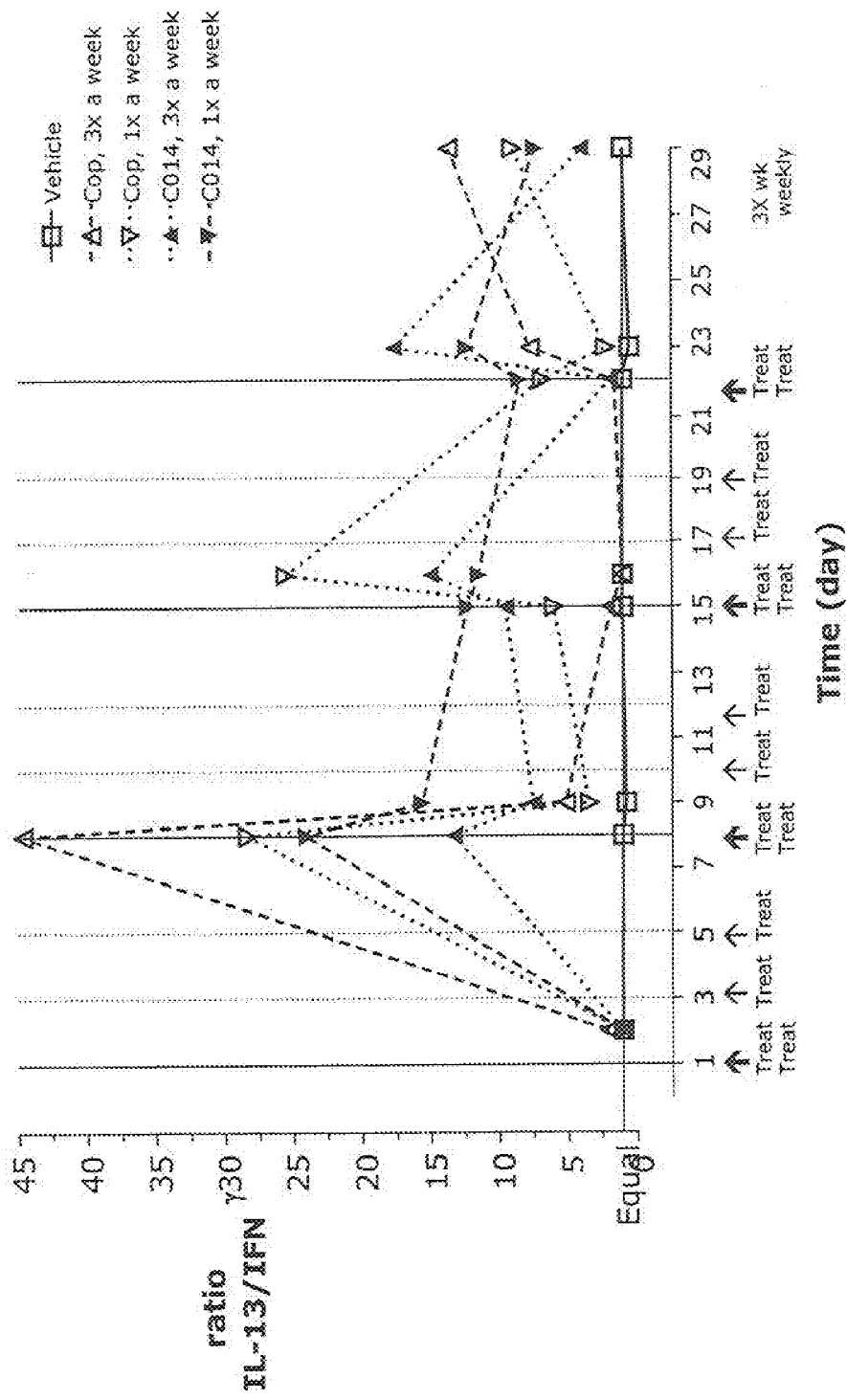
FIG. 9 shows the ratio of IL-13 over IFN γ in mice administered with random copolymers.
Figure 10:
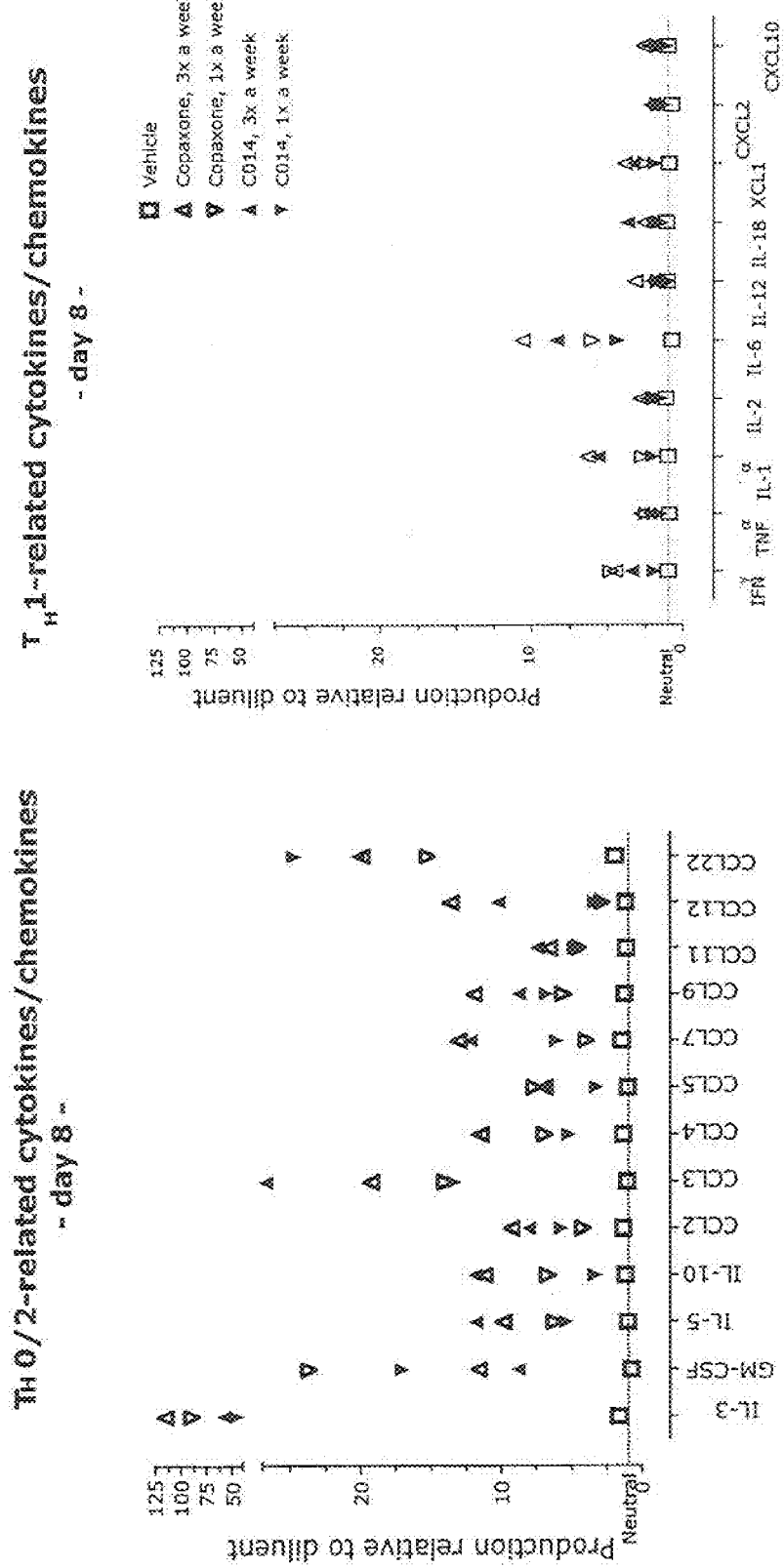
FIG. 10 shows the bias for induction of $T_H2$ related cytokines compared to $T_H1$ related cytokines in mice administered with random copolymers.
Figure 11:
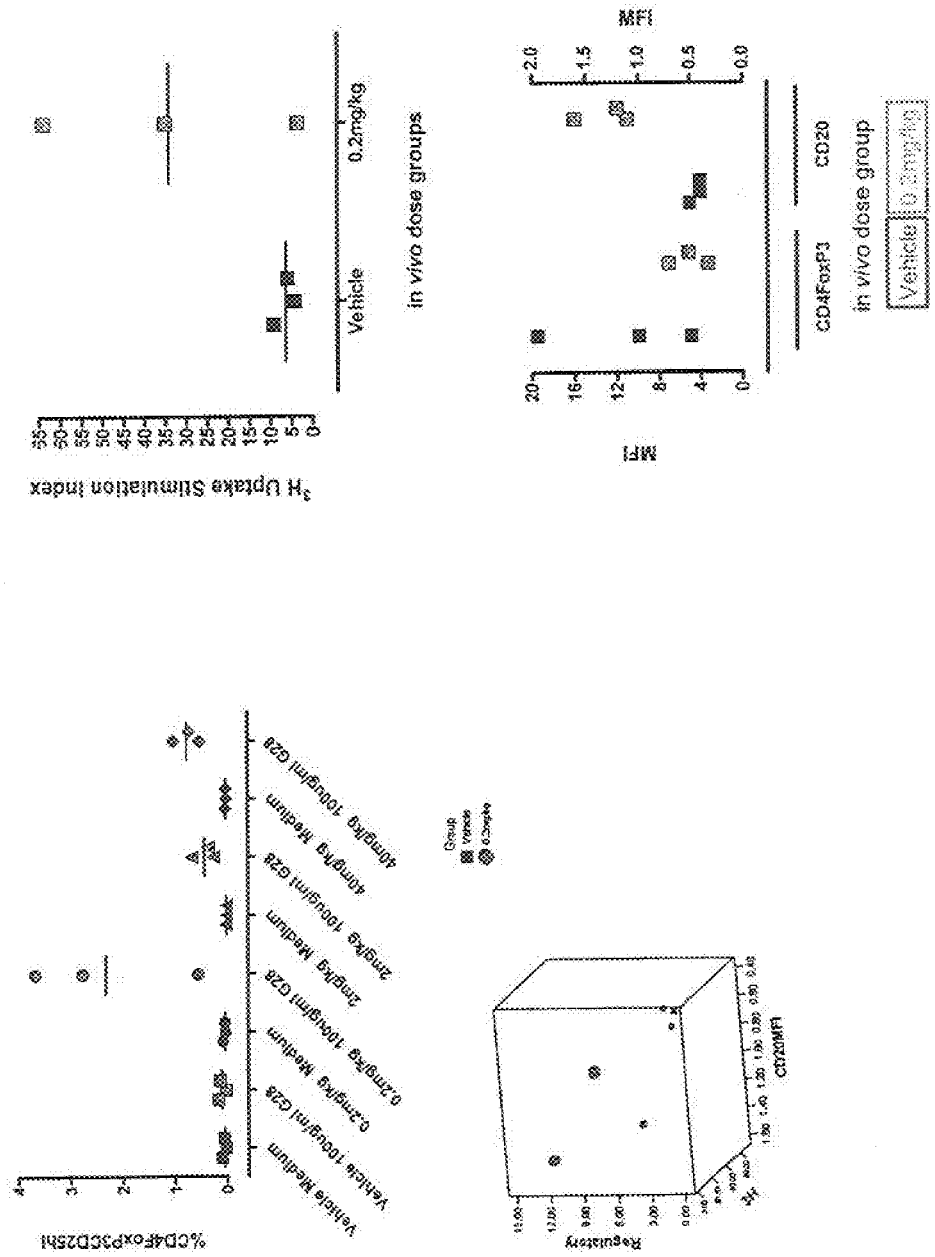
FIG. 11 shows the ability of Co-14 to generate specific effects upon T and B cells.
Figure 12:
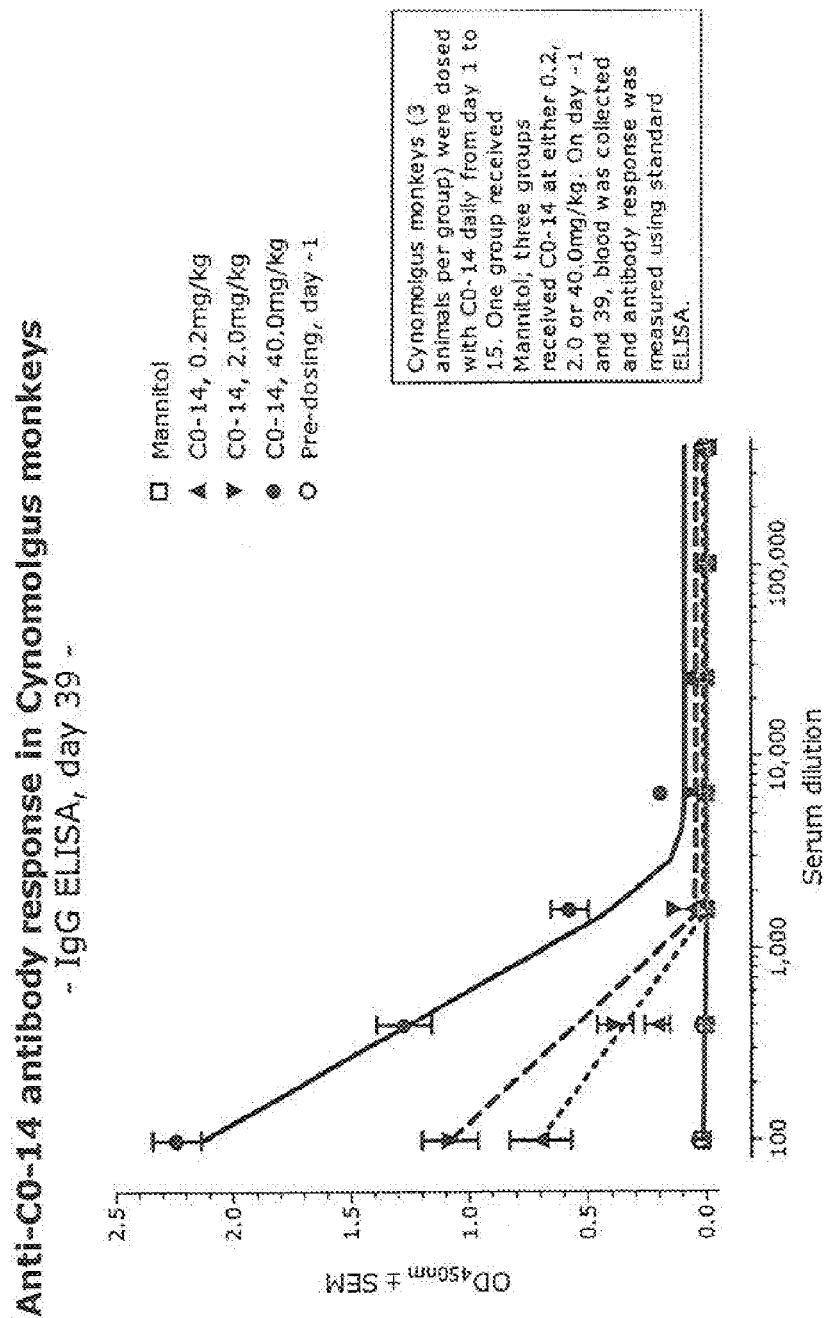
FIG. 12 shows the dose dependent antibody response (IgG) to Co-14.
Figure 13A:
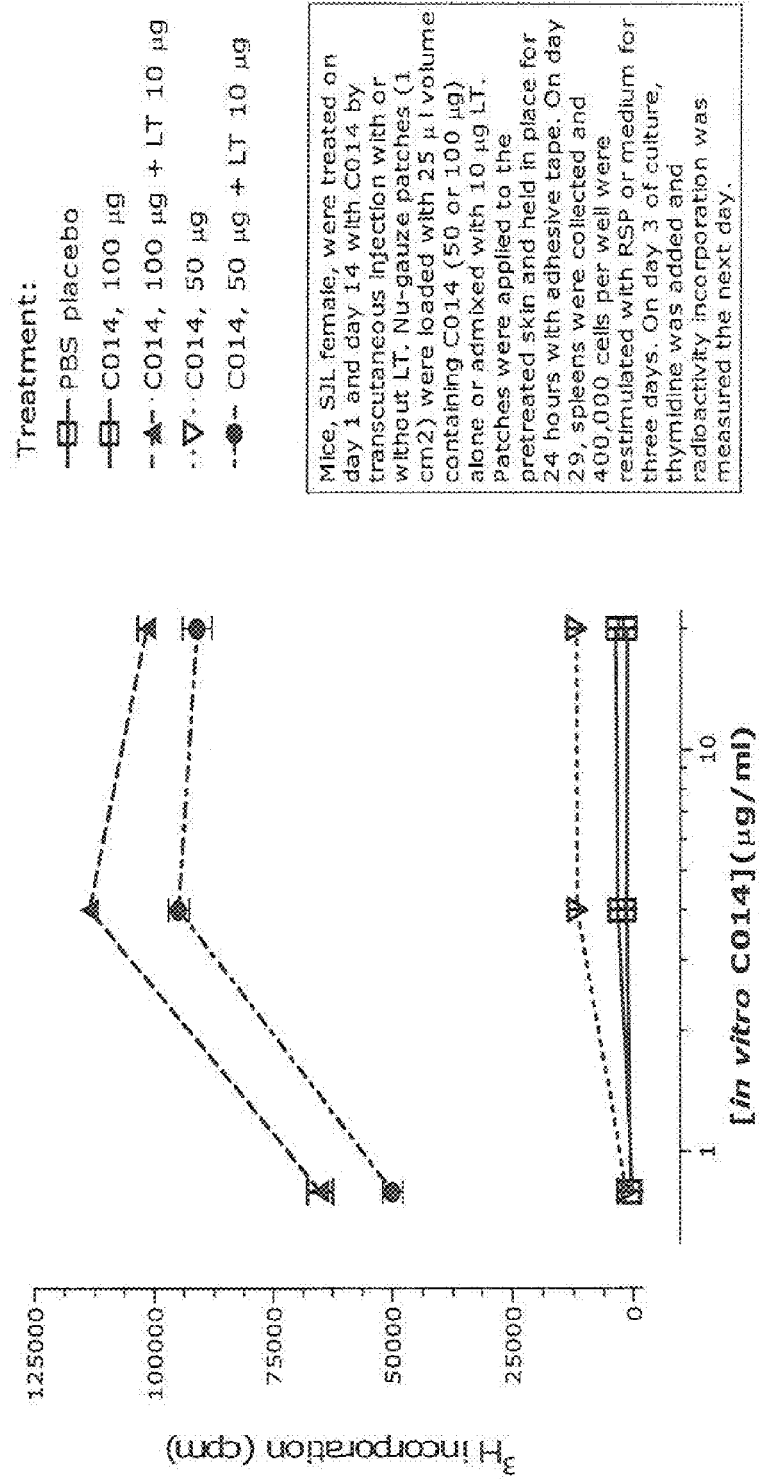
Figure 15:
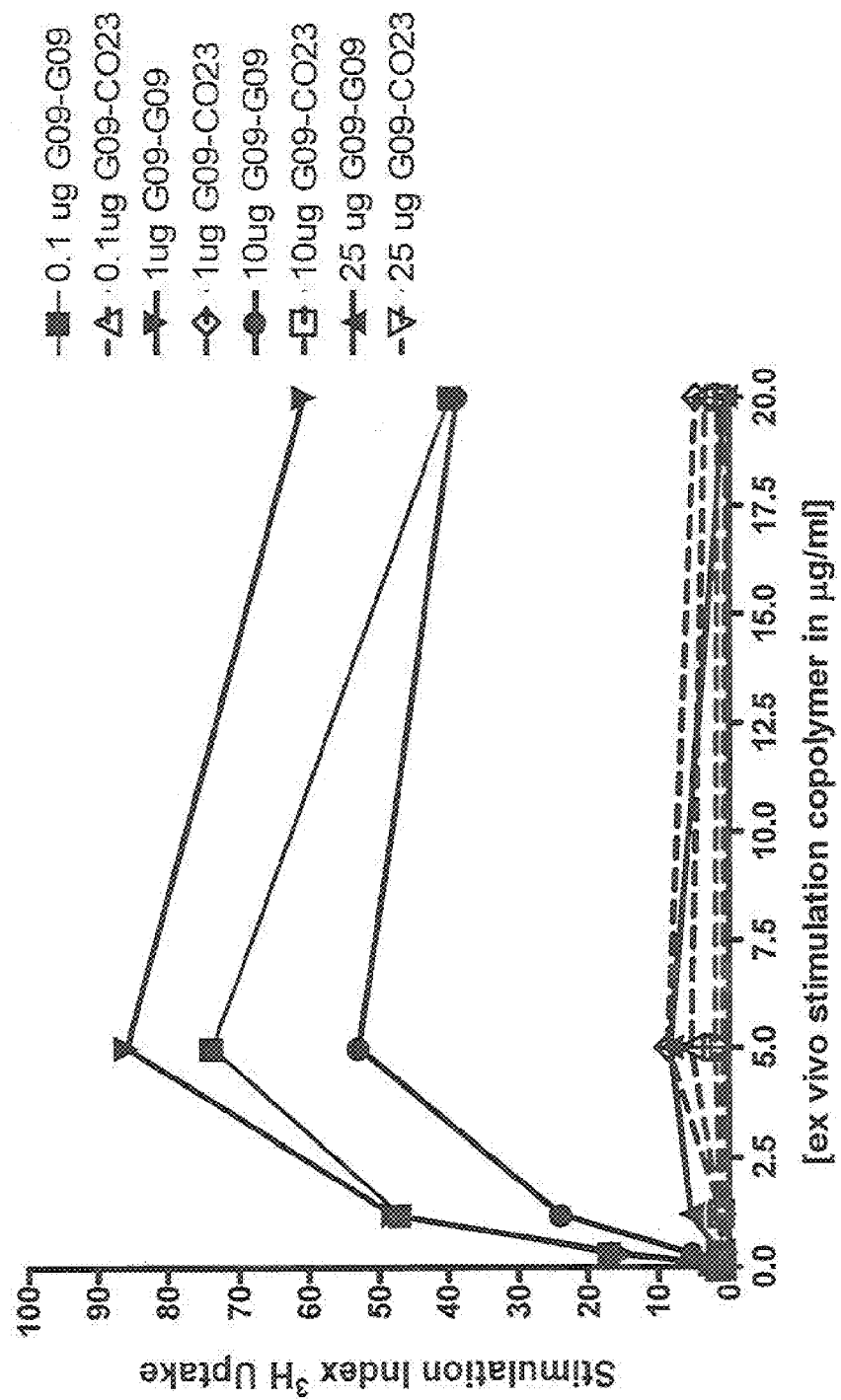
FIG. 15 shows the ability of the proper ratio of YFAK within the Co-14 RSP to generate a recall response in a NOD mouse.

A burst of response was seen in the first week of dosing, followed by a decreased but sustained response. As seen in FIG. 9, the response is T$_H$2 biased, with the IL-13 production induced more strongly than the IFN-γ at all times in cells treated with either Copaxone™ or Co-14 (YFAK). The T$_H$2 bias is further confirmed by the amount of 23 cytokines and chemokines, as seen in FIG. 10.

What is claimed is:

1. A method of reducing the severity of one or more symptoms of multiple sclerosis comprising the step of administering to a subject in need thereof an effective amount of a random copolymer composition, wherein said effective amount is delivered to said subject in two or more doses, each additional dose after the first dose being administered at least one week after the conclusion of administration of the immediately preceding dose, and wherein the random copolymer composition comprises YFAK (L-tyrosine, L-phenylalanine, L-alanine and L-lysine) in an output molar ratio of about 1.0:1.2:XA:6.0 respectively, and has a length of at least 35 amino acids wherein XA=18.0 to 30.0.

2. The method of claim 1, wherein the random copolymer composition comprises YFAK (L-tyrosine, L-phenylalanine, L-alanine and L-lysine) in an output molar ratio of about 1.0:1.2:XA:6.0 respectively, and has a length of at least 35 amino acids wherein the composition is selected from the group consisting of:

(a) a random copolymer composition comprising YFAK (L-tyrosine, L-phenylalanine, L-alanine and L-lysine) in an output molar ratio of about 1.0:1.2:20:6.0 respectively, and has a length of at least 35 amino acids; and (b) a random copolymer composition comprising YFAK (L-tyrosine, L-phenylalanine, L-alanine and L-lysine) in an output molar ratio of about 1.0:1.2:22:6.0 respectively, and has a length of at least 35 amino acids; and (c) a random copolymer composition comprising YFAK (L-tyrosine, L-phenylalanine, L-alanine and L-lysine) in an output molar ratio of about 1.0:1.2:24:6.0 respectively, and has a length of at least 35 amino acids.

3. The method of claim 1, wherein the multiple sclerosis is relapsing-remitting multiple sclerosis.

4. The method of claim 1, wherein the subject is a human.

5. The method of claim 1, wherein the effective amount of the random copolymer is between 0.02 mg per dose and 2000 mg per dose.

6. The method of claim 1, wherein the effective amount is about 1 mg.

7. The method of claim 1, wherein the random copolymer composition is administered in a dosing regimen comprising a dose of between 10 and 65 mg per $m^2$ of the body surface area of the subject per dose.

8. The method of claim 7, wherein the dosing regimen comprises a dose of about 22 mg per m² of the body surface area of the subject per dose.

9. The method of claim 1, wherein the random copolymer composition is administered in a dosing regimen comprising a dose of between about 0.05 mg and 0.4 mg per kg of the body weight of the subject per dose.

10. The method of claim 1, wherein the random copolymer composition is administered in a dosing regimen comprising a maximum dose of about 140 mg per m² of the body surface area of the subject weekly.

11. The method of claim 1, wherein the random copolymer composition is administered in a dosing regimen comprising a dose of between 0.35 and 2.8 mg per kg of the body weight of the subject weekly.

12. The method of claim 1, wherein the dosing regimen comprises continuous administration of the random copolymer composition.

13. The method of claim 12, wherein the administration of the random copolymer composition is via devices designed to deliver the random copolymer composition continuously.

14. The method of claim 13, wherein the device is an implantable device, a sustained release capsule, controlled release formulation, or a pump.

15. The method of claim 12, wherein said effective amount is delivered to the subject using a sustained-release formulation which administers the random copolymer over a period of at least 3 days.

16. The method of claim 1, further comprising administering an additional therapeutically active agent to the subject.

17. The method of claim 16, wherein the additional agent is one or more random copolymers useful in treating multiple sclerosis.

18. The method of claim 16, wherein the additional agent is an anti-inflammatory agent.

19. The method of claim 1, further comprising administering to said subject a T-cell depletion therapy.

20. The method of claim 1, further comprising administering to said subject an anti-lymphocyte therapy.

21. The method of claim 20, wherein said anti-lymphocyte therapy comprises administering an agent selected from the group consisting of a polyclonal antibody and a monoclonal antibody.

22. The method of claim 21, wherein said polyclonal antibody is antithymocyte gamma globulin (ATGAM).

23. The method of claim 21, wherein said monoclonal antibody is selected from the group consisting of alemtuzumab, muromonab, daclizumab, and basiliximab.

24. The method of claim 1, further comprising administering to said subject an anti B-cell therapy.

25. The method of claim 24, wherein said anti-B-cell therapy comprises administering anti CD-20 antibody.

26. A method for decreasing the frequency of recurrences of episodes of multiple sclerosis comprising the step of administering to a subject in need thereof an effective amount of a random copolymer composition, wherein said effective amount is delivered to said subject in two or more doses, each additional dose after the first dose being administered at least one week after the administration of the immediately preceding dose, and wherein the random copolymer composition comprises YFAK (L-tyrosine, L-phenylalanine, L-alanine and L-lysine) in an output molar ratio of about 1.0:1.2:XA:6.0 respectively, and has a length of at least 35 amino acids wherein XA=18.0 to 30.0.

27. The method of claim 26, wherein the random copolymer composition comprises YFAK (L-tyrosine, L-phenylalanine, L-alanine and L-lysine) in an output molar ratio of about 1.0:1.2:XA:6.0 respectively, and has a length of at least 35 amino acids wherein the composition is selected from the group consisting of:
(a) a random copolymer composition comprising YFAK (L-tyrosine, L-phenylalanine, L-alanine and L-lysine) in an output molar ratio of about 1.0:1.2:20:6.0 respectively, and has a length of at least 35 amino acids;
(b) a random copolymer composition comprising YFAK (L-tyrosine, L-phenylalanine, L-alanine and L-lysine) in an output molar ratio of about 1.0:1.2:22:6.0 respectively, and has a length of at least 35 amino acids; and
(c) a random copolymer composition comprising YFAK (L-tyrosine, L-phenylalanine, L-alanine and L-lysine) in an output molar ratio of about 1.0:1.2:24:6.0 respectively, and has a length of at least 35 amino acids.

28. The method according to claim 1, wherein the effective amount is delivered subcutaneously.

29. The method according to claim 26, wherein the effective amount is delivered subcutaneously.

* * * * *

```
                         SEQUENCE LISTING

<160> NUMBER OF SEQ ID NOS: 49

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ala Ala Ala Tyr Ala Ala Ala Ala Ala Ala Lys Ala Ala Ala Ala
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ala Glu Lys Tyr Ala Ala Ala Ala Ala Ala Lys Ala Ala Ala Ala
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Lys Glu Tyr Ala Ala Ala Ala Ala Ala Lys Ala Ala Ala Ala
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ala Lys Lys Tyr Ala Ala Ala Ala Ala Ala Lys Ala Ala Ala Ala
1               5                   10                  15

<210> SEQ ID NO 5
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 5

Ala Glu Ala Tyr Ala Ala Ala Ala Ala Lys Ala Ala Ala Ala
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Lys Glu Ala Tyr Ala Ala Ala Ala Ala Lys Ala Ala Ala Ala
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ala Glu Glu Tyr Ala Ala Ala Ala Ala Lys Ala Ala Ala Ala
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ala Ala Glu Tyr Ala Ala Ala Ala Ala Lys Ala Ala Ala Ala
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Glu Lys Ala Tyr Ala Ala Ala Ala Ala Lys Ala Ala Ala Ala
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ala Ala Lys Tyr Glu Ala Ala Ala Ala Lys Ala Ala Ala Ala
1               5                   10                  15
```

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ala Ala Lys Tyr Ala Glu Ala Ala Ala Lys Ala Ala Ala Ala
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Glu Ala Ala Tyr Ala Ala Ala Ala Ala Lys Ala Ala Ala Ala
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Glu Lys Lys Tyr Ala Ala Ala Ala Ala Lys Ala Ala Ala Ala
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Glu Ala Lys Tyr Ala Ala Ala Ala Ala Lys Ala Ala Ala Ala
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ala Glu Lys Tyr Ala Ala Ala Ala Ala Ala Ala Ala Ala Ala
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 16

Ala Lys Glu Tyr Ala Ala Ala Ala Ala Ala Ala Ala Ala Ala Ala
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ala Lys Lys Tyr Glu Ala Ala Ala Ala Ala Ala Ala Ala Ala Ala
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ala Lys Lys Tyr Ala Glu Ala Ala Ala Ala Ala Ala Ala Ala Ala
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ala Glu Ala Tyr Lys Ala Ala Ala Ala Ala Ala Ala Ala Ala Ala
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Lys Glu Ala Tyr Ala Ala Ala Ala Ala Ala Ala Ala Ala Ala Ala
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ala Glu Glu Tyr Lys Ala Ala Ala Ala Ala Ala Ala Ala Ala Ala
1               5                   10                  15

<210> SEQ ID NO 22
<211> LENGTH: 15
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 22

Ala Ala Glu Tyr Lys Ala Ala Ala Ala Ala Ala Ala Ala Ala Ala
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Glu Lys Ala Tyr Ala Ala Ala Ala Ala Ala Ala Ala Ala Ala Ala
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ala Ala Lys Tyr Glu Ala Ala Ala Ala Ala Ala Ala Ala Ala Ala
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ala Ala Lys Tyr Ala Glu Ala Ala Ala Ala Ala Ala Ala Ala Ala
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Glu Lys Lys Tyr Ala Ala Ala Ala Ala Ala Ala Ala Ala Ala Ala
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Glu Ala Lys Tyr Ala Ala Ala Ala Ala Ala Ala Ala Ala Ala Ala
1               5                   10                  15

-continued

<210> SEQ ID NO 28
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ala Glu Tyr Ala Lys Ala Ala Ala Ala Ala Ala Ala Ala Ala Ala
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ala Glu Lys Ala Tyr Ala Ala Ala Ala Ala Ala Ala Ala Ala Ala
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Glu Lys Tyr Ala Ala Ala Ala Ala Ala Ala Ala Ala Ala Ala Ala
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ala Tyr Lys Ala Glu Ala Ala Ala Ala Ala Ala Ala Ala Ala Ala
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ala Lys Tyr Ala Glu Ala Ala Ala Ala Ala Ala Ala Ala Ala Ala
1               5                   10                  15

<210> SEQ ID NO 33
<211> LENGTH: 104
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<221> NAME/KEY: MOD_RES
<222> LOCATION: (1)..(2)
<223> OTHER INFORMATION: Ala, Ser, Val, Lys or Pro
<220> FEATURE:
<221> NAME/KEY: MOD_RES
<222> LOCATION: (4)..(10)
<223> OTHER INFORMATION: Ala, Ser, Val, Lys or Pro
<220> FEATURE:
<221> NAME/KEY: MOD_RES
<222> LOCATION: (12)..(15)
<223> OTHER INFORMATION: Ala, Ser, Val, Lys or Pro
<220> FEATURE:
<221> NAME/KEY: MOD_RES
<222> LOCATION: (17)..(23)
<223> OTHER INFORMATION: Ala, Ser, Val, Lys or Pro
<220> FEATURE:
<221> NAME/KEY: MOD_RES
<222> LOCATION: (25)..(28)
<223> OTHER INFORMATION: Ala, Ser, Val, Lys or Pro
<220> FEATURE:
<221> NAME/KEY: MOD_RES
<222> LOCATION: (30)..(36)
<223> OTHER INFORMATION: Ala, Ser, Val, Lys or Pro
<220> FEATURE:
<221> NAME/KEY: MOD_RES
<222> LOCATION: (38)..(41)
<223> OTHER INFORMATION: Ala, Ser, Val, Lys or Pro
<220> FEATURE:
<221> NAME/KEY: MOD_RES
<222> LOCATION: (43)..(49)
<223> OTHER INFORMATION: Ala, Ser, Val, Lys or Pro
<220> FEATURE:
<221> NAME/KEY: MOD_RES
<222> LOCATION: (51)..(54)
<223> OTHER INFORMATION: Ala, Ser, Val, Lys or Pro
<220> FEATURE:
<221> NAME/KEY: MOD_RES
<222> LOCATION: (56)..(62)
<223> OTHER INFORMATION: Ala, Ser, Val, Lys or Pro
<220> FEATURE:
<221> NAME/KEY: MOD_RES
<222> LOCATION: (64)..(67)
<223> OTHER INFORMATION: Ala, Ser, Val, Lys or Pro
<220> FEATURE:
<221> NAME/KEY: MOD_RES
<222> LOCATION: (69)..(75)
<223> OTHER INFORMATION: Ala, Ser, Val, Lys or Pro
<220> FEATURE:
<221> NAME/KEY: MOD_RES
<222> LOCATION: (77)..(80)
<223> OTHER INFORMATION: Ala, Ser, Val, Lys or Pro
<220> FEATURE:
<221> NAME/KEY: MOD_RES
<222> LOCATION: (82)..(88)
<223> OTHER INFORMATION: Ala, Ser, Val, Lys or Pro
<220> FEATURE:
<221> NAME/KEY: MOD_RES
<222> LOCATION: (90)..(93)
<223> OTHER INFORMATION: Ala, Ser, Val, Lys or Pro
<220> FEATURE:
<221> NAME/KEY: MOD_RES
<222> LOCATION: (95)..(101)
<223> OTHER INFORMATION: Ala, Ser, Val, Lys or Pro
<220> FEATURE:
<221> NAME/KEY: MOD_RES
<222> LOCATION: (103)..(104)
<223> OTHER INFORMATION: Ala, Ser, Val, Lys or Pro
<220> FEATURE:
<223> OTHER INFORMATION: This sequence may encompass 1 to 8 13-mer
      repeating units; see specification as filed for detailed
      description of preferred embodiments

<400> SEQUENCE: 33

Xaa Xaa Glu Xaa Xaa Xaa Xaa Xaa Xaa Xaa Glu Xaa Xaa Xaa Xaa Glu
1               5                   10                  15

Xaa Xaa Xaa Xaa Xaa Xaa Xaa Glu Xaa Xaa Xaa Xaa Glu Xaa Xaa Xaa
```

```
                    20                  25                  30
Xaa Xaa Xaa Xaa Glu Xaa Xaa Xaa Xaa Glu Xaa Xaa Xaa Xaa Xaa
        35                  40                  45

Xaa Glu Xaa Xaa Xaa Xaa Glu Xaa Xaa Xaa Xaa Xaa Xaa Glu Xaa
    50                  55                  60

Xaa Xaa Xaa Glu Xaa Xaa Xaa Xaa Xaa Xaa Glu Xaa Xaa Xaa Xaa
65                  70                  75                  80

Glu Xaa Xaa Xaa Xaa Xaa Xaa Xaa Glu Xaa Xaa Xaa Xaa Glu Xaa
                85                  90                  95

Xaa Xaa Xaa Xaa Xaa Glu Xaa Xaa
                100

<210> SEQ ID NO 34
<211> LENGTH: 104
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Ala, Ser, Val, Lys or Pro
<220> FEATURE:
<221> NAME/KEY: MOD_RES
<222> LOCATION: (4)..(10)
<223> OTHER INFORMATION: Ala, Ser, Val, Lys or Pro
<220> FEATURE:
<221> NAME/KEY: MOD_RES
<222> LOCATION: (12)..(15)
<223> OTHER INFORMATION: Ala, Ser, Val, Lys or Pro
<220> FEATURE:
<221> NAME/KEY: MOD_RES
<222> LOCATION: (17)..(23)
<223> OTHER INFORMATION: Ala, Ser, Val, Lys or Pro
<220> FEATURE:
<221> NAME/KEY: MOD_RES
<222> LOCATION: (25)..(28)
<223> OTHER INFORMATION: Ala, Ser, Val, Lys or Pro
<220> FEATURE:
<221> NAME/KEY: MOD_RES
<222> LOCATION: (30)..(36)
<223> OTHER INFORMATION: Ala, Ser, Val, Lys or Pro
<220> FEATURE:
<221> NAME/KEY: MOD_RES
<222> LOCATION: (38)..(41)
<223> OTHER INFORMATION: Ala, Ser, Val, Lys or Pro
<220> FEATURE:
<221> NAME/KEY: MOD_RES
<222> LOCATION: (43)..(49)
<223> OTHER INFORMATION: Ala, Ser, Val, Lys or Pro
<220> FEATURE:
<221> NAME/KEY: MOD_RES
<222> LOCATION: (51)..(54)
<223> OTHER INFORMATION: Ala, Ser, Val, Lys or Pro
<220> FEATURE:
<221> NAME/KEY: MOD_RES
<222> LOCATION: (56)..(62)
<223> OTHER INFORMATION: Ala, Ser, Val, Lys or Pro
<220> FEATURE:
<221> NAME/KEY: MOD_RES
<222> LOCATION: (64)..(67)
<223> OTHER INFORMATION: Ala, Ser, Val, Lys or Pro
<220> FEATURE:
<221> NAME/KEY: MOD_RES
<222> LOCATION: (69)..(75)
<223> OTHER INFORMATION: Ala, Ser, Val, Lys or Pro
<220> FEATURE:
<221> NAME/KEY: MOD_RES
<222> LOCATION: (77)..(80)
<223> OTHER INFORMATION: Ala, Ser, Val, Lys or Pro
<220> FEATURE:
<221> NAME/KEY: MOD_RES
```

<222> LOCATION: (82)..(88)
<223> OTHER INFORMATION: Ala, Ser, Val, Lys or Pro
<220> FEATURE:
<221> NAME/KEY: MOD_RES
<222> LOCATION: (90)..(93)
<223> OTHER INFORMATION: Ala, Ser, Val, Lys or Pro
<220> FEATURE:
<221> NAME/KEY: MOD_RES
<222> LOCATION: (95)..(101)
<223> OTHER INFORMATION: Ala, Ser, Val, Lys or Pro
<220> FEATURE:
<221> NAME/KEY: MOD_RES
<222> LOCATION: (103)..(104)
<223> OTHER INFORMATION: Ala, Ser, Val, Lys or Pro
<220> FEATURE:
<223> OTHER INFORMATION: This sequence may encompass 1 to 8 13-mer
      repeating units; see specification as filed for detailed
      description of preferred embodiments

<400> SEQUENCE: 34

Xaa Glu Xaa Xaa Xaa Xaa Xaa Xaa Xaa Asp Xaa Xaa Xaa Xaa Glu
1               5                   10                  15

Xaa Xaa Xaa Xaa Xaa Xaa Xaa Asp Xaa Xaa Xaa Xaa Glu Xaa Xaa Xaa
            20                  25                  30

Xaa Xaa Xaa Xaa Asp Xaa Xaa Xaa Xaa Glu Xaa Xaa Xaa Xaa Xaa
        35                  40                  45

Xaa Asp Xaa Xaa Xaa Xaa Glu Xaa Xaa Xaa Xaa Xaa Xaa Asp Xaa
    50                  55                  60

Xaa Xaa Xaa Glu Xaa Xaa Xaa Xaa Xaa Xaa Xaa Asp Xaa Xaa Xaa Xaa
65                  70                  75                  80

Glu Xaa Xaa Xaa Xaa Xaa Xaa Xaa Asp Xaa Xaa Xaa Xaa Glu Xaa Xaa
                85                  90                  95

Xaa Xaa Xaa Xaa Xaa Asp Xaa Xaa
            100

<210> SEQ ID NO 35
<211> LENGTH: 104
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Ala, Ser, Val, Lys or Pro
<220> FEATURE:
<221> NAME/KEY: MOD_RES
<222> LOCATION: (4)..(10)
<223> OTHER INFORMATION: Ala, Ser, Val, Lys or Pro
<220> FEATURE:
<221> NAME/KEY: MOD_RES
<222> LOCATION: (12)..(15)
<223> OTHER INFORMATION: Ala, Ser, Val, Lys or Pro
<220> FEATURE:
<221> NAME/KEY: MOD_RES
<222> LOCATION: (17)..(23)
<223> OTHER INFORMATION: Ala, Ser, Val, Lys or Pro
<220> FEATURE:
<221> NAME/KEY: MOD_RES
<222> LOCATION: (25)..(28)
<223> OTHER INFORMATION: Ala, Ser, Val, Lys or Pro
<220> FEATURE:
<221> NAME/KEY: MOD_RES
<222> LOCATION: (30)..(36)
<223> OTHER INFORMATION: Ala, Ser, Val, Lys or Pro
<220> FEATURE:
<221> NAME/KEY: MOD_RES
<222> LOCATION: (38)..(41)
<223> OTHER INFORMATION: Ala, Ser, Val, Lys or Pro
<220> FEATURE:

```
<221> NAME/KEY: MOD_RES
<222> LOCATION: (43)..(49)
<223> OTHER INFORMATION: Ala, Ser, Val, Lys or Pro
<220> FEATURE:
<221> NAME/KEY: MOD_RES
<222> LOCATION: (51)..(54)
<223> OTHER INFORMATION: Ala, Ser, Val, Lys or Pro
<220> FEATURE:
<221> NAME/KEY: MOD_RES
<222> LOCATION: (56)..(62)
<223> OTHER INFORMATION: Ala, Ser, Val, Lys or Pro
<220> FEATURE:
<221> NAME/KEY: MOD_RES
<222> LOCATION: (64)..(67)
<223> OTHER INFORMATION: Ala, Ser, Val, Lys or Pro
<220> FEATURE:
<221> NAME/KEY: MOD_RES
<222> LOCATION: (69)..(75)
<223> OTHER INFORMATION: Ala, Ser, Val, Lys or Pro
<220> FEATURE:
<221> NAME/KEY: MOD_RES
<222> LOCATION: (77)..(80)
<223> OTHER INFORMATION: Ala, Ser, Val, Lys or Pro
<220> FEATURE:
<221> NAME/KEY: MOD_RES
<222> LOCATION: (82)..(88)
<223> OTHER INFORMATION: Ala, Ser, Val, Lys or Pro
<220> FEATURE:
<221> NAME/KEY: MOD_RES
<222> LOCATION: (90)..(93)
<223> OTHER INFORMATION: Ala, Ser, Val, Lys or Pro
<220> FEATURE:
<221> NAME/KEY: MOD_RES
<222> LOCATION: (95)..(101)
<223> OTHER INFORMATION: Ala, Ser, Val, Lys or Pro
<220> FEATURE:
<221> NAME/KEY: MOD_RES
<222> LOCATION: (103)..(104)
<223> OTHER INFORMATION: Ala, Ser, Val, Lys or Pro
<220> FEATURE:
<223> OTHER INFORMATION: This sequence may encompass 1 to 8 13-mer
      repeating units; see specification as filed for detailed
      description of preferred embodiments

<400> SEQUENCE: 35

Xaa Xaa Asp Xaa Xaa Xaa Xaa Xaa Xaa Xaa Asp Xaa Xaa Xaa Xaa Asp
 1               5                  10                  15

Xaa Xaa Xaa Xaa Xaa Xaa Xaa Asp Xaa Xaa Xaa Xaa Asp Xaa Xaa Xaa
             20                  25                  30

Xaa Xaa Xaa Xaa Asp Xaa Xaa Xaa Xaa Asp Xaa Xaa Xaa Xaa Xaa Xaa
             35                  40                  45

Xaa Asp Xaa Xaa Xaa Xaa Asp Xaa Xaa Xaa Xaa Xaa Xaa Xaa Asp Xaa
 50                  55                  60

Xaa Xaa Xaa Asp Xaa Xaa Xaa Xaa Xaa Xaa Asp Xaa Xaa Xaa Xaa
 65                  70                  75                  80

Asp Xaa Xaa Xaa Xaa Xaa Xaa Xaa Asp Xaa Xaa Xaa Xaa Asp Xaa Xaa
             85                  90                  95

Xaa Xaa Xaa Xaa Xaa Asp Xaa Xaa
            100

<210> SEQ ID NO 36
<211> LENGTH: 104
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Ala, Ser, Val, Lys or Pro
```

```
<220> FEATURE:
<221> NAME/KEY: MOD_RES
<222> LOCATION: (4)..(10)
<223> OTHER INFORMATION: Ala, Ser, Val, Lys or Pro
<220> FEATURE:
<221> NAME/KEY: MOD_RES
<222> LOCATION: (12)..(15)
<223> OTHER INFORMATION: Ala, Ser, Val, Lys or Pro
<220> FEATURE:
<221> NAME/KEY: MOD_RES
<222> LOCATION: (17)..(23)
<223> OTHER INFORMATION: Ala, Ser, Val, Lys or Pro
<220> FEATURE:
<221> NAME/KEY: MOD_RES
<222> LOCATION: (25)..(28)
<223> OTHER INFORMATION: Ala, Ser, Val, Lys or Pro
<220> FEATURE:
<221> NAME/KEY: MOD_RES
<222> LOCATION: (30)..(36)
<223> OTHER INFORMATION: Ala, Ser, Val, Lys or Pro
<220> FEATURE:
<221> NAME/KEY: MOD_RES
<222> LOCATION: (38)..(41)
<223> OTHER INFORMATION: Ala, Ser, Val, Lys or Pro
<220> FEATURE:
<221> NAME/KEY: MOD_RES
<222> LOCATION: (43)..(49)
<223> OTHER INFORMATION: Ala, Ser, Val, Lys or Pro
<220> FEATURE:
<221> NAME/KEY: MOD_RES
<222> LOCATION: (51)..(54)
<223> OTHER INFORMATION: Ala, Ser, Val, Lys or Pro
<220> FEATURE:
<221> NAME/KEY: MOD_RES
<222> LOCATION: (56)..(62)
<223> OTHER INFORMATION: Ala, Ser, Val, Lys or Pro
<220> FEATURE:
<221> NAME/KEY: MOD_RES
<222> LOCATION: (64)..(67)
<223> OTHER INFORMATION: Ala, Ser, Val, Lys or Pro
<220> FEATURE:
<221> NAME/KEY: MOD_RES
<222> LOCATION: (69)..(75)
<223> OTHER INFORMATION: Ala, Ser, Val, Lys or Pro
<220> FEATURE:
<221> NAME/KEY: MOD_RES
<222> LOCATION: (77)..(80)
<223> OTHER INFORMATION: Ala, Ser, Val, Lys or Pro
<220> FEATURE:
<221> NAME/KEY: MOD_RES
<222> LOCATION: (82)..(88)
<223> OTHER INFORMATION: Ala, Ser, Val, Lys or Pro
<220> FEATURE:
<221> NAME/KEY: MOD_RES
<222> LOCATION: (90)..(93)
<223> OTHER INFORMATION: Ala, Ser, Val, Lys or Pro
<220> FEATURE:
<221> NAME/KEY: MOD_RES
<222> LOCATION: (95)..(101)
<223> OTHER INFORMATION: Ala, Ser, Val, Lys or Pro
<220> FEATURE:
<221> NAME/KEY: MOD_RES
<222> LOCATION: (103)..(104)
<223> OTHER INFORMATION: Ala, Ser, Val, Lys or Pro
<220> FEATURE:
<223> OTHER INFORMATION: This sequence may encompass 1 to 8 13-mer
      repeating units; see specification as filed for detailed
      description of preferred embodiments

<400> SEQUENCE: 36

Xaa Xaa Asp Xaa Xaa Xaa Xaa Xaa Xaa Xaa Glu Xaa Xaa Xaa Xaa Asp
1               5                   10                  15

Xaa Xaa Xaa Xaa Xaa Xaa Xaa Glu Xaa Xaa Xaa Xaa Asp Xaa Xaa Xaa
            20                  25                  30

Xaa Xaa Xaa Xaa Glu Xaa Xaa Xaa Xaa Asp Xaa Xaa Xaa Xaa Xaa Xaa
        35                  40                  45
```

-continued

```
Xaa Glu Xaa Xaa Xaa Xaa Asp Xaa Xaa Xaa Xaa Xaa Xaa Xaa Glu Xaa
     50                  55                  60

Xaa Xaa Xaa Asp Xaa Xaa Xaa Xaa Xaa Xaa Glu Xaa Xaa Xaa Xaa
 65                  70                  75                  80

Asp Xaa Xaa Xaa Xaa Xaa Xaa Glu Xaa Xaa Xaa Xaa Asp Xaa Xaa
                 85                  90                  95

Xaa Xaa Xaa Xaa Xaa Glu Xaa Xaa
            100

<210> SEQ ID NO 37
<211> LENGTH: 104
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Ala, Ser, Val, Lys or Pro
<220> FEATURE:
<221> NAME/KEY: MOD_RES
<222> LOCATION: (4)..(5)
<223> OTHER INFORMATION: Ala, Ser, Val, Lys or Pro
<220> FEATURE:
<221> NAME/KEY: MOD_RES
<222> LOCATION: (7)..(10)
<223> OTHER INFORMATION: Ala, Ser, Val, Lys or Pro
<220> FEATURE:
<221> NAME/KEY: MOD_RES
<222> LOCATION: (12)..(15)
<223> OTHER INFORMATION: Ala, Ser, Val, Lys or Pro
<220> FEATURE:
<221> NAME/KEY: MOD_RES
<222> LOCATION: (17)..(18)
<223> OTHER INFORMATION: Ala, Ser, Val, Lys or Pro
<220> FEATURE:
<221> NAME/KEY: MOD_RES
<222> LOCATION: (20)..(23)
<223> OTHER INFORMATION: Ala, Ser, Val, Lys or Pro
<220> FEATURE:
<221> NAME/KEY: MOD_RES
<222> LOCATION: (25)..(28)
<223> OTHER INFORMATION: Ala, Ser, Val, Lys or Pro
<220> FEATURE:
<221> NAME/KEY: MOD_RES
<222> LOCATION: (30)..(31)
<223> OTHER INFORMATION: Ala, Ser, Val, Lys or Pro
<220> FEATURE:
<221> NAME/KEY: MOD_RES
<222> LOCATION: (33)..(36)
<223> OTHER INFORMATION: Ala, Ser, Val, Lys or Pro
<220> FEATURE:
<221> NAME/KEY: MOD_RES
<222> LOCATION: (38)..(41)
<223> OTHER INFORMATION: Ala, Ser, Val, Lys or Pro
<220> FEATURE:
<221> NAME/KEY: MOD_RES
<222> LOCATION: (43)..(44)
<223> OTHER INFORMATION: Ala, Ser, Val, Lys or Pro
<220> FEATURE:
<221> NAME/KEY: MOD_RES
<222> LOCATION: (46)..(49)
<223> OTHER INFORMATION: Ala, Ser, Val, Lys or Pro
<220> FEATURE:
<221> NAME/KEY: MOD_RES
<222> LOCATION: (51)..(54)
<223> OTHER INFORMATION: Ala, Ser, Val, Lys or Pro
<220> FEATURE:
<221> NAME/KEY: MOD_RES
<222> LOCATION: (56)..(57)
<223> OTHER INFORMATION: Ala, Ser, Val, Lys or Pro
<220> FEATURE:
<221> NAME/KEY: MOD_RES
```

```
<222> LOCATION: (59)..(62)
<223> OTHER INFORMATION: Ala, Ser, Val, Lys or Pro
<220> FEATURE:
<221> NAME/KEY: MOD_RES
<222> LOCATION: (64)..(67)
<223> OTHER INFORMATION: Ala, Ser, Val, Lys or Pro
<220> FEATURE:
<221> NAME/KEY: MOD_RES
<222> LOCATION: (69)..(70)
<223> OTHER INFORMATION: Ala, Ser, Val, Lys or Pro
<220> FEATURE:
<221> NAME/KEY: MOD_RES
<222> LOCATION: (72)..(75)
<223> OTHER INFORMATION: Ala, Ser, Val, Lys or Pro
<220> FEATURE:
<221> NAME/KEY: MOD_RES
<222> LOCATION: (77)..(80)
<223> OTHER INFORMATION: Ala, Ser, Val, Lys or Pro
<220> FEATURE:
<221> NAME/KEY: MOD_RES
<222> LOCATION: (82)..(83)
<223> OTHER INFORMATION: Ala, Ser, Val, Lys or Pro
<220> FEATURE:
<221> NAME/KEY: MOD_RES
<222> LOCATION: (85)..(88)
<223> OTHER INFORMATION: Ala, Ser, Val, Lys or Pro
<220> FEATURE:
<221> NAME/KEY: MOD_RES
<222> LOCATION: (90)..(93)
<223> OTHER INFORMATION: Ala, Ser, Val, Lys or Pro
<220> FEATURE:
<221> NAME/KEY: MOD_RES
<222> LOCATION: (95)..(96)
<223> OTHER INFORMATION: Ala, Ser, Val, Lys or Pro
<220> FEATURE:
<221> NAME/KEY: MOD_RES
<222> LOCATION: (98)..(101)
<223> OTHER INFORMATION: Ala, Ser, Val, Lys or Pro
<220> FEATURE:
<221> NAME/KEY: MOD_RES
<222> LOCATION: (103)..(104)
<223> OTHER INFORMATION: Ala, Ser, Val, Lys or Pro
<220> FEATURE:
<223> OTHER INFORMATION: This sequence may encompass 1 to 8 13-mer
      repeating units; see specification as filed for detailed
      description of preferred embodiments

<400> SEQUENCE: 37

Xaa Xaa Glu Xaa Xaa Val Xaa Xaa Xaa Xaa Asp Xaa Xaa Xaa Xaa Glu
1               5                   10                  15

Xaa Xaa Val Xaa Xaa Xaa Xaa Asp Xaa Xaa Xaa Glu Xaa Xaa Val
            20                  25                  30

Xaa Xaa Xaa Xaa Asp Xaa Xaa Xaa Xaa Glu Xaa Xaa Val Xaa Xaa Xaa
        35                  40                  45

Xaa Asp Xaa Xaa Xaa Xaa Glu Xaa Xaa Val Xaa Xaa Xaa Xaa Asp Xaa
    50                  55                  60

Xaa Xaa Xaa Glu Xaa Xaa Val Xaa Xaa Xaa Xaa Asp Xaa Xaa Xaa Xaa
65                  70                  75                  80

Glu Xaa Xaa Val Xaa Xaa Xaa Xaa Asp Xaa Xaa Xaa Xaa Glu Xaa Xaa
                85                  90                  95

Val Xaa Xaa Xaa Xaa Asp Xaa Xaa
            100

<210> SEQ ID NO 38
<211> LENGTH: 104
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (1)..(2)
<223> OTHER INFORMATION: Ala, Ser, Val, Lys or Pro
<220> FEATURE:
<221> NAME/KEY: MOD_RES
<222> LOCATION: (4)..(5)
<223> OTHER INFORMATION: Ala, Ser, Val, Lys or Pro
<220> FEATURE:
<221> NAME/KEY: MOD_RES
<222> LOCATION: (7)..(10)
<223> OTHER INFORMATION: Ala, Ser, Val, Lys or Pro
<220> FEATURE:
<221> NAME/KEY: MOD_RES
<222> LOCATION: (12)..(15)
<223> OTHER INFORMATION: Ala, Ser, Val, Lys or Pro
<220> FEATURE:
<221> NAME/KEY: MOD_RES
<222> LOCATION: (17)..(18)
<223> OTHER INFORMATION: Ala, Ser, Val, Lys or Pro
<220> FEATURE:
<221> NAME/KEY: MOD_RES
<222> LOCATION: (20)..(23)
<223> OTHER INFORMATION: Ala, Ser, Val, Lys or Pro
<220> FEATURE:
<221> NAME/KEY: MOD_RES
<222> LOCATION: (25)..(28)
<223> OTHER INFORMATION: Ala, Ser, Val, Lys or Pro
<220> FEATURE:
<221> NAME/KEY: MOD_RES
<222> LOCATION: (30)..(31)
<223> OTHER INFORMATION: Ala, Ser, Val, Lys or Pro
<220> FEATURE:
<221> NAME/KEY: MOD_RES
<222> LOCATION: (33)..(36)
<223> OTHER INFORMATION: Ala, Ser, Val, Lys or Pro
<220> FEATURE:
<221> NAME/KEY: MOD_RES
<222> LOCATION: (38)..(41)
<223> OTHER INFORMATION: Ala, Ser, Val, Lys or Pro
<220> FEATURE:
<221> NAME/KEY: MOD_RES
<222> LOCATION: (43)..(44)
<223> OTHER INFORMATION: Ala, Ser, Val, Lys or Pro
<220> FEATURE:
<221> NAME/KEY: MOD_RES
<222> LOCATION: (46)..(49)
<223> OTHER INFORMATION: Ala, Ser, Val, Lys or Pro
<220> FEATURE:
<221> NAME/KEY: MOD_RES
<222> LOCATION: (51)..(54)
<223> OTHER INFORMATION: Ala, Ser, Val, Lys or Pro
<220> FEATURE:
<221> NAME/KEY: MOD_RES
<222> LOCATION: (56)..(57)
<223> OTHER INFORMATION: Ala, Ser, Val, Lys or Pro
<220> FEATURE:
<221> NAME/KEY: MOD_RES
<222> LOCATION: (59)..(62)
<223> OTHER INFORMATION: Ala, Ser, Val, Lys or Pro
<220> FEATURE:
<221> NAME/KEY: MOD_RES
<222> LOCATION: (64)..(67)
<223> OTHER INFORMATION: Ala, Ser, Val, Lys or Pro
<220> FEATURE:
<221> NAME/KEY: MOD_RES
<222> LOCATION: (69)..(70)
<223> OTHER INFORMATION: Ala, Ser, Val, Lys or Pro
<220> FEATURE:
<221> NAME/KEY: MOD_RES
<222> LOCATION: (72)..(75)
<223> OTHER INFORMATION: Ala, Ser, Val, Lys or Pro
<220> FEATURE:
<221> NAME/KEY: MOD_RES
<222> LOCATION: (77)..(80)
<223> OTHER INFORMATION: Ala, Ser, Val, Lys or Pro
<220> FEATURE:
<221> NAME/KEY: MOD_RES
<222> LOCATION: (82)..(83)
<223> OTHER INFORMATION: Ala, Ser, Val, Lys or Pro
```

```
<220> FEATURE:
<221> NAME/KEY: MOD_RES
<222> LOCATION: (85)..(88)
<223> OTHER INFORMATION: Ala, Ser, Val, Lys or Pro
<220> FEATURE:
<221> NAME/KEY: MOD_RES
<222> LOCATION: (90)..(93)
<223> OTHER INFORMATION: Ala, Ser, Val, Lys or Pro
<220> FEATURE:
<221> NAME/KEY: MOD_RES
<222> LOCATION: (95)..(96)
<223> OTHER INFORMATION: Ala, Ser, Val, Lys or Pro
<220> FEATURE:
<221> NAME/KEY: MOD_RES
<222> LOCATION: (98)..(101)
<223> OTHER INFORMATION: Ala, Ser, Val, Lys or Pro
<220> FEATURE:
<221> NAME/KEY: MOD_RES
<222> LOCATION: (103)..(104)
<223> OTHER INFORMATION: Ala, Ser, Val, Lys or Pro
<220> FEATURE:
<223> OTHER INFORMATION: This sequence may encompass 1 to 8 13-mer
      repeating units; see specification as filed for detailed
      description of preferred embodiments

<400> SEQUENCE: 38

Xaa Xaa Asp Xaa Xaa Val Xaa Xaa Xaa Xaa Asp Xaa Xaa Xaa Xaa Asp
1               5                   10                  15

Xaa Xaa Val Xaa Xaa Xaa Xaa Asp Xaa Xaa Xaa Xaa Asp Xaa Xaa Val
            20                  25                  30

Xaa Xaa Xaa Xaa Asp Xaa Xaa Xaa Asp Xaa Xaa Val Xaa Xaa Xaa
        35                  40                  45

Xaa Asp Xaa Xaa Xaa Xaa Asp Xaa Xaa Val Xaa Xaa Xaa Xaa Asp Xaa
    50                  55                  60

Xaa Xaa Xaa Asp Xaa Xaa Val Xaa Xaa Xaa Xaa Asp Xaa Xaa Xaa Xaa
65                  70                  75                  80

Asp Xaa Xaa Val Xaa Xaa Xaa Xaa Asp Xaa Xaa Xaa Xaa Asp Xaa Xaa
                85                  90                  95

Val Xaa Xaa Xaa Xaa Asp Xaa Xaa
            100

<210> SEQ ID NO 39
<211> LENGTH: 104
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Ala, Ser, Val, Lys or Pro
<220> FEATURE:
<221> NAME/KEY: MOD_RES
<222> LOCATION: (4)..(5)
<223> OTHER INFORMATION: Ala, Ser, Val, Lys or Pro
<220> FEATURE:
<221> NAME/KEY: MOD_RES
<222> LOCATION: (7)..(10)
<223> OTHER INFORMATION: Ala, Ser, Val, Lys or Pro
<220> FEATURE:
<221> NAME/KEY: MOD_RES
<222> LOCATION: (12)..(15)
<223> OTHER INFORMATION: Ala, Ser, Val, Lys or Pro
<220> FEATURE:
<221> NAME/KEY: MOD_RES
<222> LOCATION: (17)..(18)
<223> OTHER INFORMATION: Ala, Ser, Val, Lys or Pro
<220> FEATURE:
<221> NAME/KEY: MOD_RES
<222> LOCATION: (20)..(23)
```

```
<223> OTHER INFORMATION: Ala, Ser, Val, Lys or Pro
<220> FEATURE:
<221> NAME/KEY: MOD_RES
<222> LOCATION: (25)..(28)
<223> OTHER INFORMATION: Ala, Ser, Val, Lys or Pro
<220> FEATURE:
<221> NAME/KEY: MOD_RES
<222> LOCATION: (30)..(31)
<223> OTHER INFORMATION: Ala, Ser, Val, Lys or Pro
<220> FEATURE:
<221> NAME/KEY: MOD_RES
<222> LOCATION: (33)..(36)
<223> OTHER INFORMATION: Ala, Ser, Val, Lys or Pro
<220> FEATURE:
<221> NAME/KEY: MOD_RES
<222> LOCATION: (38)..(41)
<223> OTHER INFORMATION: Ala, Ser, Val, Lys or Pro
<220> FEATURE:
<221> NAME/KEY: MOD_RES
<222> LOCATION: (43)..(44)
<223> OTHER INFORMATION: Ala, Ser, Val, Lys or Pro
<220> FEATURE:
<221> NAME/KEY: MOD_RES
<222> LOCATION: (46)..(49)
<223> OTHER INFORMATION: Ala, Ser, Val, Lys or Pro
<220> FEATURE:
<221> NAME/KEY: MOD_RES
<222> LOCATION: (51)..(54)
<223> OTHER INFORMATION: Ala, Ser, Val, Lys or Pro
<220> FEATURE:
<221> NAME/KEY: MOD_RES
<222> LOCATION: (56)..(57)
<223> OTHER INFORMATION: Ala, Ser, Val, Lys or Pro
<220> FEATURE:
<221> NAME/KEY: MOD_RES
<222> LOCATION: (59)..(62)
<223> OTHER INFORMATION: Ala, Ser, Val, Lys or Pro
<220> FEATURE:
<221> NAME/KEY: MOD_RES
<222> LOCATION: (64)..(67)
<223> OTHER INFORMATION: Ala, Ser, Val, Lys or Pro
<220> FEATURE:
<221> NAME/KEY: MOD_RES
<222> LOCATION: (69)..(70)
<223> OTHER INFORMATION: Ala, Ser, Val, Lys or Pro
<220> FEATURE:
<221> NAME/KEY: MOD_RES
<222> LOCATION: (72)..(75)
<223> OTHER INFORMATION: Ala, Ser, Val, Lys or Pro
<220> FEATURE:
<221> NAME/KEY: MOD_RES
<222> LOCATION: (77)..(80)
<223> OTHER INFORMATION: Ala, Ser, Val, Lys or Pro
<220> FEATURE:
<221> NAME/KEY: MOD_RES
<222> LOCATION: (82)..(83)
<223> OTHER INFORMATION: Ala, Ser, Val, Lys or Pro
<220> FEATURE:
<221> NAME/KEY: MOD_RES
<222> LOCATION: (85)..(88)
<223> OTHER INFORMATION: Ala, Ser, Val, Lys or Pro
<220> FEATURE:
<221> NAME/KEY: MOD_RES
<222> LOCATION: (90)..(93)
<223> OTHER INFORMATION: Ala, Ser, Val, Lys or Pro
<220> FEATURE:
<221> NAME/KEY: MOD_RES
<222> LOCATION: (95)..(96)
<223> OTHER INFORMATION: Ala, Ser, Val, Lys or Pro
<220> FEATURE:
<221> NAME/KEY: MOD_RES
<222> LOCATION: (98)..(101)
<223> OTHER INFORMATION: Ala, Ser, Val, Lys or Pro
<220> FEATURE:
<221> NAME/KEY: MOD_RES
<222> LOCATION: (103)..(104)
<223> OTHER INFORMATION: Ala, Ser, Val, Lys or Pro
<220> FEATURE:
<223> OTHER INFORMATION: This sequence may encompass 1 to 8 13-mer
```

-continued repeating units; see specification as filed for detailed
description of preferred embodiments

<400> SEQUENCE: 39

Xaa Xaa Asp Xaa Xaa Val Xaa Xaa Xaa Xaa Glu Xaa Xaa Xaa Xaa Asp
1               5                   10                  15

Xaa Xaa Val Xaa Xaa Xaa Xaa Glu Xaa Xaa Xaa Xaa Asp Xaa Xaa Val
            20                  25                  30

Xaa Xaa Xaa Xaa Glu Xaa Xaa Xaa Xaa Asp Xaa Xaa Val Xaa Xaa Xaa
        35                  40                  45

Xaa Glu Xaa Xaa Xaa Xaa Asp Xaa Xaa Val Xaa Xaa Xaa Xaa Glu Xaa
    50                  55                  60

Xaa Xaa Asp Xaa Xaa Val Xaa Xaa Xaa Xaa Glu Xaa Xaa Xaa Xaa
65                  70                  75                  80

Asp Xaa Xaa Val Xaa Xaa Xaa Xaa Glu Xaa Xaa Xaa Xaa Asp Xaa Xaa
                85                  90                  95

Val Xaa Xaa Xaa Xaa Glu Xaa Xaa
            100

<210> SEQ ID NO 40
<211> LENGTH: 104
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Ala, Ser, Val, Lys or Pro
<220> FEATURE:
<221> NAME/KEY: MOD_RES
<222> LOCATION: (4)..(5)
<223> OTHER INFORMATION: Ala, Ser, Val, Lys or Pro
<220> FEATURE:
<221> NAME/KEY: MOD_RES
<222> LOCATION: (7)..(10)
<223> OTHER INFORMATION: Ala, Ser, Val, Lys or Pro
<220> FEATURE:
<221> NAME/KEY: MOD_RES
<222> LOCATION: (12)..(15)
<223> OTHER INFORMATION: Ala, Ser, Val, Lys or Pro
<220> FEATURE:
<221> NAME/KEY: MOD_RES
<222> LOCATION: (17)..(18)
<223> OTHER INFORMATION: Ala, Ser, Val, Lys or Pro
<220> FEATURE:
<221> NAME/KEY: MOD_RES
<222> LOCATION: (20)..(23)
<223> OTHER INFORMATION: Ala, Ser, Val, Lys or Pro
<220> FEATURE:
<221> NAME/KEY: MOD_RES
<222> LOCATION: (25)..(28)
<223> OTHER INFORMATION: Ala, Ser, Val, Lys or Pro
<220> FEATURE:
<221> NAME/KEY: MOD_RES
<222> LOCATION: (30)..(31)
<223> OTHER INFORMATION: Ala, Ser, Val, Lys or Pro
<220> FEATURE:
<221> NAME/KEY: MOD_RES
<222> LOCATION: (33)..(36)
<223> OTHER INFORMATION: Ala, Ser, Val, Lys or Pro
<220> FEATURE:
<221> NAME/KEY: MOD_RES
<222> LOCATION: (38)..(41)
<223> OTHER INFORMATION: Ala, Ser, Val, Lys or Pro
<220> FEATURE:
<221> NAME/KEY: MOD_RES
<222> LOCATION: (43)..(44)
<223> OTHER INFORMATION: Ala, Ser, Val, Lys or Pro
<220> FEATURE:

```
<221> NAME/KEY: MOD_RES
<222> LOCATION: (46)..(49)
<223> OTHER INFORMATION: Ala, Ser, Val, Lys or Pro
<220> FEATURE:
<221> NAME/KEY: MOD_RES
<222> LOCATION: (51)..(54)
<223> OTHER INFORMATION: Ala, Ser, Val, Lys or Pro
<220> FEATURE:
<221> NAME/KEY: MOD_RES
<222> LOCATION: (56)..(57)
<223> OTHER INFORMATION: Ala, Ser, Val, Lys or Pro
<220> FEATURE:
<221> NAME/KEY: MOD_RES
<222> LOCATION: (59)..(62)
<223> OTHER INFORMATION: Ala, Ser, Val, Lys or Pro
<220> FEATURE:
<221> NAME/KEY: MOD_RES
<222> LOCATION: (64)..(67)
<223> OTHER INFORMATION: Ala, Ser, Val, Lys or Pro
<220> FEATURE:
<221> NAME/KEY: MOD_RES
<222> LOCATION: (69)..(70)
<223> OTHER INFORMATION: Ala, Ser, Val, Lys or Pro
<220> FEATURE:
<221> NAME/KEY: MOD_RES
<222> LOCATION: (72)..(75)
<223> OTHER INFORMATION: Ala, Ser, Val, Lys or Pro
<220> FEATURE:
<221> NAME/KEY: MOD_RES
<222> LOCATION: (77)..(80)
<223> OTHER INFORMATION: Ala, Ser, Val, Lys or Pro
<220> FEATURE:
<221> NAME/KEY: MOD_RES
<222> LOCATION: (82)..(83)
<223> OTHER INFORMATION: Ala, Ser, Val, Lys or Pro
<220> FEATURE:
<221> NAME/KEY: MOD_RES
<222> LOCATION: (85)..(88)
<223> OTHER INFORMATION: Ala, Ser, Val, Lys or Pro
<220> FEATURE:
<221> NAME/KEY: MOD_RES
<222> LOCATION: (90)..(93)
<223> OTHER INFORMATION: Ala, Ser, Val, Lys or Pro
<220> FEATURE:
<221> NAME/KEY: MOD_RES
<222> LOCATION: (95)..(96)
<223> OTHER INFORMATION: Ala, Ser, Val, Lys or Pro
<220> FEATURE:
<221> NAME/KEY: MOD_RES
<222> LOCATION: (98)..(101)
<223> OTHER INFORMATION: Ala, Ser, Val, Lys or Pro
<220> FEATURE:
<221> NAME/KEY: MOD_RES
<222> LOCATION: (103)..(104)
<223> OTHER INFORMATION: Ala, Ser, Val, Lys or Pro
<220> FEATURE:
<223> OTHER INFORMATION: This sequence may encompass 1 to 8 13-mer
     repeating units; see specification as filed for detailed
     description of preferred embodiments

<400> SEQUENCE: 40

Xaa Xaa Glu Xaa Xaa Val Xaa Xaa Xaa Glu Xaa Xaa Xaa Xaa Glu
1               5                   10                  15

Xaa Xaa Val Xaa Xaa Xaa Glu Xaa Xaa Xaa Glu Xaa Xaa Val
            20                  25                  30

Xaa Xaa Xaa Xaa Glu Xaa Xaa Xaa Xaa Glu Xaa Xaa Val Xaa Xaa Xaa
        35                  40                  45

Xaa Glu Xaa Xaa Xaa Xaa Glu Xaa Xaa Val Xaa Xaa Xaa Xaa Glu Xaa
    50                  55                  60

Xaa Xaa Xaa Glu Xaa Xaa Val Xaa Xaa Xaa Xaa Glu Xaa Xaa Xaa Xaa
65                  70                  75                  80

Glu Xaa Xaa Val Xaa Xaa Xaa Xaa Glu Xaa Xaa Xaa Xaa Glu Xaa Xaa
                85                  90                  95
```

```
Val Xaa Xaa Xaa Xaa Glu Xaa Xaa
            100

<210> SEQ ID NO 41
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Ala Glu Lys Tyr Ala
1               5

<210> SEQ ID NO 42
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ala Glu Lys Val Ala
1               5

<210> SEQ ID NO 43
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ala Glu Lys Phe Ala
1               5

<210> SEQ ID NO 44
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Ala Lys Tyr Ala Glu
1               5

<210> SEQ ID NO 45
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Glu Ala Lys Tyr Ala
1               5

<210> SEQ ID NO 46
<211> LENGTH: 5
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 46

Ala Lys Val Ala Glu
1               5

<210> SEQ ID NO 47
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Glu Ala Lys Val Ala
1               5

<210> SEQ ID NO 48
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ala Lys Phe Ala Glu
1               5

<210> SEQ ID NO 49
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Glu Ala Lys Phe Ala
1               5
```